United States Patent [19]

Michaelides et al.

[11] Patent Number: 5,597,832

[45] Date of Patent: Jan. 28, 1997

[54] TETRACYCLIC COMPOUNDS AS DOPAMINE AGONISTS

[75] Inventors: Michael R. Michaelides, Gurnee, Ill.; Yufeng Hong, San Diego, Calif.

[73] Assignee: Abbott Laboratories, Abbott Park, Ill.

[21] Appl. No.: 337,348

[22] Filed: Nov. 10, 1994

Related U.S. Application Data

[63] Continuation-in-part of Ser. No. 209,982, Mar. 17, 1994, abandoned, which is a continuation-in-part of Ser. No. 43,424, Apr. 6, 1993, abandoned.

[51] Int. Cl.$^6$ .................. A01N 43/90; C07D 471/00; C07D 487/00; C07D 498/00
[52] U.S. Cl. .................. 514/285; 514/287; 546/62; 546/64; 546/65; 546/70; 546/77; 546/78
[58] Field of Search .................. 546/62, 64, 65, 546/70, 77, 78; 514/285, 287

[56] References Cited

U.S. PATENT DOCUMENTS

| | | |
|---|---|---|
| 2,691,024 | 10/1954 | Horlein et al. |
| 3,541,100 | 11/1970 | Ramirez et al. |
| 3,830,647 | 8/1974 | Janssens et al. |
| 3,832,171 | 8/1974 | Janssens et al. |
| 3,943,137 | 3/1976 | Higuchi et al. |
| 4,145,434 | 3/1979 | Van DeBerg. |
| 4,282,227 | 8/1981 | Brenner. |
| 4,340,600 | 7/1982 | Brenner et al. |
| 5,047,536 | 9/1991 | Nichols. |

FOREIGN PATENT DOCUMENTS

WO93/24462  12/1993  WIPO.

OTHER PUBLICATIONS

Katerinopoulos, et al., "Structure–Activity Relationships for Dopamine Analogs: A Review", in *Drugs of the Future*, vol. 12, pp. 223–253, 1987.

Anderson, et al., "Thienopyridine Derivatives Identified as the First Selective, Full Efficacy, Dopamine D1 Receptor Agonists", *European Journal of Pharmacology*, 13 pp. 291–292, 1987.

Kiguchi, et al., "A Route for Total Synthesis of Ergot Alkaloids Synthesis of the Despyrrole Analogs of Methyl Lysergate, Isolysergol, and isofumigaclavine A" *Heterocycles*, 19, pp. 1873–1877, 1982.

Kaiser, et al., "Dopamine Receptors: Functions, Subtypes and Emerging Concepts", in *Medicinal Research Reviews*, vol. 5, pp. 145–229, 1985.

Wei and Teitel, "Synthesis of a Benzo[a]Phenanthridine Isomeric with Apomorphine" *Heterocycles*, 8 p. 97, 1977.

Brewster, et al., "Trans–10, 11,Dihydroxy–5,6,61,7,8, 12b–Hexahydrobenzo[a]Phenanthridine: A Highly Potent Selective Dopamine $D_1$ Full Agonists", *Journal of Medicinal Chemistry*, 33, pp. 1756–1764, 1990.

*Primary Examiner*—Shean C. Wu
*Attorney, Agent, or Firm*—Monte R. Browder

[57] ABSTRACT

A tetracyclic compound of the formula:

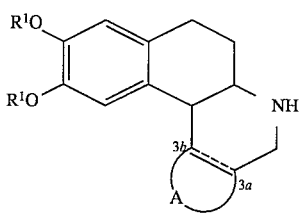

wherein A and the atoms to which it is attached and the optional double bond represent a mono- or di-heterocyclic ring selected from:

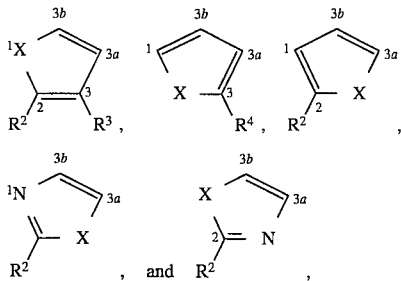

wherein $R^1$, $R^2$, $R^3$, $R^4$ and X are specifically defined, which compounds are useful in the treatment of dopamine-related neurological, psychological and cardiovascular disorders as well as in the treatment of substance abuse and other addictive behavior disorders, cognitive impairment and attention deficit disorder.

11 Claims, No Drawings

1

TETRACYCLIC COMPOUNDS AS DOPAMINE AGONISTS

The application is a continuation-in-part of abandoned U.S. patent application Ser. No. 08/209,982, filed Mar. 17, 1994, which was a continuation-in-part of U.S. patent application Ser. No. 08/043,424, filed Apr. 6, 1993, now abandoned.

TECHNICAL FIELD

This invention relates to novel tetracyclic compounds which are selective dopamine agonists useful for treating dopamine-related neurological, psychological, cardiovascular, cognitive and behavioral disorders.

BACKGROUND OF THE INVENTION

Dopamine is an important neurotransmitter in the central nervous system (CNS), where it is involved with motor function, perception, arousal, motivation and emotion. Dopamine imbalance is believed to play a key role in a number of CNS-related disorders such as schizophrenia, Parkinson's disease, drug abuse, eating disorders and depression. Dopamine also has several important roles in the peripheral nervous system, such as in the control of blood to the kidneys and an autonomic ganglion transmission.

Dopamine receptors in the CNS have traditionally been divided into two general categories, designated D-1 and D-2 receptors, based on biochemical and pharmacological differences between the two receptor types, and recently from the study of the molecular biology of dopamine receptors in the CNS. (For a review of the classification and function of dopamine receptor subtypes, see C. Kaiser and T. Jain, "Dopamine Receptors: Functions, Subtypes and Emerging Concepts", *Medicinal Research Reviews*, 5:145–229, 1985.) Recent additional evidence has suggested an even greater heterogeneity of the dopamine receptors with three additional dopamine receptors being defined through molecular cloning techniques: the D3 and D4, which are classified as D2-like and the D5, which exhibits D1 receptor-like pharmacology (D. Sibley and F. Monsma, "Molecular Biology of Dopamine receptors", in TIPS, Vol. 13, pp. 61–69, 1992). Attempts to understand the physiological and pathophysiological roles of the various dopamine receptors are continuing to unveil new avenues for novel therapeutic approaches for the treatment of dopamine-related disorders.

A particular dopamine-related problem involves the loss of striatal dopamine within the basal ganglia, the region of the mammalian brain that is involved with motor control, which has been established as the fundamental deficit in Parkinson's disease and primary to the etiology of that disease state. This deficiency is addressed via dopamine replacement therapy, primarily with L-DOPA (3,4-dihydroxyphenylalanine), which is converted to dopamine within the brain. L-DOPA has been the cornerstone of Parkinson's disease therapy, and the successes achieved with its therapy have led to the testing of other compounds capable of eliciting the post-synaptic receptor actions of dopamine. Bromocriptine, the most widely used direct-acting dopamine agonist for the treatment of Parkinson's disease, is administered adjunctively with L-DOPA in order to lower dosage of L-DOPA required to achieve the desired therapeutic response. Bromocriptine alone has been shown to relieve Parkinson's disease symptoms in some patients, allowing for a delay in the onset of L-DOPA therapy, but the response to bromocriptine alone is not as great as that observed with L-DOPA. The current therapies for Parkinson's disease, including L-DOPA and bromocriptine, are, however, unfortunately associated with a number of serious side-effects and limitations, such as the development of dyskinesias, severe response fluctuations (on-off phenomenon) and diminishing efficacy during treatment.

An excess of dopamine in the brain, on the other hand, has been identified, as a result of the pioneering work of Carlsson and others in the 1960's, as the cause of schizophrenia, a psychiatric illness involving disturbance of thought processes, hallucinations and loss of touch with reality. Chronic abuse of stimulants, such as amphetamines, known to enhance dopaminergic activity in the brain, can lead to a paranoid psychosis that is clinically indistinguishable from classic paranoid schizophrenia, further supporting this dopamine theory of schizophrenia.

Anti-schizophrenic drugs are postulated to exert their effects by blocking the dopamine receptors (i.e., acting as receptor antagonists), and consequently preventing excess receptor stimulation (G. P. Reynolds, "Developments in the drug treatment of schizophrenia", in *TIPS*, 13:116–121, 1992). These antipsychotic agents frequently also produce undesirable side-effects, however, the most common of which are the extrapyramidal effects that include bizarre involuntary movements and Parkinson-like states, as well as sedation and hypotension. Because of these often-severe side-effects and the high incidence of patients unresponsive to dopamine blocking drugs, novel and improved therapies continue to be sought.

One complement to dopamine receptor antagonists for the treatment of schizophrenia has included the use of low doses of dopamine agonists, such as apomorphine and bromocriptine (also discussed above), which have been reported to produce antipsychotic effects, possibly due to preferential activation of dopamine presynaptic receptors resulting in decreased dopaminergic activity (M. Del Zompo et al, "Dopamine agonists in the treatment of schizophrenia", *Progress in Brain Research*, 65:41–48, 1986 and H. Y. Meltzer, "Novel Approaches to the Pharmacology of Schizophrenia", *Drug Development Research*, 9:23–40, 1986). In addition, the dopamine D1-selective agonist, SKF 38393, when used in conjunction with the antipsychotic drug, haloperidol, a D2 antagonist, has been shown to ameliorate the undesired side-effects of the haloperidol (M. Davidson, "Effects of the D-1 Agonist SKF-38393 Combined With Haloperidol in Schizophrenic Patients", *Arch Gen. Psychiatry*, 47:190–191, 1990).

Growing evidence (reviewed by R. A. Wise and P. -P. Rompre in "Brain Dopamine and Reward", *Annual Review of Psychology*, 40:191–225, 1989) suggests that dopamine also has a central role in the brain's reward system. For example, animals trained to self-administer cocaine will increase their consumption of this drug after treatment with either a D-1 or a D-2 receptor antagonist, presumably in order to maintain the elevated dopamine levels responsible for the drug's euphorigenic and reinforcing properties (D. R. Britton et al, "Evidence for Involvement of Both D1 and D2 Receptors in Maintaining Cocaine Self-Administration", *Pharmacology Biochemistry & Behavior*, 39:911–915, 1991). The D-1 agonist, SKF 38393, has also been reported to decrease food intake by rats, presumably by direct action of the drug on neural feeding mechanisms. Because of this interrelationship between dopamine and reward, dopaminergic agents would be useful for the treatment of substance abuse and other addictive behavior disorders, including cocaine addiction, nicotine addiction and eating disorders.

Affective disorders, the most common psychiatric disorders in adults, which are characterized by changes in mood as the primary clinical manifestation, result from a reduction in the central nervous system of certain biogenic amine neurotransmitters, such as dopamine, noradrenaline and serotonin. Currently-available antidepressants work primarily by raising biogenic amine neurotransmitter levels, by either inhibiting their uptake or preventing their metabolism. No antidepressant drug to date, however, can substitute for electroconvulsive shock therapy for the treatment of severe, suicidal depression. Currently-available drugs for treating affective disorders unfortunately suffer from delayed onset of action, poor efficacy, anticholinergic effects at therapeutic doses, cardiotoxicity, convulsions and the possibility of overdosing. A large number of clinically-depressed individuals remain refractory to currently available therapies. A role for direct-acting dopamine agonists in antidepressant therapy has been suggested based on the effects observed for several dopamine agonists in various animal models (R. Muscat et aL, "Antidepressant-like effects of dopamine agonists in an animal model of depression", *Biological Psychiatry*, 31:937–946, 1992).

A role for dopamine has also been established in cognition and attention mechanisms. Animal studies support the role of dopamine in attention-related behaviors involving search and exploratory activity, distractibility, response rate, discriminability and the switching of attention. Treatment of cognitive impairment and attention deficit disorders via dopamine-based therapy has been proposed and is under active investigation (F. Levy, "The Dopamine Theory of Attention-Deficit Hyperactivity Disorder (ADHD)", in *Austrafian and New Zealand Journal of Psychiatry*, 25:277–283, 1991).

In addition, dopamine has been identified with a number of effects in the periphery, and has been used in the treatment of shock, congestive heart failure and acute renal failure. Stimulation of the peripheral D-1 receptors causes vasodilation, particularly in the renal and mesenteric vascular beds where large numbers of these receptors are found. The utility of dopamine has been limited, however, by its ability to cause vasoconstriction at higher concentrations, presumably due to its secondary effects on adrenergic receptors, and by its emetic effects due to peripheral D-2 stimulation. Agents selective for the peripheral D-1 receptors appear to offer significant advantages over treatments used currently for these and other related disorders.

Also, dopamine in combination with diuretics has been reported to reverse radio-contrast, media-induced acute renal failure in patients (Talley et al, *Clin. Res.*, 18:518, 1970), thus suggesting that dopamine agonists may be similarly useful.

A wide vadety of structures has been disclosed that are dopamine receptor ligands (H. E. Katerinopoulos and D. I. Schuster, "Structure-Activity Relationships for Dopamine Analogs: A Review", in Drugs Of The Future, Vol. 12, pp. 223–253, 1987) and include the thienopyridines, SKF 86926 (4-(3',4'-dihydroxyphenyl)-4,5,6,7-tetrahydrothieno(2,3-c)-pyridine) and SKF 86915 (7-(3',4'-dihydroxyphenyl)-4,5,6, 7-tetrahydrothieno(3,2-c)-pyridine (P. H. Andersen et al., *European Journal of Pharmacology*, 137:291–292, 1987; and U.S. Pat. Nos. 4,340,600, to L. M. Brenner and J. R. Wardell, Jr., issued 1982, and 4,282,227, to L. M. Brenner, issued 1981 ). Nichols et al. have disclosed certain substituted trans-hexahydrobenzo[a]-phenanthridine compounds as dopaminergic ligands (D. E. Nichols, U.S. Pat. No. 5,047,536, issued Sep. 10, 1991; W. K. Brewster et al.. *Journal of Medicinal Chemistry*, 33:1756–1764, 1990; and D. E. Nichols and R. R. Mailman, PCT Application WO9324462, published Dec. 9, 1993).

Although various non-hydroxylated compounds having a fused four-ring 1system have been disclosed (see, for example, Kiguchi et al., *Heterocycles*, 19:1873–7, 1982; CA 98:16897, describing various intermediates to ergot alkaloids), it is pertinent to emphasize the structural requirements for dopaminergic activity. C. Kaiser and T. Jain, "Dopamine Receptors: Functions, Subtypes and Emerging Concepts", in *Medicinal Research Reviews*, Vol. 5, pp. 145–229, 1985), have discussed the structural requirements for dopamine activity and emphasized the important effect thereupon of the placement of hydroxyl groups in candidate compounds.

D. E. Nichols (U.S. Pat. No 5,047,536, issued Sep. 10, 1991) has disclosed that dihydrexidine, which has the structure:

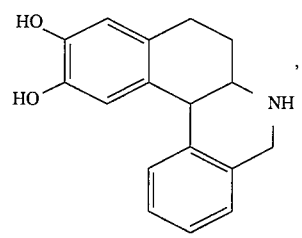

is active as a dopamine agonist, but Wei and Teitel, (*Heterocycles*, 8:97, 1979) have disclosed the related compound having the structure:

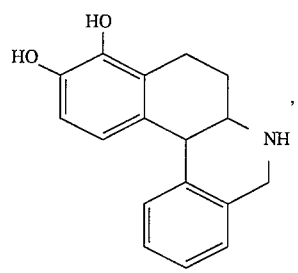

as being inactive at dopamine receptors.

The compound having the structure:

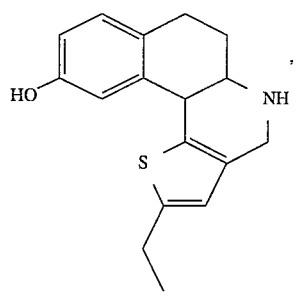

which has a single hydroxyl group on the fused phenyl ring, has been shown (see comparative Example 44, below) to have no agonist properties, but is instead a dopamine antagonist.

Applicants have discovered that compounds of the present invention have an unexpectedly narrow range of allowable substituents to the five-membered ring system therein. Comparative Examples 45–47, below, have been prepared that indicate that unlimited substitution on the novel ring system is not permissible in providing for dopamine activity, and that the nature of the substituent groups attached to the five-membered ring system of the present invention significantly alter the properties and functions of the compound (see Table 1); compounds of Examples 45–47 having D1 binding constants (Ki) of greater than 2,500 nM, having very low affinity for the dopamine D1 or D2 receptors:

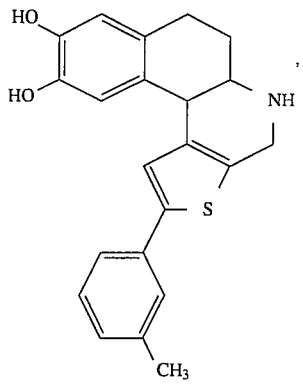
(Ex. 45)

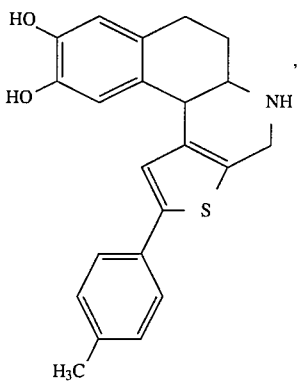
(Ex. 46)

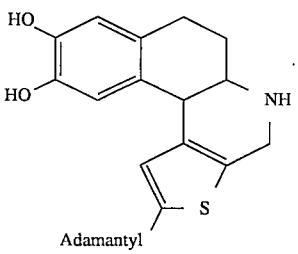
(Ex. 47)

Adamantyl

SUMMARY OF THE INVENTION

The present invention is directed to dopamine agonists of the formula:

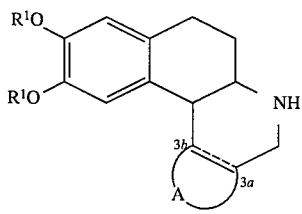

or pharmaceutically-acceptable salts, esters or carbamates thereof, wherein:

$R^1$ is hydrogen or a readily-cleavable group;

A and the atoms to which it is attached and the dotted-line optional double bond, are selected from:

(1) an unsaturated mono-heterocyclic ring selected from:

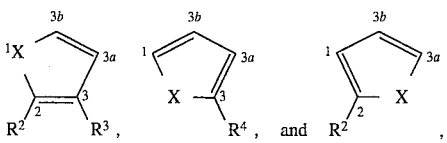

wherein
X is sulfur or oxygen,
$R^2$ is hydrogen, Cl, $CF_3$, $C_1$–$C_6$-alkyl, $C_3$–$C_7$-cycloalkyl, —$CH_2$—$C_3$—$C_5$-cycloalkyl, phenyl or thiophene;
$R^3$ is hydrogen, or when $R^2$ is hydrogen, Cl, $C_1$–$C_6$-alkyl or $CF_3$, then $R^3$ is additionally Cl, $C_1$–C5-alkyl or $CF_3$; and
$R^4$ is hydrogen, Cl, $C_1$–$C_6$-alkyl, or $C_3$-$C_7$-cycloalkyl; and (2) an unsaturated di-heterocyclic ring selected from:

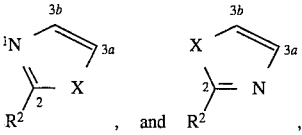

wherein X and $R^2$ are as defined above, which bind and activate dopamine receptors in the central and peripheral nervous systems and are useful in the treatment of dopamine-related neurological, psychological and cardiovascular disorders, as well as in the treatment of substance abuse and other addictive behavior disorders, cognitive impairment attention deficit disorder.

DETAILED DESCRIPTION OF THE INVENTION

This invention relates to novel tetracyclic compounds which are selective dopamine agonists having the formula (I):

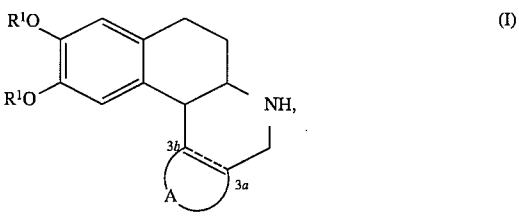

or a pharmaceutically-acceptable salt, ester or carbamate thereof, wherein:

$R^1$ is hydrogen of a readily-cieavable group, as defined below;

A and the atoms to which it is attached are selected from the group consisting of:

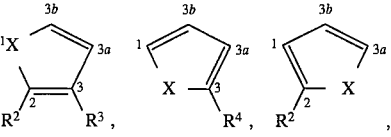

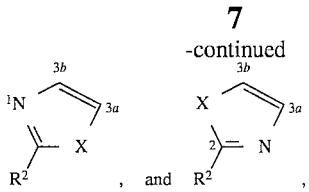

wherein:
X is sulfur or oxygen,
$R^2$ is hydrogen, Cl, $CF_3$, $C_1$–$C_6$-alkyl, as defined below, $C_3$–$C_7$-cycloalkyl, as defined below, —$CH_2$—$C_3$—$C_5$-cycloalkyl, phenyl or thiophene;
$R^3$ is hydrogen, or when $R^2$ is hydrogen, Cl, $C_1$–$C_6$-alkyl or $CF_3$, then $R^3$ is additionally Cl, $C_1$–$C_5$-alkyl or $CF_3$; and
$R^4$ is hydrogen, Cl, $C_1$–$C_6$-alkyl, or $C_3$–$C_7$-cycloalkyl.

Certain compounds of this invention may possess one or more asymmetric centers, including centers in a substituent group, such as an alkyl group, and may exist in optically-active forms. Pure d-isomers and pure l-isomers, racemic mixtures of the isomers, and mixtures thereof are intended to be within the scope of this invention. The stereochemistry at the fusion points of the saturated 6-membered rings, as shown in Formula (I), is trans, although the absolute stereochemistry may be [R] or [S], unless specifically noted otherwise. Chiral forms of certain compounds of this invention are contemplated and are specifically included within the scope of this invention.

The compounds of formula (I) have the ability to bind and activate dopamine receptors in the central and peripheral nervous systems, thus mimicking the activity of dopamine, and are therefore useful in the treatment of dopamine-related neurological, psychological and cardiovascular disorders, as well as in the treatment of substance abuse and other addictive behavior disorders, cognitive impairment and attention deficit disorder.

The present invention also relates to pharmaceutical compositions comprising a therapeutically-effective amount of the compound of formula (I) and a pharmaceutically-acceptable carrier or diluent, and methods of treating dopamine-related disorders.

Preferred compounds according to this invention are compounds of formula (I), wherein A and the atoms to which it is attached represent the ring systems:

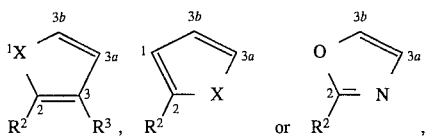

wherein $R^2$ is as defined above.

More preferred compounds according to this invention are compounds of formula (I), wherein A and the atoms to which it is attached represent a thiophene ring system, in which the arrangements of the double bonds, and the sulfur and carbon atoms is:

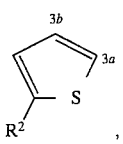

wherein $R^2$ is as defined above.

The following are representative of the compounds of Formula (I):

trans-2-Methyl-4,5,5a,6,7,11b-hexahydro-1-thia-5-aza-cyclopent-2-ena[c]-phenanthrene-9,10-diol;
trans-4,5,5a,6,7,11b-Hexahydro-2-thia-5-aza-cyclopent-3-ena[c]-phenanthrene-9,10-diol;
trans-2-Ethyl-4,5,5a,6,7,11b-hexahydro-3-thia-5-aza-cyclopent-1-ena[c]-phenanthrene-9,10-diol;
(−)-trans-2-Ethyl-4,5,5a,6,7,11b-hexahydro-3-thia-5-aza-cyclopent-1-ena[c]-phenanthrene-9,10-diol;
trans-2-Propyl-4,5,5a,6,7,11b-hexahydro-3-thia-5-aza-cyclopent-1-ena[c]-phenanthrene-9,10-diol;
trans-2-(1,1-Dimethylethyl)-4,5,5a,6,7,11b-hexahydro-3-thia-5-aza-cyclopent-1-ena[c]-phenanthrene-9,10-diol;
trans-2-(2-Propyl)-4,5,5a,6,7,11b-hexahydro-3-thia-5-aza-cyclopent-1-ena[c]-phenanthrene-9,10-diol;
trans-2-Butyl-4,5,5a,6,7,11b-hexahydro-3-thia-5-aza-cyclopent-1-ena[c]-phenanthrene-9,10-diol;
trans-2-(2-Methylpropyl)-4,5,5a,6,7,11b-hexahydro-3-thia-5-aza-cyclopent-1-ena[c]-phenanthrene-9,10-diol;
trans-2-(2,2-Dimethylpropyl)-4,5,5a,6,7,11b-hexahydro-3-thia-5-aza-cyclopent-1-ena[c]-phenanthrene-9,10-diol;
trans-2-Cyclohexyl-4,5,5a,6,7, 11b-hexahydro-3-thia-5-aza-cyclopent-1-ena[c]-phenanthrene-9,10-diol;
trans-2-Phenyl-4,5,5a,6,7,11b-hexahydro-3-thia-5-aza-cyclopent-1-ena[c]-phenanthrene-9,10-diol;
trans-2-(1,1-Dimethylethyl)-4,5,5a,6,7,11b-hexahydro-1-thia-5-aza-cyclopent-2ena[c]-phenanthrene-9,10-diol;
trans-2-Ethyl-4,5,5a,6,7,11b-hexahydro-1-thia-5-aza-cyclopent-2-ena[c]-phenanthrene-9,10-diol;
trans-2-Propyl-4,5,5a,6,7,11b-hexahydro-1 -thia-5-aza-cyclopent-2-ena[c]-phenanthrene-9,10-diol;
trans-2-Butyl-4,5,5a,6,7,11b-hexahydro-1-thia-5-aza-cyclopent-2-ena[c]-phenanthrene-9,10-diol; trans-2-Cyclohexyl-4,5,5a,6,7,11b-hexahydro-1-thia-5-aza-cyclopent-2-ena[c]-phenanthrene-9,10-diol;
trans-4,5,5a,6,7,11b-Hexahydro-1-thia-5-aza-cyclopent-2-ena[c]-phenanthrene-9,10-diol;
trans-2-Phenyl-4,5,5a,6,7,11b-hexahydro-1-thia-5-aza-cyclopent-2-ena[c]-phenanthrene-9,10-diol;
(−)-trans-2-Propyl-4,5,5a,6,7,11b-hexahydro-3-thia-5-aza-cyclopent-1-ena[c]-phenanthrene-9,10-diol;
trans-2,3-Dimethyl-4,5,5a,6,7,11b-hexahydro-1-thia-5-aza-cyclopent-2-ena[c]-phenanthrene-9,10-diol;
trans-2-Methyl-4,5,5a,6,7,11b-hexahydro-3-thia-5-aza-cyclopent-1-ena[c]-phenanthrene-9,10-diol;
(−)-trans-2-Methyl-4,5,5a,6,7,11b-hexahydro-3-thia-5-aza-cyclopent-1-ena[c]-phenanthrene-9,10-diol;
(−)-trans-2-(1,1-Dimethylethyl)-4,5,5a,6,7,11b-hexahydro-3-thia-5-aza-cyclopent-1-ena[c]-phenanthrene-9,10-diol;
trans-4,5,5a,6,7,11b-Hexahydro-3-thia-5-aza-cyclopent-1-ena[c]-phenanthrene-9,10-diol;
trans-2-Trifluoromethyl-4,5,5a,6,7,11b-hexahydro-3-thia-5-aza-cyclopent-1-ena[c]-phenanthrene-9,10-diol;
trans-2-Propyl-4,5,5a,6,7,11b-hexahydro-1 -thia-3,5-diaza-cyclopent-2-ena[c]phenanthrene-9,10-diol;
trans-2-Propyl-4,5,5a,6,7, 11b-hexahydro-3-thia- 1,5-diaza-cyclopent-1-ena[c]-phenanthrene-9,10-diol;
trans-2-Propyl-4,5,5a,6,7,11b-hexahydro-1-oxa-3,5-diaza-cyclopent-2-ena[c]-phenanthrene-9,10-diol;
trans-2-(3-Methylbutyl)-4,5,5a,6,7,11b-hexahydro-1-thia-5-aza-cyclopent-2-ena[c]-phenanthrene-9,10-diol;
trans-2-Hexyl-4,5,5a,6,7,11b-hexahydro-1-thia-5-aza-cyclopent-2-ena[c]-phenanthrene-9,10-diol;
trans-2-Chloro-4,5,5a,6,7,11b-hexahydro-1-thia-5-aza-cyclopent-2-ena[c]-phenanthrene-9,10-diol;
trans-2-(1-Cyclopentylmethyl)-4,5,5a,6,7,11b-hexahydro-1-thia-5-aza-cyclopent-2-ena[c]-phenanthrene-9,10-diol;
trans-2-Isopropyl-4,5,5a,6,7,11b-hexahydro-1-thia-5-aza-cyclopent-2-ena[c]-phenanthrene-9,10-diol;

trans-2-(3-Methylbutyl)-4,5,5a,6,7,11b-hexahydro-3-thia-5-aza-cyclopent-1-ena[c]-phenanthrene-9,10-diol;

trans-2-Pentyl-4,5,5a,6,7,11b-hexahydro-3-thia-5-aza-cyclopent-1-ena[c]phenanthrene-9,10-diol;

trans-2-(2-Thiophenyl)-4,5,5a,6,7, 11b-hexahydro-3-thia-5-aza-cyclopent-1-ena[c]phenanthrene-diol;

trans-2-Hexyl-4,5,5a,6,7,11b-hexahydro-3-thia-5-aza-cyclopent-1-ena[c]phenanthrene-9,10-diol;

trans-2-(Cyclopentylmethyl)-4,5,5a,6,7,11b-hexahydro-3-thia-5-aza-cyclopent-1-ena[c]phenanthrene-9,10-diol;

trans-2-Ethyl-4,5,5a,6,7,11b-hexahydro-3-oxa-5-aza-cyclopent-1-ena[c]phenanthrene-9,10-diol;

trans-2-Propyl-4,5,5a,6,7,11b-hexahydro-3-oxa-5-aza-cyclopent-1-ena[c]phenanthrene-9,10-diol;

trans-2-Phenyl-4,5,5a,6,7,11b-hexahydro-3-oxa-5-aza-cyclopent-1-ena[c]phenanthrene-9,10-diol;

trans-3-Propyl-4,5,5a,6,7,11b-hexahydro-2-thia-5-aza-cyclopent-3-ena[c]phenanthrene-9,10-diol; and (−)-trans-9,10-Diacetyloxy-2-propyl-4,5,5a,6,7,11b-hexahydro-3-thia-5-azacyclopent-1-ena[c]phenanthrene;

trans-2-Chloro-4,5,5a,6,7,11b-hexahydro-3-thia-5-aza-cyclopent-1-ena[c]phenanthrene-9,10-diol;

trans-2-Isopropyl-4,5,5a,6,7,11b-hexahydro-1-oxa-3,5-diaza-cyclopent-2-ena[c]phenanthrene-9,10-diol;

trans-2-Methyl-4,5,5a,6,7,11b-hexahydro-1-oxa-3,5-diaza-cyclopent-2-ena[c]phenanthrene-9,10-diol;

trans-3-Propyl-4,5,5a,6,7,11b-hexahydro-1-thia-5-aza-cyclopent-2-ena[c]phenanthrene-9,10-diol; trans-2-Propyl-4,5,5a,6,7,11b-hexahydro- 1,5-diaza-3-oxa-cyclopent- 1 ena[c]phenanthrene-9,10-diol;

trans-2-Propyl-4,5,5a,6,7,11b-hexahydro- 1,5-diaza-3-thia-cyclopent-1-ena[c]phenanthrene-9,10-diol;

trans-2-Ethyl-4,5,5a,6,7,11b-hexahydro-1-oxa-5-aza-cyclopent-2-ena[c]phenanthrene-9,10-diol; and trans-2-Trifluoromethyl-4,5,5a,6,7, 11b-hexahydro-1-thia-3,5-diaza-cyclopent-2- ena[c]phenanthrene-9,10-diol;

or a pharmaceutically-acceptable salt, ester or carbamate thereof.

The following are representative of the more preferred compounds of Formula (I):

trans-2-Ethyl-4,5,5a,6,7,11b-hexahydro-3-thia-5-aza-cyclopent-1-ena[c]phenanthrene-9,10-diol;

(−)-trans-2-Ethyl-4,5,5a,6,7,11b-hexahydro-3-thia-5-azacyclopent-1-ena[c]phenanthrene-9,10-diol;

5 trans-2-Propyl-4,5,5a,6,7,11b-hexahydro-3-thia-5-aza-cyclopent-1-ena[c]phenanthrene-9,10-diol;

trans-2-(1,1 -Dimethylethyl)-4,5,5a,6,7, 11b-hexahydro-3-thia-5-aza-cyclopent-1-ena[c]-phenanthrene-9,10-diol;

trans-2-Butyl-4,5,5a,6,7,11b-hexahydro-3-thia-5-aza-cyclopent-1-ena[c]phenanthrene-9,10-diol;

(−)-trans-2-Propyl-4,5,5a,6,7,11b-hexahydro-3-thia-5-aza-cyclopent-1-ena[c]phenanthrene-9,10-diol;

trans-2-Methyl-4,5,5a,6,7,11b-hexahydro-3-thia-5-aza-cyclopent-1-ena[c]phenanthrene-9,10-diol;

(−)-trans-2-Methyl-4,5,5a,6,7,11b-hexahydro-3-thia-5-aza-cyclopent-1-ena[c]phenanthrene-9,10-diol;

(−)-trans-2-(1,1 -Dimethylethyl)-4,5,5a,6,7,11b-hexahydro-3-thia-5-aza-cyclopent-1-ena[c]-phenanthrene-9,10-diol;

trans-2-Propyl-4,5,5a,6,7,11b-hexahydro-1-oxa-3,5-diaza-cyclopent-2-ena[c]phenanthrene-9,10-diol;

trans-2-Ethyl-4,5,5a,6,7,11b-hexahydro-3-oxa-5-aza-cyclopent-1-ena[c]phenanthrene-9,10-diol;

trans-2-Propyl-4,5,5a,6,7,11b-hexahydro-3-oxa-5-aza-cyclopent-1-ena[c]phenanthrene-9,10-diol;

(−)-trans-9,10-Diacetyloxy-2-propyl-4,5,5a,6,7,11b-hexahydro-3-thia-5-aza-cyclopent-1-ena[c]phenanthrene;

trans-2-Chloro-4,5,5a,6,7,11b-hexahydro-3-thia-5-aza-cyclopent-1-ena[c]phenanthrene-9,10-diol; and trans-2-Methyl-4,5,5a,6,7,11b-hexahydro-1-oxa-3,5-diaza-cyclopent-2-ena[c]phenanthrene-9,10-diol;

or a pharmaceutically-acceptable salt, ester or carbamate thereof.

The following are representative of the especially preferred compounds of Formula (I):

trans-2-Ethyl-4,5,5a,6,7,11b-hexahydro-3-thia-5-aza-cyclopent-1-ena[c]phenanthrene-9,10-diol;

(−)-trans-2-Ethyl-4,5,5a,6,7,11b-hexahydro-3-thia-5-aza-cyclopent-1-ena[c]phenanthrene-9,10-diol;

trans-2-Propyl-4,5,5a,6,7,11b-hexahydro-3-thia-5-aza-cyclopent-1-ena[c]phenanthrene-9,10-diol;

trans-2-(1,1 -Dimethylethyl)-4,5,5a,6,7,11b-hexahydro-3-thia-5-aza-cyclopent-1-ena[c]-phenanthrene-9,10-diol;

trans-2-Butyl-4,5,5a,6,7,11b-hexahydro-3-thia-5-aza-cyclopent-1-ena[c]phenanthrene-9,10-diol;

(−)-trans-2-Propyl-4,5,5a,6,7,11b-hexahydro-3-thia-5-aza-cyclopent-1-ena[c]phenanthrene-9,10-diol;

trans-2-Methyl-4,5,5a,6,7,11b-hexahydro-3-thia-5-aza-cyclopent-1-ena[c]phenanthrene-9,10-diol;

(−)-trans-2-Methyl-4,5,5a,6,7,11b-hexahydro-3-thia-5-aza-cyclopent-1-ena[c]phenanthrene-9,10-diol;

(−)-trans-2-(1,1 -Dimethylethyl)-4,5,5a,6,7,11b-hexahydro-3-thia-5-aza-cyclopent-1-ena[c]-phenanthrene-9,10-diol; and (−)-trans-9,10-Diacetyloxy-2-propyl-4,5,5a,6,7,11b-hexahydro-3-thia-5-aza-cyclopent-1-ena[c]phenanthrene;

or a pharmaceutically-acceptable salt, ester or carbamate thereof.

"$C_1$–$C_5$-" or "$C_1$–$C_6$-alkyl" means a straight- or branched-chain hydrocarbon radical containing from one-to-five or from one-to-six carbon atoms, as indicated, including as appropriate, for example, methyl, ethyl, n-propyl, i-propyl, n-butyl, sec-butyl, i-butyl, t-butyl, pentyl, hexyl, and the like.

"$C_3$–$C_7$-" or "$C_3$–$C_5$-cycloalkyl" means a cyclic hydrocarbon ring containing from three-to-seven carbon atoms or from three-to-five carbon atoms, including, for example, as appropriate, cyclopropyl, cyclobutyl, cyclopentyl, cyclohexyl or cycloheptyl.

"Readily-cleavable group", as used herein, means substituents which are readily cleaved in vivo, for example, by hydrolysis in blood or tissue, to yield the compound of Formula (I) wherein $R^1$ is hydrogen. Readily-cleavable groups include those substituents commonly referred to as "prodrug moieties", see, e.g., T. Higuchi and V. Stella who provide a thorough discussion of the prodrug concept in Pro-drugs as Novel Delivery Systems, Vol. 14 of the A.C.S. Symposium Series, American Chemical Society (1975). Examples of readilycleavable groups include acetyl, trimethylacetyl, butanoyl, methyl succinoyl, tbutyl succinoyl, ethoxycarbonyl, methoxycarbonyl, benzoyl, 3-aminocyclohexylidenyl, and the like.

The term "administration" of the dopaminergic agent or composition, as used herein, refers to systemic use, as when taken orally, parenterally, by inhalation spray, by nasal, rectal or buccal routes, or topically in dosage form unit formulations containing conventional nontoxic pharmaceutically-acceptable carriers, adjuvants and vehicles, as desired.

The term "parenteral", as used herein, includes intravenous, intramuscular, intraperitoneal, intrasternal, subcutaneous and intraarticular injection and infusion techniques.

By "pharmaceutically-acceptable" is meant those salts, esters and carbamates which are, within the scope of sound medical judgment, suitable for use in contact with the tissues of humans and lower animals without undue toxicity, irritation, allergic response and the like, and are commensurate with a reasonable benefit/risk ratio, effective for their intended use in the treatment of psychological, neurological, cardiovascular and addictive behavior disorders. Pharmaceutically-acceptable salts are well known in the art, as exemplified, for example, by S. M. Berge et al., who describe pharmaceutically-acceptable salts in detail in *J. Pharm. Sci.*, 66: 1–19, 1977. The salts may be prepared in situ during the final isolation and purification of the compounds of Formula (I), or separately by reacting the free base function with a suitable organic acid. Representative acid-addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts, and the like. Representative alkali or alkaline earth metal salts include sodium, calcium, potassium, magnesium salts, and the like. Examples of pharmaceutically-acceptable, nontoxic carbamates of the compounds of Formula I include carbamates derived from the phenolic groups (R'NHCO-phenol) or the ring nitrogen atom ring (—N—CO—O—R") wherein R' and R" may be $C_1$–$C_6$- alkyl groups, which may be straight- or branched-chain, or aromatic groups or heterocyclic residues. Carbamates of the compounds of Formula I may be prepared according to conventional methods.

As used herein, the term "pharmaceutically-acceptable carriers" means a non-toxic, inert solid, semi-solid or liquid filler, diluent, encapsulating material or formulation auxiliary of any type. Some examples of the materials that can serve as pharmaceutically-acceptable carriers are sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants, such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically-acceptable antioxidants include water-soluble antioxidants, such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents, such as citric acid, ethylenediamine tetraacetic acid (EDTA), sorbitol, tartaric acid, phosphoric acid and the like.

By a "therapeutically-effective amount" of a dopaminergic agent is meant a sufficient amount of the compound to treat dopamine-related disorders at a reasonable benefit/risk ratio applicable to any medical treatment. It will be understood, however, that the total daily usage of the compounds and compositions of the present invention will be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient; the time of administration, route of administration, and rate of excretion of the specific compound employed; the duration of the treatment; drugs used in combination or coincidentally with the specific compound employed; and like factors well known in the medical arts.

The term "affective disorder" as used herein refers to disorders that are characterized by changes in mood as the primary clinical manifestation, for example, depression.

The term "antipsychotic agent", as used herein, refers to drugs used extensively in the symptomatic management of all forms of schizophrenia, organic psychosis, the manic phase of manic depressive illness and other acute idiopathic illnesses, and occasionally used in the treatment of depression or in severe anxiety.

The term "attention deficit disorder" refers to a recently-classified pediatric neuropsychiatric disorder characterized by inattention, impulsivity, distractibility and sometimes hyperactivity, which replaces the less formal diagnoses of hyperactivity syndrome, hyperkinetic syndrome, minimal brain dysfunction and specific learning disability. The disorder is prevalent among pre-adolescent children and is reflected in poor school performance and social behavior and has been described in experimental reports of impaired perceptual, cognitive and motor function.

The term "cognitive impairment" refers to a deficiency in any of the aspects of the cognitive (information processing) functions of perceiving, thinking and remembering.

The term "dopamine-related cardiovascular disorders", as used herein, refers to conditions which can be reversed or improved by administration of dopamine or a dopaminergic agent, either alone or in combination therapy with other classes of cardiovascular agents. The usefulness of dopaminergic agents in cardiovascular diseases, for example in the treatment of shock and congestive heart failure, is based on the known, but incompletely understood, role of dopamine in the cardiovascular system, especially the effects of dopamine on the heart and the ability of dopamine to produce vasoconstriction while maintaining blood flow through renal and mesenteric beds. Also included are other related, potential uses for dopaminergic agents which include, for example, use in renal failure.

The term "dopamine-related neurological and psychological disorders", as used herein, refers to behavioral disorders, such as psychoses and addictive behavior disorders; affective disorders, such as major depression; and movement disorders, such as Parkinson's disease, Huntington's disease and Gilles de la Tourette's syndrome; which have been linked, pharmacologically and/or clinically, to either insufficient or excessive functional dopaminergic activity in the CNS. Also included are miscellaneous indications for which dopaminergic agents have been found to be clinically useful. Examples of such indications include disorders characterized by vomiting, such as uremia, gastroenteritis, carcinomatosis, radiation sickness, and emesis caused by a variety of drugs, intractable hiccough and alcoholic hallucinosis.

"Normal dopamine levels" are those levels of dopamine that are found in the brains of control subjects and are usually measured as levels of the dopamine metabolites homovanillic acid (3-methoxy-4-hydroxyphenylacetic acid) and 3,4-dihydroxyphenylacetic acid. Abnormal dopamine levels are those levels that are not within the range of dopamine levels found in the brains of control subjects.

The term "substance abuse", as used herein, refers to periodic or regular self-administration of psychoactive substances in the absence of medical indications and despite the presence of persistent or recurrent social, occupational, psychological or physical problems that the person knows are caused by or may be exacerbated by continued use of the substance.

The total daily dose of the compounds of this invention administered to a host in single or in divided doses may be in amounts, for example, from 0.01 to 50 mg/kg body weight or more, usually from 0.1 to 30 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose.

The compounds of the present invention may be administered alone or in combination or in concurrent therapy with other agents which effect the dopaminergic system, for example, L-dopa, amantadine, apomorphine or bromocryptine; and with cholinergic agents, for example, benztropine, biperiden, ethopromazine, procyclidine, trihexylphenidyl, and the like. The compounds of the present invention may also be co-administered with agents, for example, enzyme inhibitors, which block their metabolic transformation outside the CNS.

This invention also provides pharmaceutical compositions in unit dosage forms, comprising a therapeutically-effective amount of a compound (or compounds) of this invention in combination with a conventional pharmaceutical carrier.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally-acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil may be employed, including synthetic mono- or diglycerides. Also, fatty acids, such as oleic acid, are used in the preparation of injectables.

The injectable formulation may be sterilized, for example, by filtration through a bacteria-retaining filter, or by incorporating sterilizing agents in the form of sterile solid compositions which may be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of the drug in a crystalline or amorphous material which has poor water solubility The rate of absorption of the drug becomes dependent on the rate of dissolution of the drug which is, in turn, dependent on the physical state of the drug, for example, the crystal size of the drug and its crystalline form. Another approach to delaying absorption of a drug is to administer the drug as a solution or suspension in oil. Injectable depot forms may also be made by forming microcapsule matrices of drugs and biodegradable polymers, such as with polylactide-polyglycolide. Depending on the ratio of drug to polymer and the composition of the polymer, the rate of drug release may be controlled by this method. Examples of other biodegradable polymers include poly-orthoesters and polyanhydrides. The depot injectables can also be made by entrapping the drug in liposomes or microemulsions which are compatible with body tissues.

Suppositories for rectal administration of the drug may be prepared by mixing the drug with a suitable non-irritating excipient, such as cocoa butter and polyethylene glycol, both of which are solid at ordinary temperature, but liquid at the rectal temperature and will therefore melt in the rectum, releasing the drug.

Solid dosage forms for oral administration may include capsules, tablets, pills, powders, prills and granules. In such solid dosage forms the active compound may be admixed with at least one inert diluent, such as sucrose, lactose or starch, such dosage forms may also comprise, as is normal practice, additional substances other than inert diluents, e.g., tableting lubricants and other tableting aids, such as magnesium stearate and microcrystalline cellulose. In the case of capsules, tablets and pills, the dosage forms may also comprise buffering agents. Tablets and pills may additionally be prepared with enteric coatings and other release-controlling coatings.

Solid compositions of a similar type may also be employed as fillers in soft and hard-filled gelatin capsules using such excipients as lactose or milk sugar, as well as high molecular weight polyethylene glycols and the like.

Liquid dosage forms for oral administration may include pharmaceutically-acceptable emulsions, microemulsions, solutions, suspensions, syrups and elixirs containing inert diluents commonly used in the art, such as water, and may also comprise adjuvants, such as wetting agents; emulsifying and suspending agents; sweetening, flavoring and perfuming agents.

If desired, the compounds of the present invention can be incorporated into slow release or targeted-delivery systems, such as polymer matrices, liposomes and microspheres.

The active compounds may also be in micro-encapsulated form with one or more excipients, as noted above. The solid dosage forms of tablets, dragees, capsules, pills, and granules may be prepared with coatings and shells, such as enteric coatings and other coatings well-known in the pharmaceutical formulating art. They may optionally contain opacifying agents, and may also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or transdermal patches. The active component is admixed under sterile conditions with a pharmaceutically-acceptable carrier and any needed preservatives or buffers, as required. Ophthalmic formulations, ear drops, eye ointments, powders and solutions are also contemplated as being within the scope of this invention. Administration sublingually, from one or more of the above dosage forms, is also contemplated as a suitable mode of administration of the compounds of the invention.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds of this invention, excipients, such as lactose, talc, silicic acid, aluminum hydroxide, calcium silicates and polyamide powder, or mixtures of these substances. Sprays may additionally contain customary propellants, such as chlorofluorohydrocarbons or environmentally- and pharmaceutically-acceptable substitutes.

Transdermal patches have the added advantage of providing controlled delivery of a compound to the body. Such dosage forms may be made by dissolving or dispersing the compound in the proper medium. Absorption enhancers may also be used to increase the flux of the compound across the skin. The rate may be controlled by either providing a rate-controlling membrane or by dispersing the compound in a polymer matrix or gel.

Synthetic Methods

In general, the compounds of this invention are synthesized by reaction schemes 1 through 12 as illustrated below. It should be understood that $R^2$–$R^4$, as used herein, correspond to these like-numbered R groups identified by Formula (I). The oxygens of the catechol groups may be derivatized with "protecting groups" (Q), which are known in the art and may be prepared by conventional methods. These derivatizing groups may be selected from among phenol derivatives and derivatives which are suitable to catechols because of the proximity of the two hydroxyl functions. Commonly-used phenol derivatives are ethers, for example alkyl, alkenyl, and cycloalkyl ethers (such as methyl, isopropyl, t-butyl, cyclopropylmethyl, cyclohexyl, allyl ethers, and the like); alkoxyalkyl ethers, such as methoxymethyl or methoxyethoxymethyl ether and the like; alkylthioalkyl ethers, such as methylthiomethyl ether; tetrahydropyranyl ethers, arylalkyl ethers (such as benzyl, o-nitrobenzyl, 9-anthrylmethyl, 4-picolyl ethers and the like); trialkylsilyl ethers, such as trimethylsilyl, triethylsilyl, tbutyldimethylsilyl ethers, and the like; alkyl esters, such as acetates, propionates, n-butyrates, isobutyrates, trimethylacetates, benzoates, and the like; substituted alkyl esters, such as 3-(methoxycarbonyl)propionate, 3-aminopropionate, 3-(t-butoxycarbonyl)-propionate, and the like; carbonates, such as methyl ethyl, 2,2,2-trichloroethyl, vinyl, benzyl, and the like; carbamates, such as methyl, isobutyl, phenyl, benzyl, dimethyl, and the like; and sulfonates, such as methanesulfonate, trifluoromethanesulfonate, toluenesulfonate, and the like. Commonly used catechol derivatives include cyclic acetals and ketals, such as methylene acetal, acetonide derivatives, cyclohexylidene ketal, diphenylmethylene ketal, and the like, cyclic esters, such as borate esters, cyclic carbonate esters, and the like. Other hydroxyl-protecting groups (P) may be selected by one skilled in the art as suitable for protecting non-phenol hydroxyl groups.

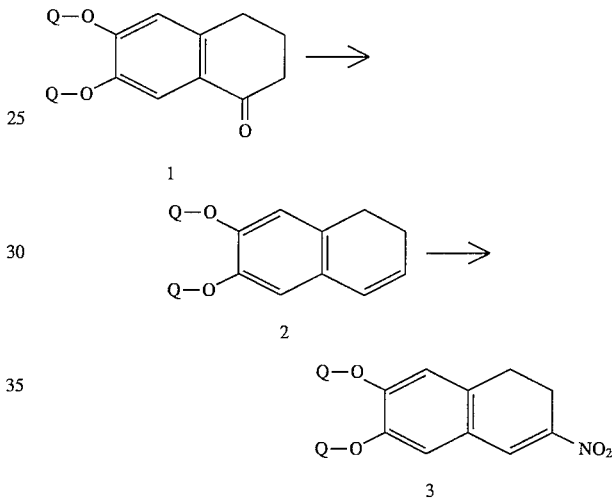

Scheme 1

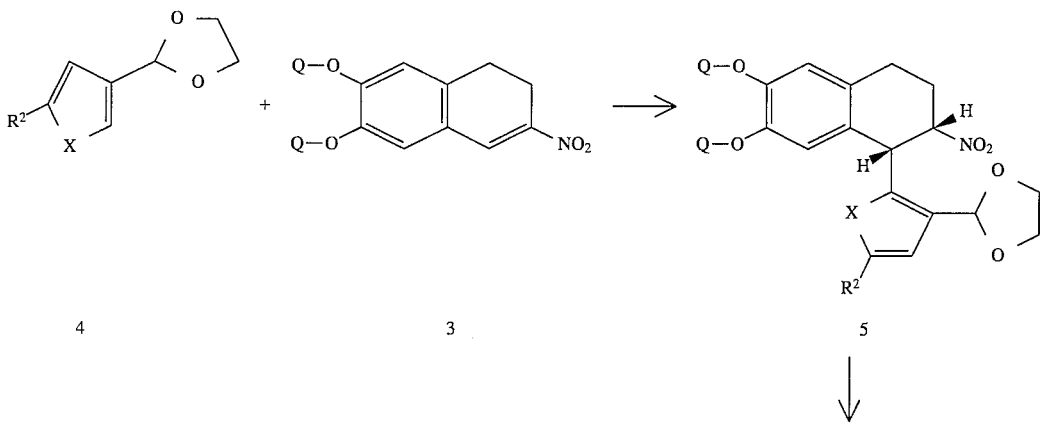

Scheme 2

-continued
Scheme 2

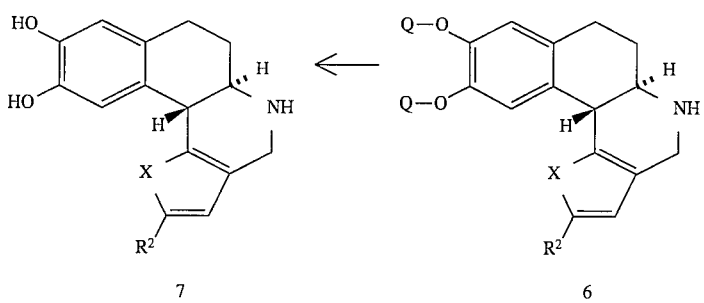

In accordance with Scheme 1, a diprotected 6,7-dihydroxy-1-tetralone derivative of formula 1 is reduced with a suitable agent, such as sodium borohydride, lithium aluminum hydride, various other hydride reducing agents, and the like, in a suitable solvent, and the intermediate alcohol thus formed is not isolated, but is dehydrated in the presence of an acid catalyst, such as p-toluenesulfonic acid or the like, to give the protected dihydronaphthalene derivative of formula 2. The compound of formula 2 is reacted with a nitrating agent, such as tetranitromethane, in the presence of a base, such as pyridine in a suitable organic solvent, such as acetone or the like, to give the protected 3-nitro-dihydronaphthalene derivative of formula 3.

In accordance with Scheme 2, the compound of formula 5 is prepared by first preparing the anion of an acetal-protected derivative of a 5-substituted-3carboxaldehyde compound of formula 4, wherein X and $R^2$ are as defined above, by reacting the compound 4 with a strong base, such as butyllithium, for example, under an inert atmosphere, such as nitrogen or argon, for example, and at a temperature of about 0° C. to –78° C. for 1–3 hours. This metallo-organic salt is then condensed with the 3-nitro-dihydronaphthalene derivative of formula 3 in a suitable organic solvent under an inert atmosphere, such as nitrogen or argon, for example, and at a temperature of about 0° C. to –78° C. for 1–4 hours, followed by quenching of the reaction with aqueous NH$_4$Cl followed by equilibration of the reaction product with a catalytic amount of base, such as triethylamine in a solvent, such as acetonitrile to give the trans isomer of compound 5. Compound 5 is converted to compound 6 by reaction conditions which simultaneously reduce the nitro-group to an amino-group, liberate the aldehyde group from its protecting acetal, and thus promote internal condensation of the amino and aldehyde groups and subsequent reduction by reaction with zinc dust in dilute acid, such as aqueous acetic acid, for example, at a temperature from ambient to about 80° C. for 0.1–2 hours. The protecting groups of compound 6 are removed by reacting the compound with a reagent suitable for removal of phenol protecting groups, such as, for example, BBr3 or BCl$_3$, in an inert solvent, such as methylene chloride, as is well known in the art, followed by isolation of the 1-thiaor 1-oxa-5-aza-cyclopent-2-ena[c] phenanthrene compound of formula 7.

Scheme 3

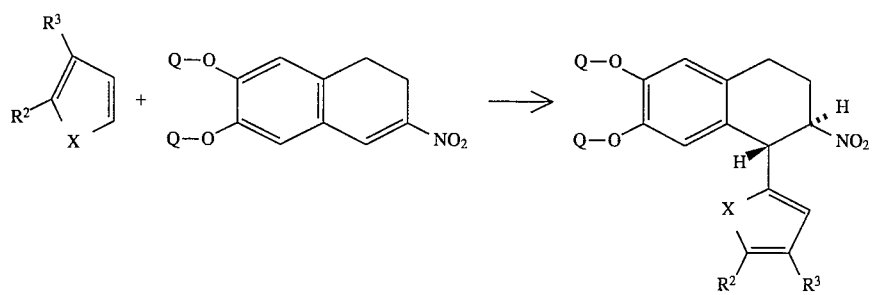

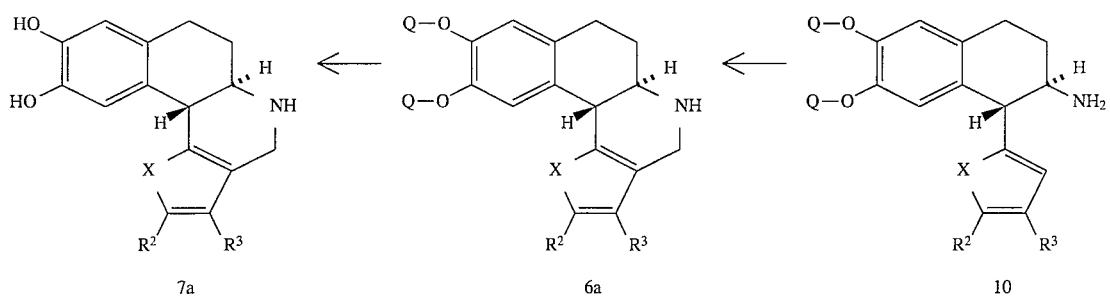

As alternate means of preparing the compounds of formula 7, in accordance with Scheme 3, a mono- or di-substituted thiophene or furan compound of formula 8, wherein X is O or S and $R^2$ and $R^3$ are as defined above, is reacted with a strong base, such as butyllithium, for example, under an inert atmosphere, such as nitrogen or argon, for example, and at a temperature of about ambient to −78° C. for 1–4 hours. The metallo-organic derivative of compound 8 is then condensed with the 3-nitro-dihydro-naphthalene derivative of formula 3 under the conditions described for Scheme 2 above, to form the compound 9.

amino compound 10 is isolated. In a condensation reaction, compound 10 is reacted in the presence of base, such as alcoholic potassium carbonate, with paraformaldehyde at ambient temperature for 8–24 hours, and the solvents are removed. The residue is stirred in a strong acid, such as tdfluoroacetic acid, for example, for 1–4 hours at ambient temperature, and the product 6a is isolated. Compound 6a is converted into compound 7a by the procedure described for Scheme 2 above.

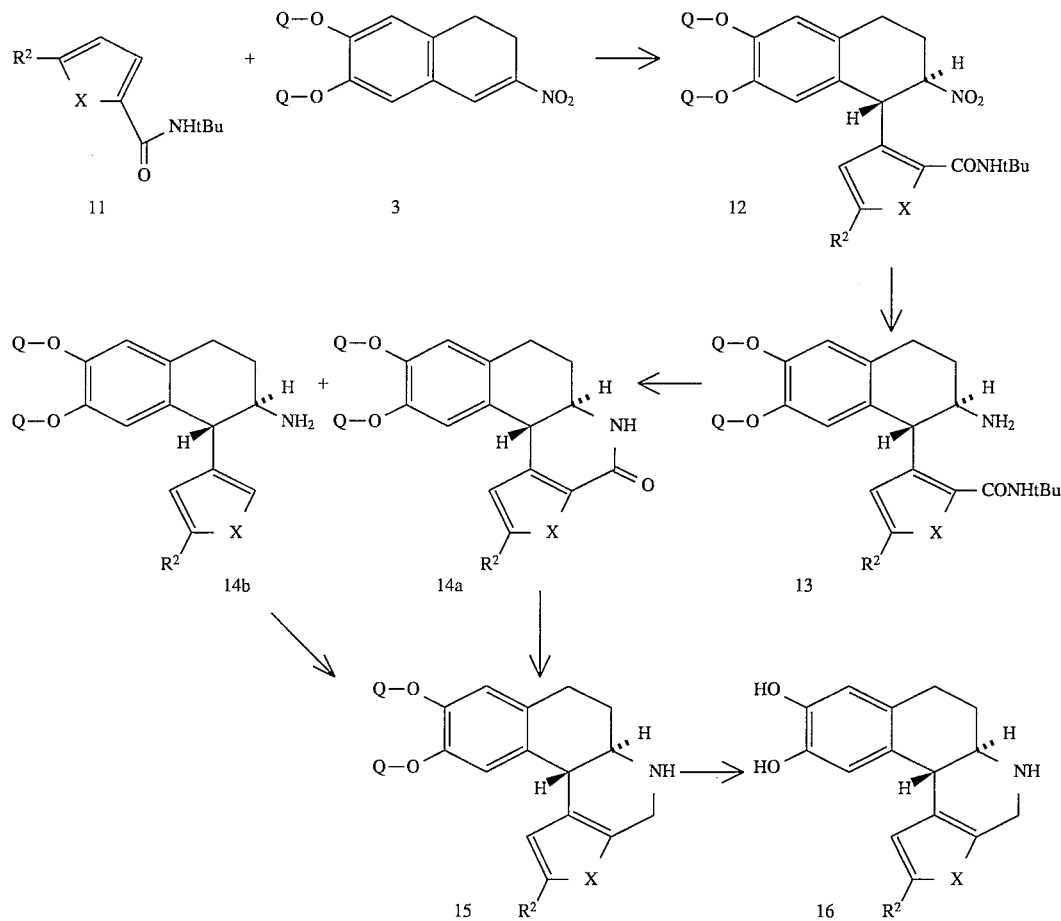

Compound 9 is reacted with zinc dust in strong acid, such as 6 N HCl, at ambient temperature for 0.5–2 hours, and the In accordance with Scheme 4, the N-t-butylamide of the thiophene- or furan-2-carboxylic acid of formula 11, wherein X is O or S and $R^2$ is as described above, is reacted with a strong base, such as n-butyllithium, as described in Scheme 2 above and condensed with the 3-nitro-dihydro-naphthalene derivative of formula 3 under the conditions described for Scheme 2 above, to form the compound 12. Compound 12 is reduced with zinc dust in HCl as described above to give the corresponding amino compound 13, which is then heated with acid, such as 10% sulfuric acid or toluenesulfonic acid in refluxing toluene, for example, to give a mixture of compounds 14a and 14b. Compound 14a is then reduced with a suitable reducing agent, such as $BH_3$ or lithium aluminum hydride in a suitable solvent, such as THF or ether, for example, to give the compound 15. Compound 14b is reacted with paraformaldehyde in an organic solvent, such as ethanol or methanol, in the presence of acid, such as 20% HCl, for 1–4 hours at a temperature from ambient to reflux to perform the internal dng closure (Pictet-Spengler cyclization) and give compound 15. Compound 15 is converted into compound 16 by the procedure described for converting compound 6 into compound 7 in Scheme 2 above.

Scheme 5

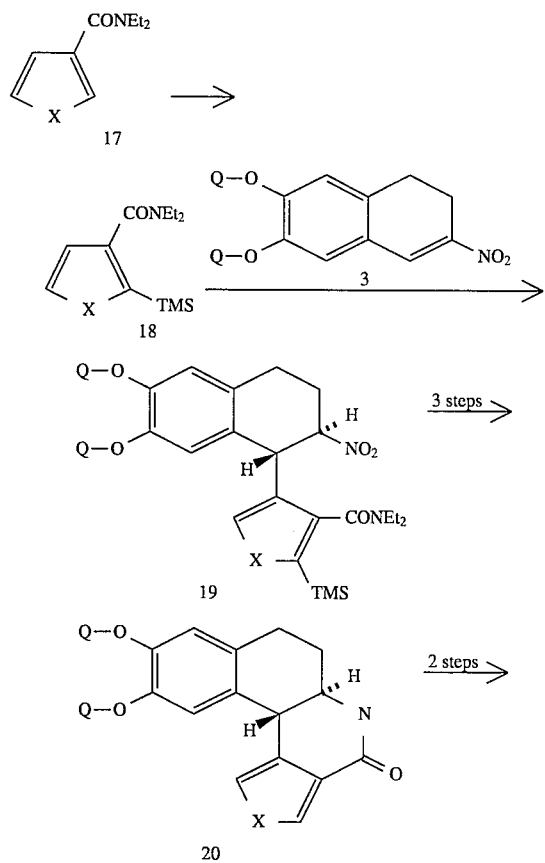

-continued
Scheme 5

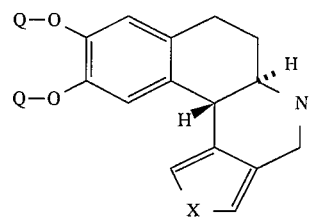

In accordance with Scheme 5, the N,N-diethylamide of thiophene- or furan-3-carboxylic acid of formula 17, wherein X is S or O, is reacted under nitrogen at −78° C. with N,N,N',N'-tetramethyldiaminomethane (TMEDA) and 2-butyl lithium in a suitable solvent, such as cyclohexane, THF or ether, for example, for 1–2 hours, followed by addition of chlorotrimethylsilane with stirring for 1–2 hours, to give the di-substituted thiophene of formula 18. Compound 18 is reacted with a strong base, such as 2-butyl-lithium in the presence of an additive, such as TMEDA, as described in Scheme 2 above and condensed with the 3-nitro-dihydro-naphthalene derivative of formula 3 under the conditions described for Scheme 2 above, to form the compound 19. Compound 19 is reduced to the corresponding amine as described in previous schemes and cyclized in the presence of a Lewis acid, such as tdmethylaluminum, then the tdmethylsilyl group is completely removed under acidic conditions to give compound 20. Compound 20 is reduced in a manner similar to the reduction of compound 14a in Scheme 4 above, and deprotected by the procedure described for converting compound 6 into compound 7 in Scheme 2 above.

Scheme 6

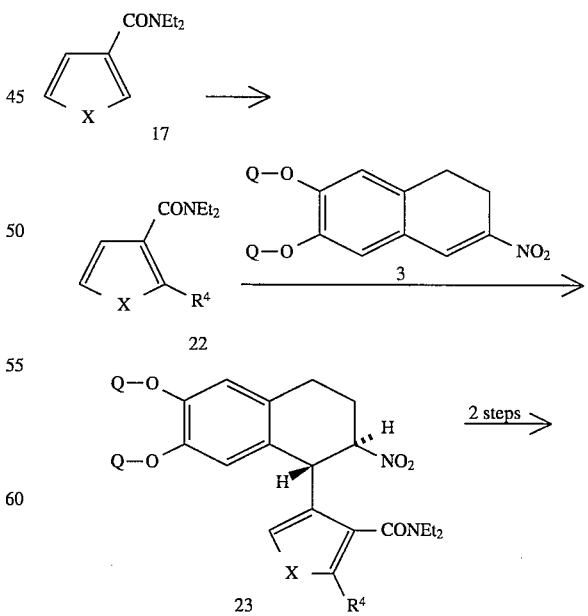

-continued
Scheme 6

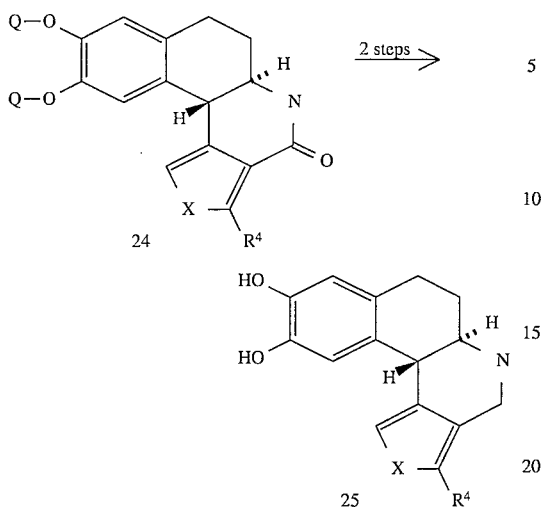

ethyl bromide, or the like, or an appropriate chlorinating agent, such as N-chlorosuccinimide, with the anion of compound 17, prepared as described above. It should be understood that the N,N-diethylamide group of compound 17 may be replaced by other substituted amide groups of equal bulk, such as other alkyl groups or cyclic amide groups, as will be readily apparent to those skilled in the art. Compound 22 is then reacted with compound 3 by the method described above, and the compound 23 is reduced to the corresponding amine and cyclized to give compound 24 in the presence of protic or Lewis acids as discussed in Scheme 5, and compound 24 is carried forward to the final compound 25 by a reaction similar to that described in Scheme 4 above.

In accordance with Scheme 6, and as an alternate procedure similar to Scheme 5, wherein the trimethylsilyl compound is prepared, the compound 22, wherein X is S or O, and $R^4$ is as defined above, is prepared by reacting an appropriate organo-halide compound, such as methyl iodide,

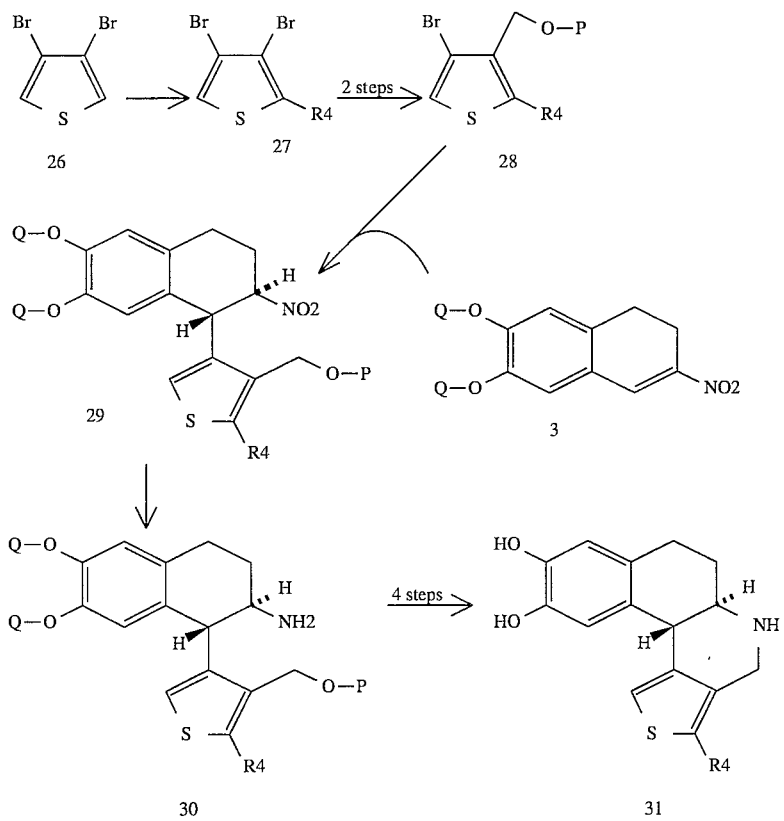

In accordance with Scheme 7, which may be used as an alternate procedure to Scheme 6, the compound 26 is reacted with a base such as lithium diisopropyl amide and an appropriate organo-halide compound, such as methyl iodide, propyl iodide or the like, to give compound 27. Compound 27 is then treated with a metal such as Li or a base such as n-BuLi or t-BuLi to afford the corresponding organolithium species, which is subsequently reacted with formaldehyde (or in a 2-step procedure is reacted first with DMF, and then with a reducing agent such as NaBH$_4$), to give a 3-thiophenemethanol compound that may be protected, for example, as a methoxymethyl ether or a bulky silyl ether, to give compound 28, where P is the protecting group. Compound 28 is then reacted in a two-step procedure, first by halogen-metal exchange, then by addition to compound 3 to give compound 29. Compound 29 is reduced with Zn in a strong acid, such as 6N HCl or the like, and the amino compound 30 is isolated. The O-protecting group is then removed by a suitable reagent, such as aqueous HCl, and the free alcohol is converted to a halide, with for example, PBr$_3$, SOCl$_2$, HCl, MsCl/LiCl, or the like, cyclized under basic conditions, for example, with K$_2$CO$_3$ in an alcoholic solution, and the catechol hydroxy groups are deprotected to give compound 31. Alternatively, the amino group of compound 30 may be protected, for example as a t-butyl carbamate, after which the alcohol is deprotected and oxidized to the aldehyde with an appropriate oxidizing agent such as SO$_3$.pyridine or MnO$_2$. The amine is then deprotected resulting in condensation of the amino and aldehyde groups to give the corresponding imine which is reduced with an appropriate reagent such as NaCNBH$_3$ in acetic acid. The remaining catechol protecting groups are removed as described in Scheme 2 to give compound 31.

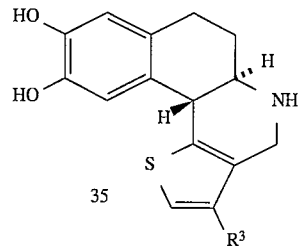

In accordance with Scheme 8, the substituted thiophene compounds of compound 32, wherein R$^3$ is as defined above, is prepared by reacting an appropriate organohalide compound, such as methyl iodide, ethyl bromide, or the like, or an appropriate chlorinating agent, such as N-chlorosuccinimide, for example, with the 3-lithio-4-bromo derivative of compound 26, prepared via a halogen-metal exchange with lithium metal, n-butyllithium or t-butyllithium, for example. Compound 32 is condensed with the 3-nitro-dihydro-naphthalene derivative of compound 3 under the conditions described for Scheme 2 above, to form compound 33. Compound 33 is converted to the corresponding des-bromo compound by hydrogenolysis, which compound is then reduced with zinc dust in HCl as described above to give a corresponding amino compound intermediate, which is then condensed as with paraformaldehyde as described for compound in Scheme 3 to give compound 34. Compound 34 is converted into compound 35 by the deprotecting procedure described for converting compound into compound 7 in Scheme 2 above.

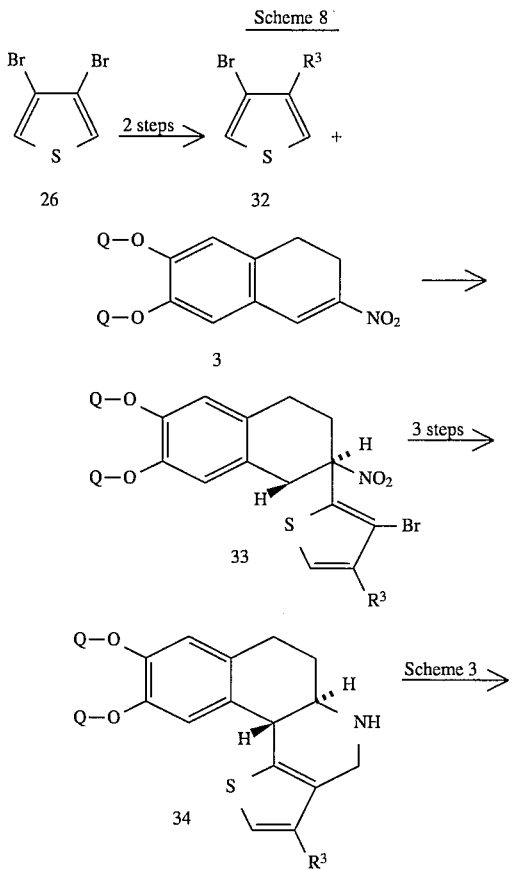

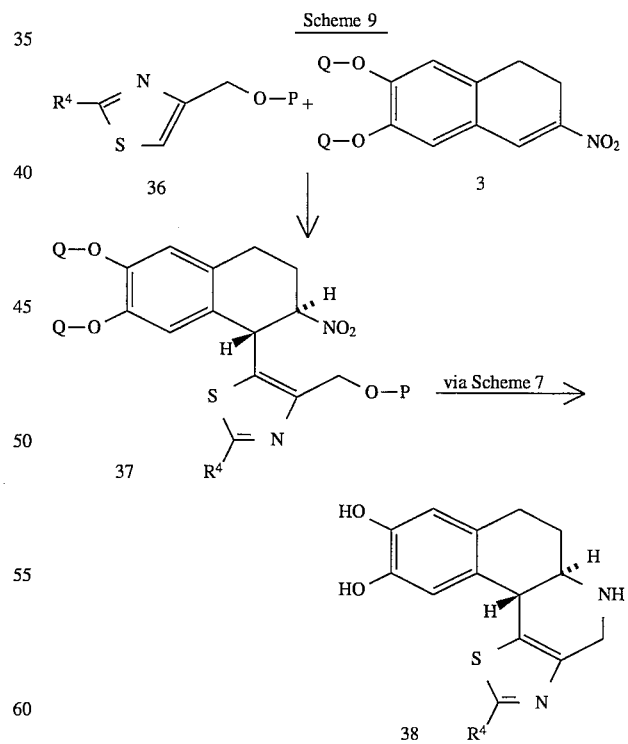

According to Scheme 9, a suitably-protected or unprotected 2-alkyl-4-thiazolemethanol compound 36 (prepared from L-cysteine ethyl ester as described in Example 27) is reacted with a base, such as lithium diisopropyl amide and the intermediate is then added to compound 3 to give compound 37. Compound 37 is then treated according to the procedures described for compound 29 and sequentially thereafter in Scheme 7 above to give the desired compound 38.

Scheme 10

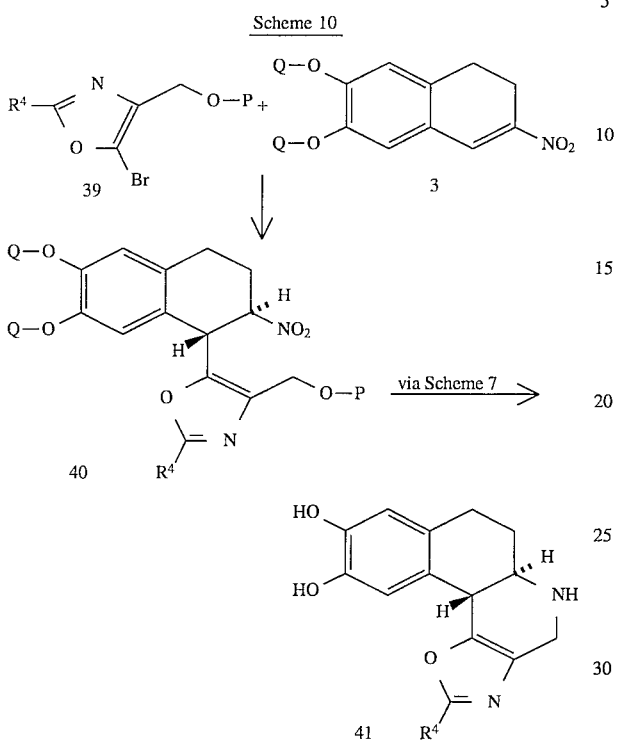

According to Scheme 10, the appropriately-protected 2-alkyl-5-bromo-4-oxazolemethanol compound 39 undergoes halogen metal exchange with a metal such as Li or with a strong base, such as n-butyl lithium or t-BuLi, and is then condensed with the compound 3, to give the protected intermediate compound 40. Compound 40 is then treated according to the procedures described for compound 29 and sequentially thereafter in Scheme 7 above to give the desired compound 41.

In accordance with Scheme 11, below, compounds 36 or 39, wherein $P^1$ is a protecting group such as a tetrahydropyranyl ether, undergo halogen-metal exchange or lithiation with Li or n-butyllithium or t-butyllithium, followed by addition of either an alkyl chlorformate, such as methyl chloroformate, or DMF, then subsequent reduction with either DIBAL or $NaBH_4$ to give the compounds 42. The free hydroxyl group of compounds 42 is then protected with a protecting group $P^2$, such as a methoxymethyl or pivalate, which allows for the selective removal of the $P^1$ protecting group with an acidic reagent, such as HCl, for example. The newly-exposed hydroxyl function is converted to an aidehyde by use of Swern's oxidation conditions to give the compounds 43. Sequential treatment of compounds 43 with nitromethane and ammonium acetate or, alternatively, in a two-step procedure with potassium t-butoxide and nitromethane, then with methanesulfonyl chloride and triethylamine to provide the compounds 44. Compound 45 is subjected to halogen-metal exchange with Scheme 11

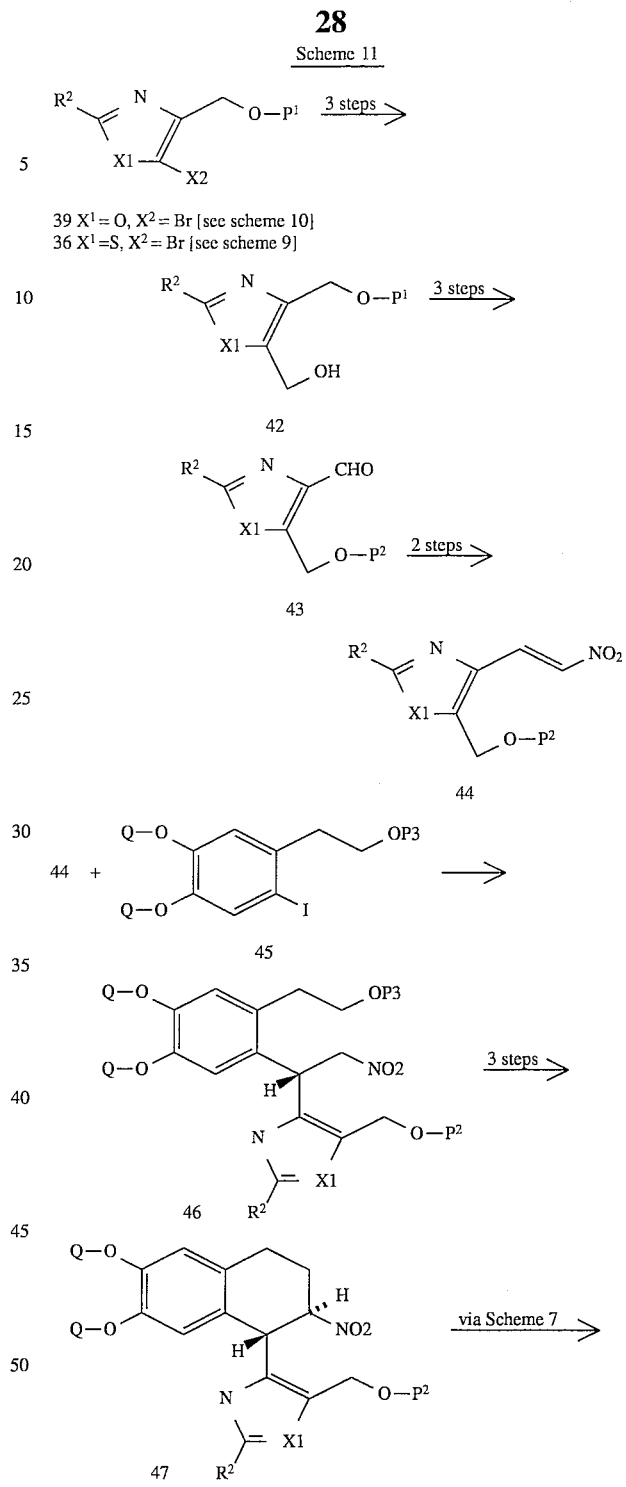

39 $X^1$ = O, $X^2$ = Br [see scheme 10]
36 $X^1$ = S, $X^2$ = Br [see scheme 9]

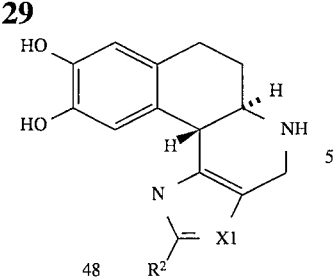

Li or n-butyllithium or t-butyllithium and condensed with the compound 44 to produce compounds 46. The p3 protecting group is then selectively removed with an acid such as aqueous HCl, and the free hydroxyl group is converted to a bromide group, by use of triphenyl phosphine and $CBr_4$ or 1,2-bis-(diphenylphosphino)-ethane and $CBr_4$, for example, and these intermediates are cyclized to the compounds 47 by treatment with a base, such as DBU. Conversion of compounds 47 to compounds 48 is accomplished by use of the procedure described in Scheme 7, above.

Scheme 12

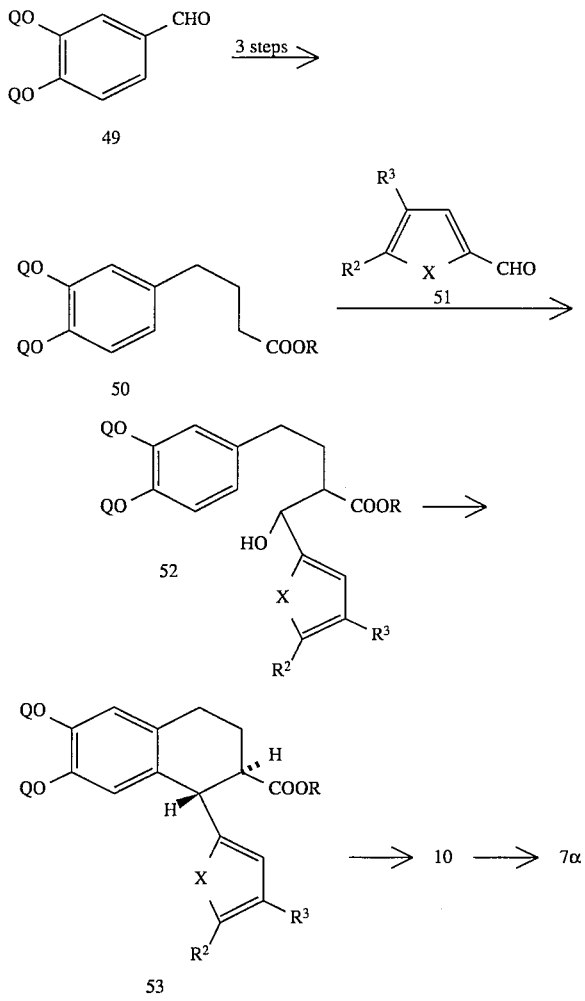

As an alternate to Scheme 3, in accordance with Scheme 12, compounds 49 are reacted with the appropriate Wittig reagent in the presence of a base such as NaH, followed by hydrogenation and esterification by stardard methods to give the compounds 50. Deprotonation of compounds 50 with a base such as LDA and subsequent aldol condensation with compounds 51, wherein X is O or S, provides the compounds 52. Compounds 52 undergo a Friedel-Crafts reaction in the presence of a Lewis acid, such as $SnCl_4$, to give compounds 53. Compounds 53 are converted to the compounds 10 (refer to Scheme 3 above) by means of a Curtius rearrangement, and carried on to compounds 7α by the procedures described for Scheme 3 above.

Certain abbreviations are used above and within the experimental section of this application. They are: DIBAL for diisobutylaluminum hydride; DBU for 1,8diazabicyclo [5.4.0]undec-7-ene; DMF for dimethyl formamide; DMSO for dimethyl sulfoxide; LDA for lithium diisopropylamide; PPTS for pyridinium p-toluenesulfonate; and THF for tetrahydrofuran.

The foregoing may be better understood by reference to the following examples which are provided for the illustration and not the limitation of the invention.

EXAMPLE 1 trans-2-methyl-4,5,5a,6,7,11b-hexahydro-1-thia-5-aza-cyclopent-2-ena[c]phenanthrene-9,10-diol 1a. 1.2-Dihydro-6.7-dimethoxynaphthalene To a solution of 5.01 g (24.3 mmol) of 6,7-dimethoxy-1-tetralone (Aldrich Chemical Co.) in 100 mL of ethanol was added 0.932 g (24.6 mmol) of NaBH4, and the mixture was stirred for 14 hours at room temperature. Most of the solvent was removed by evaporation, and to the residue was added 150 mL of methylene chloride and 50 mL of water. The aqueous layer was separated and reextracted with methylene chloride, then the organic extracts were combined and washed with brine, dried over $MgSO_4$, and concentrated to leave an orange oily residue. The crude intermediate product was dissolved in 100 mL of refluxing toluene, to which was added 48 mg of p-toluenesulfonic acid, and the solution was heated at reflux for 30 min. The reaction was cooled to room temperature and 50 mL of water was added. The aqueous layer was extracted with ethyl acetate, and the organic extracts were combined, washed with brine, dried over $MgSO_4$, and concentrated to leave an orange oil. This was dissolved in methylene chloride, which was washed with saturated sodium bicarbonate solution, water, dried and concentrated to afford 4.34 g of the title product (94% yield). NMR ($CDCl_3$) δ:6.67 (s, 1H), 6.60 (s, 1H), 6.38 (d, 1H, J=10 Hz), 5.94(dt, 1H, J=4 Hz, J=10 Hz), 3.88 (s, 3H), 3.86 (s, 3H), 2.73 (t, 2H, J=8 Hz), 2.32–2.24 (m, 2H).

1 b. 1,2-Dihydro-6,7-dimethoxy-3-nitronaphthalene

To a solution of 9.6 g (50.5 mmol) of 1,2-dihydro-6,7-dimethoxynaphthalene, from step 1a above, and 4.90 mL (60.6 mmol) of pyridine in 80 mL of acetone cooled to 0° C. was added 10 g (51 mmol) of tetranitromethane (Aldrich Chemical Co.), and the reaction was stirred for 5 min. The reaction was then quenched with 80 mL of 1M aqueous KOH and stirred at room temperature for 20 min. The yellow precipitate thus formed was filtered off, washed with water and dried. The flitrate was extracted with ethyl acetate, which was acidified with 1N HCl and washed with water. The solvent was dried over $MgSO_4$, concentrated and purified by flash chromatography, eluting with 8:1 hexane:ethyl acetate. The solvent was removed, and the solid was combined with the previous precipitate to afford a total of 9.7 g of the title product as a yellow solid. mp 90.5°– 91.0° C. NMR ($CDCl_3$) δ: 7.82 (s, 1H), 6.82 (s, 1H), 6.75 (s, 1H), 3.94 (s, 3H), 3.90 (s, 3H), (s, 3H), 2.98 (m, 4H).

1 c. trans-1,2,3,4-tetrahydro-6,7-dimethoxy-1-(5-methyl-2-thiophenyl)-2-nitronaphthalene A solution of 2-methylthiophene (Aldrich Chemical Co., 0.97 mL, 10 mmol) in 10 mL of dry THF was cooled to −78° C., 4 mL of n-butyl lithium (2.5M solution in hexanes, 10 mmol) was added, and the solution was stirred at −78° C. for 10 min and at 0° C. for 2.5 hours. The solution was again cooled to −78° C., and a solution of 2.30 g of 1,2-dihydro-6,7-dimethoxy-3-nitronaphthalene (10 mmol, from step 1b above) in THF was added dropwise via a cannula. Stirring was continued as the solution was allowed to warm to room temperature, and the reaction was then quenched with 100 mL of saturated $NH_4Cl$ solution. The mixture was then extracted with methylene chloride, which was dried over $Na_2SO_4$ and concentrated in vacuo to afford 3.04 g of crude product. This material was dissolved in 30 mL of acetonitrile and 0.75 mL of triethylamine was added, then the solution was stirred at room temperature for 16 hours. The solution was concentrated in vacuo, and the residue was purified by flash chromatography on silica gel, eluting with 14% ethyl acetate in hexanes, to afford 1.72 g (52% yield) of the trans isomer and 0.65 g (20% yield) of the cis isomer. NMR ($CDCl_3$) (trans isomer) δ:6.74 (d, 1H, J=3 Hz), 6.58 (s, 1H), 6.56 (dd, 1 H, J=1, J=3 Hz), 6.52 (s, 1H), 4.95–4.84 (m, 2H), 3.87 (s, 3H), 3.72 (s, 3H), 3.0–2.85 (m, 2H), 2.5–2.4 (m, 2H), 2.42 (s, 3H).

1d. trans-1,2,3,4-tetrahydro-6,7-dimethoxy-1-(5-methyl-2-thiophenyl)-2-naphthaleneamine To a suspension of 1.52 g of trans-1,2,3,4-tetrahydro-6, 7-dimethoxy-1-(5-methyl-2-thiophenyl)-2-nitro-naphthalene (4.5 mmol), from step 1c above, in 40 mL of 95% ethanol and 12 mL of 6 N HCl was added 2.97 g of Zn dust (45 mmol), added in four portions. The mixture was stirred at room temperature for 30 min, filtered, and the filtrate concentrated to half the original volume, then extracted with methylene chloride after addition of aqueous sodium bicarbonate solution. The organic extract was dried over $Na_2SO_4$ and concentrated to yield 1.35 g of the title product. MS $(M+H)^+$: 304. NMR ($CDCl_3$) δ:6.70 (d, 1H, J=3 Hz), 6.60 (bs, 2H), 6.46 (s, 1H), 3.88 (d, 1H, J=8 Hz), 3.85 (s, 3H), 3.69 (s, 3H), 3.18 (m, 1H), 2.92–2.78 (m, 2H), 2.43 (s, 3H), 2.12–2.04 (m, 1H), 1.78–1.64 (m, 1H).

1e. trans-9,10-dimethoxy-2-methyl-4,5,5a,6,7,11b-hexahydro-1-thia-5-aza-cyclopent-2-ena To a solution of 1.34 g of trans-1,2,3,4-tetrahydro-6,7-dimethoxy-1-(5-methyl-2-thiophenyl)-2-naphthaleneamine (44 mmol), from step 1d above, in 45 mL of methanol was added 2.8 g (20.2 mmol) of $K_2CO_3$. The mixture was stirred for 15 min, then 396 mg (13.2 mmol) of paraformaldehyde was added, and the suspension was stirred at room temperature for 18 hours. The reaction was filtered, and the filtrate was concentrated in vacuo. The residue was dissolved in 100 g trifluoroacetic acid (TFA), and the solution was stirred for 3 hours, then concentrated to about 10 mL and adjusted to a basic pH with aqueous sodium bicarbonate solution. The mixture was extracted 2× with methylene chloride, and the extract was washed with bdne, then dried over $Na_2SO_4$ and concentrated. The residue was purified by flash chromatography, eluting with 4% methanol in methylene chloride to afford 0.35 g (25% yield) of the title product. MS 316 $(M+H)^+$. NMR ($CDCl_3$) δ:7.40 (s, 3H), 6.64 (s, 1H), 6.48 (s, 1H), 4.12–4.05 (m, 3H), 3.93 (s, 3H), 3.86 (s, 3H), 3.1–2.88 (m, 3H), 2.47 (s, 3H), 2.28 (m, 1H), 1.90 (m, 1H).

1f. trans-2-methyl-4,5,5a,6,7,11b-hexahydro-1-thia-5-aza-cyclopent-2-ena[c]phenanthrene-9,10-diol hydrobromide To a stirred solution of 260 mg (0.83 mmol) of trans-9,10-dimethoxy-2-methyl-4,5,5a,6,7,11b-hexahydro-1-thia-5-aza-cyclopent-2-ena[c]phenanthrene from step 1e above, in 5 mL of methylene chloride cooled to −78° C. was added dropwise 3.3 mL of a 1.M solution of $BBr_3$ in methylene chloride (3.3 mmol). The reaction mixture was allowed to warm to 0° C. over a 2 hour period, then stirred at that temperature for 2 hours. The mixture was then cooled to −78° C., and the reaction was quenched by the slow addition of 5 mL of methanol. The solution was then stirred at room temperature for 20 min and at reflux for 30 min, then concentrated in vacuo. The product was collected by triturating with methylene chloride, filtering and drying to afford 274 mg of the title product (90% yield). mp 195°–8° C. MS 288 $(M+H)^+$. $^1$H NMR ($CD_3OD$) δ:1.9 (m, 1H), 2.30 (m, 1H), 2.49 (s, 3H), 2.90 (m, 2H), 3.42 (m, 1H), 4.28 (d, 1H, J=11 Hz), 4.35 (s, 2H), 6.62 (s, 1H), 6.68 (s, 1H), 7.30 (s, 1H). Anal. calc. for $C_{16}H_{18}BrNO_2S \cdot 0.3$ HBr: C, 48.96; H, 4.70; N, 3.57; found: C, 49.34; H, 4.65; N, 3.49.

EXAMPLE 2 trans-4,5,5a,6,7.11b-hexahydro-2-thia-5-aza-cyclopent-3-ena[c]phenanthrene-9.10-diol hydrobromide 2a. 3-Thiophenecarboxylic acid, N,N-diethylamide A solution of 5.0 g (39 mmol) of 3-thiophenecarboxylic acid (Aldrich Chemical Co.), to which was added 10 mL (134 mmol) of $SOCl_2$ in 20 mL of $CHCl_3$ was stirred at reflux for 3 hours. After cooling to room temperature, the solution was concentrated in vacuo. The residue was dissolved in 15 mL of methylene chloride, and the solution was cooled in an ice bath. To this was added dropwise 13 mL (126 mmol) of diethyl amine, and the reaction was stirred at room temperature for 1 hour. Water was added, and the mixture was extracted with methylene chloride, which was washed with aqueous $NaHCO_3$ solution, water, and bdne, and concentrated to give 9.3 g of crude product. This material was purified by flash chromatography on silica gel, eluting with 6:1 hexane:ethyl acetate, to afford 6.34 g of the title product after removal of the solvents. NMR ($CDCl_3$) δ:7.48 (dd, 1H, J=1, J=3 Hz), 7.32 (dd, 1H, J=3, J=6 Hz), 7.20 (dd, 1H, J=1, J=6 Hz), 3.60–3.30 (bs, 4H), 1.20 (bm, 6H).

2b. 2-Trimethylsilyl-3-thiophenecarboxylic acid, N,N-diethylamide

To a solution of 3 g (16.4 mmol) of 3-thiophenecarboxylic acid, N,N-diethylamide, from step 2a above, in 20 mL of THF cooled to −78° C. and stirred under $N_2$ was added 1.68 g (2.1 mL, 16.4 mmol) of N,N,N',N'-tetramethylenediamine (TMEDA), followed by 12.6 mL of a 1.3M solution of 2-butyl lithium in cyclohexane (16.4 mmol), and the reaction was stirred for 1 hour. Chlorotrimethylsilane (1.78 g, 2.1 mL, 16.4 mmol) was added, and the solution was stirred for 45 min, then poured into 100 mL of water. The mixture was extracted 3× with methylene chloride, and the solvent was washed with brine, dried over $MgSO_4$, concentrated, and purified by flash chromatography, eluting with 3:1 hexane:ethyl acetate to afford 1.4 g (38% yield) of the title product as an oil. MS 256 $(M+H)^+$. NMR ($CDCl_3$) δ:7.51 (d, 1 H, J=5 Hz), 7.10 (d, 1 H, J=5 Hz), 3.60–3.50 (bm, 2H), 3.3–3.10 (bm, 2H), 1.30–1.20 (bm, 3H), 1.15–1.05 (bm, 3H), 0.34 (s, 9H).

2c. trans-4-(1,2,3,4-tetrahydro-6,7-dimethoxy-2-nitronaphthalene- 1-yl)-5-trimethylsilyl -3-thiophenecarboxylic acid, N.N-diethylamide To a solution of 1.4 g (5.49 mmol) of 2-trimethylsilyl-3-thiophenecarboxylic acid N,N-diethylamide, from step 2b above, in 15 mL of THF cooled to −78° C. was added 0.7 mL (561 mg, 5.49 mmol) of TMEDA, followed by 4.2 mL of a 1.3M solution of 2-butyl lithium in cyclohexane (5.49 mmol), and the reaction was stirred for 40 min. To this solution was added a solution of 1.30 g of 1,2-dihydro6,7-dimethoxy-3-nitronaphthalene (5.49 mmol, from step 1 b above) in 20 mL of THF, and the reaction was stirred at −78° C. for 1 hour and at −20° C. for 1.5 hours, then quenched by the addition of saturated $NH_4Cl$. The mixture was diluted with water and extracted with methylene chloride. The solvent layer was washed with brine, dried over $MgSO_4$ and concentrated. The residue was dissolved in 50 mL of acetonitrile, 1 mL of triethylamine was added, and the reaction was stirred for 16 hours. The solvent and amine were removed by evaporation, and the residue was purified by flash chromatography over silica gel to afford 554 mg of the title product.

2d. trans-4-(2-amino-1,2,3,4-tetrahydro-6,7-dimethoxynaphthalene-1-yl)-3-thiophenecarboxylic acid, N,N-diethylamide To a solution of 554 mg of trans-4-(1,2,3,4-tetrahydro-6,7-dimethoxy-2-nitronaphthalene-1-yl) -5-trimethylsilyl-3-thiophenecarboxylic acid, N,N-diethylamide, from step 2c above, in 8 mL of ethanol and 3 mL of 6 N HCl was added 700 mg of Zn dust, and the mixture was stirred for 15 min. The mixture was diluted with 20 mL of methylene chloride, then filtered. The organic layer of the flitrate was separated. The aqueous layer was adjusted to pH 10 and extracted with methylene chloride. The extract was dried over $Na_2SO_4$, filtered and concentrated. The residue was dissolved in 7 mL of methanol, 3 mL of 6N HCl was added, and the solution was stirred for 4 hours. The methanol was evaporated off, and the residue was dissolved in 6 mL of water, which was then extracted with ether. The aqueous layer was adjusted to pH 10 and extracted with ethyl acetate. Removal of the solvent gave 256 mg of the title product. MS 389 $(M+H)^+$. NMR ($CDCl_3$) δ:7.24 (d, 1 H, J=6 Hz), 6.93 (d, 1 H, J=6 Hz), 6.58 (s, 1H), 6.43 (s, 1H), 4.23 (d, 1H, J=10 Hz), 3.85 (s, 3H), 3.67 (s, 3H), 3.64 (m, 1H), 3.50–3.30 (m, 4H), 3.0–2.76 (m, 2H), 2.32–2.22 (m, 1H), 1.90–1.80 (m, 1H), 1.26–1.12 (m, 6H).

2e. trans-9,10-dimethoxy-4,5,5a.6,7.11b-hexahydro-4-oxo-2-thia-5-aza-cyclopent -3-ena[c]phenanthrene To a solution of 240 mg of trans-4-(2-amino-1,2,3,4-tetrahydro-6,7-dimethoxynaphthalene-1-yl) -3-thiophenecarboxylic acid, N,N-diethylamide (from step 2d above) in 10 mL of toluene was added 2 mL of trimethylaluminum, and the solution was heated at reflux for 2 hours. The solution was cooled to room temperature, and the reaction was quenched by addition of $Na_2SO_4.10H_2O$ followed by addition of $K_2CO_3$ and stirring for 20 min. The mixture was filtered, and the flitrate was evaporated. The residue was dissolved in ethyl acetate, and washed with saturated $Na_2CO_3$ and brine. The solvent was removed, and the material was purified by flash chromatography on silica gel, eluting with 100:5:0.5 methylene chloride:ethanol:ammonium hydroxide, to afford 170 mg of the title product after removal of the solvents. MS 316 $(M+H)^+$. NMR ($CDCl_3$) δ:7.53 (d, 1H, J=6 Hz), 7.36 (s, 1H), 7.17 (d, 1H, J=6 Hz), 6.65 (s, 1H), 5.75 (bs, 1H), 4.49 (d, 1H, J=12 Hz), 3.98 (s, 3H), 3.88 (s, 3H), 3.80 (dd, 1H, J=4, J=12 Hz), 3.15–2.80 (m, 2H), 2.10–1.95 (m, 2H).

2f. trans-9,10-dimethoxy-4.5,5a,6,7,11b-hexahydro-2-thia-5-aza-cyclopent-3-ena[c]phenanthrene To a sample (170 mg) of trans-9,10-dimethoxy-4,5,5a,6,7,11b-hexahydro-4-oxo-2-thia-5-aza-cyclopent -3-ena[c] phenanthrene (from step 2e above) was added 10 mL of 1M $BH_3$ in THF, and the solution was heated at reflux for 8 hours. The reaction was allowed to cool to room temperature, then added to 4 mL of 15% NaOH and saturated $NaHCO_3$. The mixture was extracted with ethyl acetate, which was dried over $Na_2SO_4$, filtered and concentrated. To the residue was added 1.3 N HCl in methanol, and the solution was heated at reflux for 2 hours. The methanolic HCl was removed by evaporation, and the residue was partitioned between ethyl acetate and 0.5 N NaOH. The ethyl acetate was removed, and the crude material was purified by flash chromatography on silica gel, eluting with 5% methanol in methylene chloride. Removal of the solvent gave 74 mg of the title product (trans isomer). MS 302 $(M+H)^+$. NMR ($CDCl_3$) δ: 7.48 (s, 1H), 7.20 (d, 1H, J=6 Hz), 6.84 (d, 1H, J=6 Hz), 6.67 (s, 1H), 4.14 (s, 2H), 3.98 (d, 1H, J=9 Hz), 3.95 (s, 3H), 3.88 (s, 3H), 3.0–2.8 (m, 3H), 2.22 –2.14 (m, 1H), 1.9–1.78 (m, 1H).

2g. trans-4,5,5a,6,7,11b-hexahydro-2-thia-5-aza-cyclopent-3ena[c]phenanthrene -9,10-diol hydrobromide To a solution of 74 mg (0.24 mmol) of trans-9,10-dimethoxy-4,5,5a,6,7,11 b-hexahydro-2-thia-5-aza -cyclopent-3-ena[c]phenanthrene (from step 2f above)in 2 mL of methylene chloride cooled to −78° C. was added 2 mL of $BBr_3$ (1M in methylene chloride), and the solution was stirred for 1.5 hours, then quenched with 2 mL of methanol. The solution was stirred at 0° C. for 30 min, at room temperature for 30 min, and at reflux for 30 min, then concentrated in vacuo and dried to afford 81 mg of a 4/1 trans/cis mixture of the title product. MS 274 $(M+H)^+$. NMR (trans) ($OD_3OD$) δ:7.38 (d, 1H, J=6 Hz), 6.92 (d, 1H, J=6 Hz), 6.90 (s, 1H), 6.58 (s, 1H), 4.45–4.20 (m, 3H), 4.10 (m, 1H), 3.0–2.8 (m, 2H), 2.2–1.95 (m, 2H). Anal Calc. for $C_{15}H_{16}BrNO_2S.0.30$ HBr: C, 47.59; H, 4.34; N, 3.70; found: C, 47.87; H, 4.30; N, 3.40.

EXAMPLE 3 trans-2-ethyl-4,5,5a,6,7,11b-hexahydro-3-thia-5-aza-cyclopent-1-ena[c]phenanthrene-9,10-diol hydrobromide 3a. 5-Ethyl-2-thiophenecarboxylic acid To a solution of 20 g (0.18 mol) of 2-ethylthiophene (Aldrich Chemical Co.) in 150 mL of THF cooled to 0° C. was added 73 mL (0.18 mol) of 2.5M (in hexane) n-butyl lithium, and the solution was stirred at 0° C. for 40 min, then cooled to −15° C., and gaseous $CO_2$ was bubbled into the mixture. After 40 min, the solution was poured into water and adjusted to pH 14 by addition of 20% NaOH. The solution was washed with ether, which was discarded, and the aqueous layer was adjusted to pH 1 with 6N HCl. This solution was extracted 3× with ethyl acetate, and the extract was dried over $MgSO_4$ and concentrated to give 28.3 g (99% yield) of the title product. MS 174 $(M+H)^+$. NMR ($CDCl_3$) δ:7.73 (d, 1H, J=3 Hz), 6.84 (d, 1H, J=3 Hz), 2.90 (q, 2H, J=7 Hz), 1.35 (d, 3H, J=7 Hz).

3b. 5-Ethyl-2-thiophenecarboxylic acid, N-t-butyl amide

To a solution of 28 g (0.18 mol) of 5-ethyl-2-thiophenecarboxylic acid, from step 3a above, in 130 mL of methylene chloride was added a large excess (130 mL, 10 mol) of thionyl chloride, and the solution was heated at reflux for 2 hours. The solvent and excess reagent were removed by evaporation, and the residue was dissolved in 130 mL of chloroform and cooled to 0° C. To this solution was added 94 mL (0.9 mol) of t-butylamine dropwise, and the solution was stirred at reflux for 2 hours. The reaction was cooled, the solution poured into water, and the mixture extracted with ethyl acetate. The extract was washed with water and brine, dried, and concentrated. The residue was dissolved in ethyl acetate and the crude product was precipitated by addition of hexane. The crude product was collected by filtration and purified by flash chromatography over silica gel, eluting with 1:6 ethyl acetate:hexane, to afford 13.3 g (80% yield) of the title product after drying. MS 212 (M+H)$^+$. NMR (CDCl$_3$) δ: 7.25 (d, 1H, J=3 Hz), 6,72 (d, 1H, J=3 Hz), 5.70 (bs, 1H), 2.84 (q, 2H, J=7 Hz), 1.45 (s, 9H), 1.31 (t, 3H, J=7 Hz).

3c. trans-3-(1,2,3,4-tetrahydro-6,7-dimethoxy-2-nitronaphthalene-1-yl)-5-ethyl -2-thiophenecarboxylic acid, N-t-butylamide To a solution of 5.4 g (25.5 mmol) of 5-ethyl-2-thiophenecarboxylic acid, N-t-butyl amide, from step 3b above, in 80 mL of THF cooled to −78° C. was added 20.4 mL (51.1 mmol) of n-butyllithium (2.5M in hexane). The solution was then stirred at 0° for 40 min, then re-cooled to −78° C., and a solution of 6.0 g of 1,2-dihydro-6,7-dimethoxy-3-nitronaphthalene, from Example 1 b above, in 100 mL of THF cooled to −78° C. was added via cannula. The solution was stirred at −78° C. for 1 hour and at 0° C. for 1 hour. The reaction was quenched with saturated NH$_4$Cl, diluted with water, and extracted with methylene chloride. The extract was washed with brine, dried and concentrated. The residue was dissolved in 30 mL of acetonitrile, 1 mL of triethylamine was added, and the reaction was stirred for 16 hours. The solvent was evaporated, and the residue was purified by flash chromatography, eluting with 6:1 hexane:ethyl acetate to afford 5.7 g of the title product. MS 447 (M+H)$^+$, 464 (M+NH$_4$)$^+$. NMR (CDCl$_3$), δ:6.48 (s, 1H), 6.37 (s, 1H), 6.30 (s, 1H), 5.70 (bs, 1H, 5.47 (d, 1H, J=8 Hz), 5.05 (m, 1H), 3.85 (s, 3H) 3.69 (s, 3H), 3.2–2.88 (m, 2H), 2.72 (q, 2H, J=7 Hz), 2.5–2.35 (m, 2H), 1.42 (s, 3H), 1.23 (t, 3H, J=7 Hz).

3d. trans-3-(2-amino-1,2,3,4-tetrahydro-6,7-dimethoxynaphthalene-1-yl)-5-ethyl -2-thiophenecearboxylic acid, N-t-butylamide To a solution of 5.7 g (127.8 mmol) of trans-3-(1,2,3,4-tetrahydro-6,7-dimethoxy-2-nitronaphthalene-1-yl)-5-ethyl-2-thiophenecarboxylic acid, N-t-butylamide, from step 3c above, in 80 mL of ethanol was added 40 mL of 6N HCl and 8.4 g (127.8 mmol) of Zn dust, and the suspension was stirred for 10 min. The zinc was removed by filtration, and the solution was concentrated by half, diluted with water, and adjusted to pH 9 with 20% NaOH and saturated NaHCO$_3$. The mixture was extracted with methylene chloride. The extract was washed with brine, dried over Na$_2$SO$_4$, and concentrated to give 5.2 g of the title product. MS 417 (M+H)$^+$. NMR (CDCl$_3$) δ:6.59 (s, 1H), 6.28 (s, 1H), 6.18 (s, 1H), 4.67 (d, 1H, J=10 Hz), 3.85 (s, 3H), 3.65 (s, 3H), 3.48 (m, 1H), 3.02–2.80 (m, 2H), 2.72 (q, 2H, J=7 Hz), 2.60 (m, 1H), 2.10 (m, 1H), 1.44 (s, 9H), 1.22 (t, 2H, J=7 Hz).

3e. trans-2-ethyl-9,10-dimethoxy-4,5,5a,6,7,11b-hexahydro-3-thia-4-oxo-5-aza-cyclopent -1-ena[c]phenanthrene and 1-(5-ethylthioohene-3-yl)-1,2,3,4-tetrahydro -6,7-dimethoxy-2-naphthaleneamine To a solution of 5.2 g (12.5 mmol) of trans-3-(2-amino-1,2,3,4-tetrahydro-6,7-dimethoxynaphthalene-1-yl)-5-ethyl-2-thiophenecarboxylic acid, N-tbutylamide, from step 3d above, in 6 mL of methanol was added 100 mL of 10% H$_2$SO$_4$. The solution was heated at reflux for 25 hours, and cooled to room temperature. The crude product precipitated out and was collected by filtration, and a second crop was obtained by adjusting the flitrate to pH 9 with 20% NaOH and extracting with methylene chloride. Removal of the solvent and chromatographing provided two products. Total yield of the cyclopentenaphenanthrene title product was 1.43 g (33% yield). MS 344 (M+H)$^+$. NMR (CDCl$_3$) δ:7.15 (s, 2H), 6.66 (s, 1H), 5.73 (bs, 1H), 4.15 (d, 1H, J=13 Hz) 3.94 (s, 3H), 3.89 (s, 3H), 3.76 (dt, 1H, J=4, J=13 Hz), 2.90 (q, 2H, J=7 Hz), 2.9–2.8 (m, 2H), 2.05–1.90 (m, 2H), 1.33 (t, 3H, J=7 Hz). The naphthaleneamine product was obtained in 51% yield (2.02 g). MS 318 (M+H)$^+$. NMR (CDCl$_3$) δ:6.85 (d, 1H, J=1 Hz), 6.60 (s, 1H), 6.49 (d, 1H, J=1 Hz), 6.33 (s, 1H), 3.88 (s, 3H), 3.77 (d, 1 H, J=8 Hz), 3.66 (s, 3H), 3.2 (bt, 1 H, J=8 Hz), 2.92–2.82 (m, 2H), 2.79 (q, 2H, J=7 Hz), 2.3–2.0 (bm, 3H), 1.75 (m, 1H), 1.26 (t, 3H, J=7 Hz).

3f. trans-2-ethyl-9,10-dimethoxy-4,5,5a,6,7,11b-hexahydro-3-thia-5-aza-cyclopent-1-ena[c]phenanthrene To a solution of 2.0 g (6.3 mmol) of 1-(5-ethylthiophene-3-yl)-1,2,3,4-tetrahydro-6,7-dimethoxy-2-naphthaleneamine, from step 3e above, in 30 mL of ethanol was added 5 mL of 37% paraformaldehyde, and the reaction was stirred for 15 min. To this solution was added 2 mL of 6 N HCl, and the solution was heated at reflux for 3 hours, then cooled to room temperature. The solution was diluted with water, adjusted to a basic pH with saturated NaHCO$_3$ and extracted with methylene chloride. The organic extract was washed with water and brine, dried over Na$_2$SO$_4$, and concentrated. The residue was chromatographed to afford 1.41 g of the title product. MS 330 (M+H)$^+$. NMR (CDCl$_3$) δ:7.02 (s, 1H), 6.92 (s, 1H), 6,74 (s, 1H), 4.06 (s, 2H), 3.88 (s, 3H), 3.82 (s, 3H), 3.58 (d, 1H, J=10 Hz), 3.0–2.8 (m, 4H), 2.75–2.65 (m, 1H), 2.3–2.16 (m, 1H), 1.75–1.60 (m, 1H), 1.33 (t, 3H, J=8 Hz).

3g. alternate preparation of trans-2-ethyl-9,10-dimethoxy-4,5,5a,6,7,11b-hexahydro -3-thia-5-aza-cyclopent-1-ena[c]phenanthrene To a solution of 1.4 g (4.08 mmol) of trans-2-ethyl-9,10-dimethoxy-4,5,5a,6,7,11b -hexahydro-3-thia-4-oxo-5-aza-cyclopent-1-ena[c]phenanthrene, from step 3e above, in 10 mL of THF was added 20.4 mL of BH$_3$TrHF (1.0M in THF). The solution was heated to reflux for 15 hours, cooled to 0° C., and quenched by the addition of 10 mL of 1.3M HCl in methanol. The solution was then heated at reflux for 4 hours, diluted with water, adjusted to pH 9 and extracted with methylene chloride. The solvent was washed with brine, dried over Na$_2$SO$_4$, concentrated, and the residue chromatographed on silica gel, eluting with 2.5:97.5 methanol:methylene chloride. Removal of the solvent afforded 910 mg of the title product (68% yield).

3h. trans-2-ethyl-4,5,5a,6,7,11b-hexahydro-3-thia-5-aza-cyclopent-1-ena[c]phenanthrene-9,10-diol hydrobromide To a solution of 130 mg (1.03 mmol) of 2-ethyl-9,10-dimethoxy-4,5,5a,6,7,11b -hexahydro-3-thia-5-aza-cyclopent-1-ena[c]phenanthrene, from step 3f above, in 5 mL of methylene chloride cooled to −78° C. was added 0.15 mL of BBr$_3$ (1.0M in CH$_2$Cl$_2$), and the solution was stirred at −78° C. for 2 hours and 0° C. for 2 hours. The solution was then cooled to −78° C., and the reaction was quenched by addition of methanol. The solution was stirred at room temperature for 20 min, heated at reflux for 30 min, and concentrated to a solid residue, which was dried under vacuum to afford 156 mg of the title product. mp 235°–236° C. MS 302 (M+H)$^+$. NMR (CD$_3$OD) δ:7.20 (s, 1H), 6.90 (s, 1H), 6.67 (s, 1H), 4.46 (s, 2H), 4.02 (d, 1 H, J=11 Hz), 3.2 (m, 1H), 3.0–2.8 (m, 4H), 2.40–2.28 (m, 1H), 2.20–1.86 (m, 1H), 1.36 (t, 3H, J=7 Hz). Anal. calc. for $C_{17}H_{20}BrNO_2S \cdot 0.10$ HBr: C, 52.30; H, 5.19; N, 3.59; found: C, 52.30; H, 5.13; N, 3.54

EXAMPLE 4

(−)-trans-2-ethyl-4,5,5a,6,7,11b-hexahydro-3-thia-5-aza-cyclopent-1-ena[c]phenanthrene-9,10-diol hydrobromide 4a.   (−)-trans-2-ethyl-4,5,5a,6,7,11b-hexahydro-9,10-dimethoxy-3-thia-5-azacyclopent-1-ena [c]phenanthrene A sample of trans-2-ethyl-9,10-dimethoxy-4,5,5a,6,7,11b-hexahydro-3-thia-5-aza -cyclopent-1-ena[c]phenanthrene, from step 3f or 3g above, was separated by chiral HPLC on a Chiracel™ OD column to give two products. The fraction possessing a specific rotation of [a] (23° C., c=0.68 in methanol)=−321° was isolated and carried forward to the next step.

4b.   (−)-trans-2-ethyl-4,5,5a,6,7,11b-hexahydro-3-thia-5-aza-cyclopent-1-ena[c]phenanthrene-9,10-diol hydrobromide To a solution of 340 mg (1.03 mmol) of chiral 2-ethyl-9,10-dimethoxy-4,5,5a,6,7,11-b-hexahydro -3-thio-5-aza-cyclopen-1-ena[c]phenanthrene, from step a above, in 8 mL of methylene chloride cooled to −78° C. was added 8 mL of $BBr_3$ (1M in methylene chloride), and the solution was stirred at −78° C. for 2 hours and 0° C. for 2 hours. The solution was then cooled to −78° C., and the reaction was quenched by addition of 4 mL of methanol and stirred for 30 min at room temperature and heated at reflux for 30 min. The volatiles were removed by evaporation, and the residue was dissolved in water and extracted with ether. The aqueous layer was taken to dryness to afford 363 mg (92% yield) of the title product. mp 174°–5° C. [α](23° C.,c=1.01 in methanol)=−192.2°. MS 302(M+H)$^+$. NMR ($CD_3OD$) δ:7.20 (s, 1H), 6.90 (s, 1H), 6.67 (s, 1H), 4.46 (s, 2H), 4.02 (d, 1H, J=11 Hz), 3.2 (m, 1H), 3.0–2.8 (m, 4H), 2.40–2.28 (m, 1H), 2.20–1.86 (m, 1H), 1.36 (t, 3H, J=7 Hz). Calc for $C_{17}H_{20}BrNO_2S \cdot 0.60$ $H_2O$: C, 51.94; H, 5.43; N, 3.56; Found: C, 51.74; H, 5.22; N, 3.53.

EXAMPLE 5 trans-2-propyl-4,5,5a,6,7,11b-hexahydro-3-thia-5-aza-cyclopent-1-ena[c]phenanthrene-9,10-diol hydrobromide 5a. 5-propyl-2-thiophenecarboxylic acid, N-t-butyl amide To a 5.7 g (46.3 mmol) sample of 2-propylthiophene (prepared according to the method given in *Bull. Chem. Soc. Japan*, 52, 1865 (1979)) dissolved in 60 mL of THF was added 18.5 mL (46.3 mmol) of a solution of n-butyl lithium (2.5M in hexane) at 0° C. under a nitrogen atmosphere. The solution was stirred at 0° C. for 50 min, then cooled to −78° C. and 4.8 g (48.6 mmol) of t-butylisocyanate was added. The solution was stirred at −78° C. for 40 min and at 0° C. for 1 hour. The reaction was quenched by addition of saturated ammonium chloride solution, then poured into water, and the mixture was extracted with ethyl acetate. The extract was washed with water and brine, dried over $MgSO_4$ and concentrated to give 6.27 g of the title product as a solid. MS 226 (M+H)$^+$. NMR ($CDCl_3$) δ:0.97 (t, 3H, J=8 Hz), 1.45 (s, 9H), 1.7 (sextet, 2H, J=8 Hz), 2.78 (t, 2H, J=8 Hz), 5.7 (bs, 1H), 6,71 (d, 1H, J=4 Hz), 7.25 (d, 1H, J=4 Hz).

5b.   2-propyl-9,10-dimethoxy-4,5,5a,6,7,11b-hexahydro-3-thia-5-aza-cyclopent-1-ena[c]phenanthrene Following the procedures of Example 3c–3f, replacing the 5-ethyl-2-ethylthiophenecarboxylic acid N-t-butyl amide of step 3c with a 6.27 g sample of 5-propyl-2-thiophenecarboxylic acid, N-t-butyl amide, from step 5a above, the title compound was prepared. MS 344 (M+H)$^+$. NMR ($CDCl_3$) δ:1.0 (t, 3H, J=7 Hz), 1.72 (tq, 2H, J=5, J=7 Hz), 1.85–1.95 (m, 1H), 2.38–2.40 (m, 1H), 2.81 (t, 2H, J=5 Hz), 2.8–3.05 (m, 3H), 3.68 (d, 1H, J=10 Hz), 3.81 (s, 3H), 3.88 (s, 3H), 4.12 (s, 2H), 6,73 (s, 1H), 6.90 (s, 1H), 7.01 (s, 1H).

5c.   trans-2-propyl-4,5,5a,6,7,11b-hexahydro-3-thia-5-aza-cyclopent-1-ena[c]phenanthrene-9,10-diol hydrobromide Reacting the compound from step 5b above with $BBr_3$ (1.0M in $CH_2Cl_2$), according to the procedure of Example 3h above, afforded the title compound. mp 133°–4° C. MS :316 (M+H)$^+$. NMR ($CD_3OD$) ,δ:1.03 (t, 3H, J=8 Hz), 1.75 (sx, 2H, J=8 Hz), 1.9–2.0 (m, 1H), 2.28–2.41 (m, 1H), 2.87 (t, 2H, J=8 Hz), 2.88–3.05 (m, 2H), 3.15–3.27 (m, 1H), 4.02 (d, 1H, J=11 Hz), 4.46 (s, 2H), 6.67 (s, 1H), 6.90 (s, 1H), 7.02 (s, 1H). Anal. calc. for $C_{18}H_{22}BrNO_2S \cdot 0.3H_2$: C, 53.81; H, 5.67; N, 3.49; found: C, 53.67; H, 5.64; N, 3.28.

EXAMPLE 6 trans-2-(1,1-dimethylethyl)-4,5,5a,6,7,11b-hexahydro-3-thia-5-aza-cyclopent-1-ena[c]phenanthrene-9,10-diol hydrobromide 6a. 5-(1,1-dimethylethyl)-2-thiophenecarboxylic acid To a solution of 5.0 g (39.02 mmol) of thiophene-2-carboxylic acid (Aldrich Chemical Co.) in 100 mL of methylene chloride stirred at 0° C. was added 11 g (82.5 mmol) of $AlCl_3$ and 5.8 g (43.0 mmol) of t-butyl bromide. The solution was stirred at room temperature for 18 hours then poured into 100 mL of ice water, and the mixture was extracted with ether. The extracts were washed with brine and dried over $MgSO_4$, then concentrated to give 3.33 g of the title product. MS (M+H)$^+$: 202. NMR ($CDCl_3$) δ:1.42 (s, 9H), 6.89 (d, 1H, J=4 Hz), 7.72 (d, 1H, J=4 Hz).

6b.   trans-2-(1,1-dimethylethyl)-4,5,5a,6,7,11b-hexahydro-3-thia-5-aza-cyclopent-1-ena[c]phenanthrene-9,10-diol hydrobromide Following the procedures of Example 3b–3f, and 3h, replacing the 2-ethylthiophenecarboxylic acid of step 3b with 5-(1,1-dimethylethyl)-2-thiophenecarboxylic acid (from step 6a above) the title compound was prepared. mp 197°–8°C. MS :330 (M+H)$^+$. NMR ($CD_3OD$) ,δ:1.46 (s, 9H), 1.86–2.02 (m, 1H), 2.29–2.43 (m, 1H), 2.78–3.04 (m, 2H), 3.16–3.28 (m, 1H), 4.02 (d, 1H, J=11 Hz), 4.46 (s, 2H), 6.68 (s, 1H), 6.88 (s, 1H), 7.03 (s, 1H). Anal. calc. for $C_{19}H_{24}BrNO_2S \cdot 0.6H_2O$: C, 54.18; H, 6.03; N, 3.33; found: C, 54.11; H, 5.79; N, 3.19.

EXAMPLE 7 trans-2-(2-propyl)-4,5,5a,6,7,11b-hexahydro-3-thia-5-aza-cyclopent-1-ena[c]phenanthrene-9,10-diol hydrobromide Following the procedures of Example 6, substituting 2-propyl bromide for the t-butyl bromide of step 6a, the title compound was prepared. mp 186°–7° C. MS :316. NMR ($CD_3OD$) δ:1.39 (d, 6H, J=7 Hz), 1.87–2.02 (m, 1H), 2.28–2.43 (m, 1H), 2.8–3.28 (m, 4H), 4.03 (d, 1 H, J=1 1 Hz), 4.47 (s, 2H), 6.68 (s, 1H), 6.89 (s, 1H), 7.03 (s, 1H). Anal. calc. for $C_{18}H_{22}BrNO_2S \cdot 0.4H_2O$: C, 53.57; H, 5.69; N, 3.47; found: C, 53.35; H, 5.48; N, 3.38.

EXAMPLE 8 trans-2-butyl-4,5,5a,6,7,11b-hexahydro-3-thia-5-aza-cyclopent-1-ena[c]phenanthrene-9,10-diol hydrobromide Following the procedures of Example 5, substituting 2-butyl thiophene (prepared according to the method given in *Bull. Chem. Soc. Japan*, 52, 1865 (1979)) for the 2-propylthiophene of example 5a, the title compound was prepared. mp 152°–3° C. MS: 330 (M+H)$^+$. NMR (CD$_3$OD) δ:0.98 (t, 3H, J=7 Hz), 1.35–1.5 (m, 2H), 1.6–1.8 (m, 2H), 1.85–2.0 (m, 1H), 2.26–2.4 (m, 1H), 2.76–3.05 (m, 4H), 3.16–3.26 (m, 1H), 4.01 (d, 1 H, J=11 Hz), 4.46 (s, 2H), 6.67 (s, 1H), 6.89 (s, 1H), 7.02 (s, 1H). Anal. calc. for C$_{19}$H$_{24}$BrNO$_2$S.0.6H$_2$O: C, 54.18; H, 6.03; N, 3.33; found: C, 54.18; H, 5.83; N, 3.17.

EXAMPLE 9 trans-2-(2-methylpropyl)-4,5,5a,6,7,11b-hexahydro-3-thia-5-aza-cyclopent-1-ena[c]phenanthrene-9,10-diol hydrobromide Following the procedures of Example 5, substituting 2-(2methylpropyl)thiophene (prepared according to the method given in *Bull Chem. Soc. Japan*, 52, 1865 (1979)) for the 2-propylthiophene of example 5a, the title compound was prepared. mp 164°%14 165° C. MS: 330 (M+H)$^+$. NMR (CD$_3$OD) δ:0.98 (d, 3H, J=7 Hz), 1.01 (d, 3H, J=7 Hz), 1.85–2.0 (m, 2H), 2.27–2.4 (m, 1H), 2.75 (d, 2H, J=7 Hz), 2.8–3.05 (m, 2H), 3.15–3.28 (m, 1H), 4.02 (d, 1 H, J=11 Hz), 4.48 (s, 2H), 6.67 (s, 1H), 6.89 (s, 1H), 7.00 (s, 1H). Anal. calc. for C$_{19}$H$_{24}$BrNO$_2$S.0.1HBr: C, 54.53; H, 5.81; N, 3.35; found: C, 54.60; H, 5.82; N, 3.28.

EXAMPLE 10 trans-2-(2,2-dimethylPropyl)-4,5,5a,6,7,11b-hexahydro-3-thia-5-aza-cyclooent-1-ena[c]Phenanthrene-9,10-diol hydrobromide 10a. 2-(2,2-dimethylpropyl)thiophene To 45 mL of diethylene glycol was added 5.04 g (90 mmol) of KOH, and the mixture was stirred until solution was complete. To this was added 5.05 g (30 mmol) of 2.2-dimethyl-1-thiophenyl-1-propanone (Lancaster Chemical Co.), and 3.75 g of hydrazine monohydrate, and the reaction was stirred at reflux for 48 hours. The solution was cooled, diluted with 100 mL of 1N HCl and 100 mL of water, and extracted with pentane. The extract was dried over MgSO$_4$, filtered and concentrated to give 4.31 g of the title product. NMR (CDCl$_3$) δ:0.95 (s, 9H), 2.70 (s, 2H), 6.75 (dd, 1H, J=1, J=4 Hz), 6.98 (dd, 1H, J=4, J=6 Hz), 7.12 (dd, 1H, J=1, J=6 Hz).

10b. 2-(2,2-dimethylpropyl)-4,5,5a,6,7,11b-hexahydro-3-thia-5-aza-cyclopent-1-ena[c]phenanthrene-9,10-diol hydrobromide Following the procedures of Example 5, substituting 2-(2,2-dimethylpropyl)thiophene, from step 10a above for the 2-propylthiophene of step 5a, the title compound was prepared. MS: 344 (M+H)$^+$. NMR (CD$_3$OD) δ:1.02 (s, 9H), 1.85–2.0 (m, 1H), 2.28–2.42 (m, 1H), 2.7–3.05 (m, 4H), 3.15–3.3 (m, 1H), 4.03 (d, 1H, J=11 Hz), 4.48 (s, 2H), 6.67 (s, 1H), 6.89 (s, 1H), 6.99 (s, 1H). Anal. calc. for C$_{20}$H$_{26}$BrNO$_2$S.0.1HBr.0.1 propanol: C, 56.03; H, 6.90; N, 2.88; found: C, 56.03; H, 6.88; N, 2.84.

EXAMPLE 11 trans-2-cyclohexyl-4,5,5a,6,7,11b-hexahydro-3-thia-5-aza-cyclopent-1-ena[c]phenanthrene-9,10-diol hydrobromide 11 a. 2-cyclohexylthiophene To 20 mL of a 0.5M solution of tricyclohexylborane (10 mmol, prepared according to *Syn. Comm.*, 12:43 (1982)) was added 10 mL of a 1.0M solution of 2-lithiothiophene in THF (10 mmol, Aldrich Chemical Co.). The resulting suspension was stirred at reflux for 2 hours, at the end of which the solids had dissolved. The solution was then cooled to −78° C. and treated with a solution of iodine (2.54 g 10 mmol) in 15 mL of dry ether, and the reaction was stirred while warming to room temperature over a 2.5 hour period, then stirred for 45 min at room temperature. The reaction was quenched by the careful and simultaneous dropwise addition of 3 N NaOH (10 mL) and 30% H2O2 (10 mL), then stirred at room temperature for 2 hours. The mixture was diluted with ether, washed with aqueous K$_2$CO$_3$, water, and brine, and dried, then concentrated in vacuo. The crude product was purified by flash chromatography on silica gel eluting with hexane, to afford after removal of the solvent 1.42 g of the title product. NMR (CDCl$_3$) δ:1.2–1.5 (m, 6H), 1.6–2.1 (m, 4H), 2.75–2.87 (m, 1H), 6.80 (dd, 1H, J=1, J=3 Hz), 6.92 (dd, 1H, J=3, J=5 Hz), 7.12 (dd, 1H, J=1, J=5 Hz).

11b. trans-2-cyclohexyl-4,5,5a,6,7,11b-hexahydro-3-thia-5-aza-cyclopent-1-ena[c]phenanthrene-9,10-diol hydrobromide Following the procedures of example 3a–3f and 3h, substituting the 2-cyclohexylthiophene of step 11 a above for the 2-ethylthiophene of example 3a, the title product was prepared. mp 191°–2° C. MS: 356 (M+H)$^+$. NMR (CD$_3$OD) δ:1.2–1.5 (m, 6H), 1.7–2.2 (m, 5H), 2.28–2.4 (m, 1H), 2.8–3.04 (m, 2H), 3.15–3.3 (m, 1H), 4.02 (d, 1 H, J=1 1 Hz), 4.46 (s, 2H), 6.67 (s, 1H), 6.89 (s, 1H), 7.02 (s, 1H). Anal. calc. for C$_{21}$H$_{26}$BrNO$_2$S.0.1H$_2$O.0.2HBr: C, 55.51;H, 5.86; N, 3.08; found: C, 55.35; H, 5.84; N, 2.98.

EXAMPLE 12 trans-2-phenyl-4,5,5a,6,7.11 b-hexahydro-3-thia-5-aza-cyclopent-1-ena[c]phenanthrene-9,10-diol hydrobromide Following the procedures of Example 5, substituting 2-phenylthiophene (prepared according to the method given in *Bull. Chem. Soc. Japan*, 52, 1865 (1979)) for the 2-propylthiophene of example 58, the title compound was prepared. mp 204°–5° C. MS :350. NMR (CD$_3$OD) δ:1.9–2.05 (m, 1H), 2.32–2.44 (m, 1H),2.8–3.06 (m, 2H),3.2–3.3(m, 1H), 4.12 (d, 1H, J=11 Hz), 4.52 (d, 1H, J=15 Hz), 4.60 (d, 1H, J=1 5 Hz), 6.68 (s, 1H), 6.97 (s, 1H), 7.3–7.5 (m, 3H), 7.58 (s, 1H), 7.66–7.75 (m, 2H). Anal. calc. for C$_{21}$H$_{20}$BrNO$_2$S.0.2HBr: C, 56.49; H, 4.56; N, 3.14; found: C, 56.59; H, 4.65; N, 3.12.

EXAMPLE 13 trans-2-(1,1-dimethylethyl)-4,5,5a,6,7,11b-hexahydro-1-thia-5-aza-cyclopent-2-ena[c]phenanthrene-9,10-diol hydrobromide 13a. 5-(1,1-dimethylethyl)-3-thiophenecarboxaldehyde To a solution of 3.63 g (32.4 mmol) of 3-thiophenecarboxaldehyde (Aldrich Chemical Co.) in 60 mL of methylene chloride cooled to 0° C. was added 9.17 g (80.9 mmol) of AlCl$_3$ and 2-methyl-2-bromopropane. The solution was stirred under N2 at room temperature for 16 hours and at reflux for 4 hours. The solution was then cooled to room temperature, and the reaction was quenched by pouring the solution into water. The mixture was made basic with aqueous NaHCO$_3$ and extracted with ether. The ether extract was washed with water, dried over MgSO$_4$ and concentrated. The residue was chromatographed on silica gel, eluting with 15:1 hexane:ethyl acetate, to afford 2.23 g of the title product as an oil, after removal of the solvent. NMR (CD$_3$OD) δ:1.41 (s, 9H), 7.26 (d, 1 H, J=1 Hz), 8.2 (d, 1H, J=1 Hz), 9.78 (s, 1H).

13b. 5-(1.1-dimethylethyl)-3-thiophenecarboxaldehyde ethyleneglycol acetal

To a solution of 2.23 g of 5-(1,1-dimethylethyl)-3-thiophenecarboxaldehyde, from step 138 above, in 50 mL of cyclohexane was added 1.65 g (26.5 mmol) of ethylene glycol and 25 mg of p-toluene sulfonic acid. The reaction was heated at reflux for 12 hours, and the water of reaction was collected in a Dean-Stark trap. The reaction was cooled to room temperature, and made basic with the addition of saturated NaHCO$_3$ solution, then extracted with ether. The ether layer was washed with water, dried over MgSO$_4$ and concentrated to afford 2.31 g (82% yield) of the title product as an oil. MS 21 3 (M+H)$^+$. NMR (CDCl$_3$) δ:1.37 (s, 9H), 4.86 (s, 4H), 5.72 (s, 1H), 6.87 (d, 1H, J=1 Hz), 7.23 (d, 1H, J=1 Hz).

13c. 2-(1,2,3,4-tetrahydro-6,7-dimethoxy-2-nitronaphthyl)-5-(1,1-dimethylethyl)-3-thiophenecarboxyaldehyde ethyleneglycol acetal To a solution of 1.49 g (7.0 mmol) of 5-(1,1-dimethylethyl)-3-thiophenecarboxaldehyde ethyleneglycol acetal, from 13b above, in 10 mL of THF cooled to −78° C. and stirred under N$_2$ was added 2.8 mL of n-butyllithium (2.5M in hexane, 7.0 mmol), and the reaction was stirred at −78° C. for 10 min and at 0° C. for 50 min. The solution was again cooled to −78° C., and a solution of 1.50 g (6.4 mmol) of 1,2-dihydro-6,7-dimethoxy-3-nitronaphthalene (from step 1b above) in 15 mL of THF was added. The solution was stirred at −78° C. for 2 hours and at −20° C. for 1 hour. The reaction was quenched by the addition of saturated NH$_4$Cl solution, diluted with methylene chloride and water, and extracted with methylene chloride. The organic extract was washed with water, dried over MgSO$_4$ and concentrated. The crude product was dissolved in acetonitrile, treated with a catalytic amount of triethylamine, stirred for 16 hours and concentrated. The residue was chromatographed on silica gel to afford 369 mg (14% yield) of the title product. MS 448 (M+H)$^+$. NMR (CDCl$_3$) δ:1.30 (s, 9H), 2.4–2.5 (m, 2H), 2.8–3.0 (m, 2H), 3.73 (s, 3H), 3.87 (s, 3H), 3.95–4.05 (s, 2H), 4.1–4.2 (m, 2H), 5.05–5.1 (m, 1H), 5.35 (d, 1H, J=6 Hz), 5.72 (s, 1H), 6.54 (s, 1H), 6.57 (s, 1H), 6,79 (s, 1H).

13d. trans-9,10-dimethoxy-2-(1,1-dimethylethyl)-4,5,5a.6,7,11b-hexahydro-1-thia -5-aza-cyclopent-2-ena[c]phenanthrene To a solution of 390 mg (87 mmol) of 2-(1,2,3,4-tetrahydro-6,7-dimethoxy-2-nitronaphthyl) -5-(1,1-dimethylethyl)-3-thiophenecarboxaldehyde ethyleneglycol acetal, from step 13c above, in 10 mL of a 3:1 mixture of acetic acid:water was added 570 mg of Zn dust, and the suspension was stirred at 60° C. for 15 min. The mixture was diluted with methylene chloride and water, made basic by the addition of saturated NaHCO$_3$ solution, and extracted with methylene chloride. The organic extract was washed with brine, dried over MgSO$_4$ and concentrate. The residue was chromatographed on silica gel, eluting with 85:5 methylene chloride:methanol, and the solvent was removed to afford 63 mg (20% yield) of the title product. MS 358 (M+H)$^+$. NMR (CD$_3$OD) δ:1.39 (s, 9H), 1.78–1.9 (m, 1H), 2.16–2.26 (m, 1H), 2.85–3.02 (m, 3H), 3.85 (s, 3H), 3.94 (s, 3H), 3.97 (d, 1H, J=11 Hz), 4.06 (s, 2H), 6.54 (s, 1H), 6.64 (s, 1H), 7.47 (s, 13e. trans-2-(1,1-dimethylethyl)-4,5,5a,6,7,11b-hexahydro-1-thia-5-aza-cyclopent-2-ena [c]phenanthrene-9,10-diol hydrobromide To a solution of 60 mg (0.168 mmol) of 9,10-dimethoxy-2-(1,1-dimethylethyl) -4,5,5a,6,7,11b-hexahydro-1-thia-5-aza-cyclopent-2ena[c]phenanthrene, from step 13d above, cooled to −78° and stirred under N$_2$ was added 168 mg (0.67 mmol) of BBr$_3$ (1.0M in CH$_2$Cl$_2$), and the reaction was stirred for 2 hours and at 0° C. for 2 hours. The solution was again cooled to −78° C., and 2 mL of methanol was added. The solution was stirred at 0° C. for 2 hours, then concentrated, and the residue was dried under vacuum at 60° C. to afford 67 mg (97% yield) of the title product. mp 202–4° C. (dec). MS (M+H)+: 330. NMR (CD$_3$OD) δ: 1.41 (s, 9H), 1.9–2.0 (m, 1H), 2.26–2.4 (m, 1H), 2.85–2.95 (m, 2H), 3.35–3.48 (m, 1H), 4.28 (d, 1 H, J=1 Hz), 4.35 (s, 2H), 6.62 (s, 1H), 6.76 (s, 1H), 7.35 (s, 1H). Anal calc for C$_{19}$H$_{24}$BrNO2S.0.1HBr.0.1H$_2$O: C, 54.30; H, 5.83;N, 3.33; Found: C, 54.05; H, 5.43; N, 3.17.

EXAMPLE 14 trans-2-ethyl-4,5,5a,6,7,11b-hexahydro-1-thia-5-aza-cyclopent-2-ena[c]phenanthrene-9,10-diol hydrobromide Following the procedure of example 1, substituting 2-ethylthiophene (Aldrich Chemical Co.) for the 2-methylthiophene of Example 1c, the title compound was prepared. mp 154°–5° C. MS :302. NMR (CD$_3$OD) δ:1.32 (t, 3H, J=7 Hz), 1.88–2.02 (m, 1H), 2.3–2.4 (m, 1H), 2.75–3.0 (m, 4H), 3.42 (dt, 1H, J=5, J=11 Hz), 44.29 (d, 1H, J=11 Hz), 4.37 (s, 2H), 6.63 (s, 1H), 6.71 (s, 1H), 7.32 (s, 1H). Anal. calc. for C$_{17}$H$_{20}$BrNO$_2$S: C, 51.24; H, 5.11; N, 3.51;found: C, 51.62; H, 5.02; N, 3.45.

EXAMPLE 15 trans-2-propyl-4,5,5a,6,7,11b-hexahydro-1-thia-5-aza-cyclo.oent-2-ena[c]phenanthrene-9,10-diol hydrobromide Following the procedure of example 1, substituting 2-propylthiophene (prepared according to the method given in *Bull. Chem. Soc. Japan*, 52, 1865 (1979)) for the 2-methylthiophene of Example 1c, the title compound was prepared. mp 183°–6° C. MS: 316 (M+H)$^+$. NMR (CD$_3$OD) δ:1.0 (t, 3H, J=7 Hz), 1.72 (sx, 2H, J=7 Hz), 1.88–2.02 (m, 1H), 2.26–2.4 (m, 1H), 2.82 (t, 2H, J=7 Hz), 2.92 (t, 2H, J=6 Hz), 3.36–3.5 (m, 1H), 4.30 (d, 1 H, J=1 1 Hz), 4.36 (s, 2H), 6.62 (s, 1H), 6,71 (s, 1H), 7.32 (s, 1H). High Resolution MS analysis: calc: 316.1371; found: 316.1384.

EXAMPLE 16 trans-2-butyl-4,5,5a,6,7,11b-hexahydro-1-thia-5-aza-cyclopent-2-ena[c]phenanthrene-9,10-diol hydrobromide Following the procedure of example 1, substituting 2-butylthiophene (prepared according to the method given in *Bull. Chem. Soc. Japan*, 52, 1865 (1979)) for the 2-methylthiophene of Example 1c, the title compound was prepared. mp 111°–2° C. MS: 330 (M+H)$^+$. NMR (CD$_3$OD) δ:0.96 (t, 3H, J=7 Hz), 1.35–1.45 (m, 2H), 1.58–1.76 (m, 2H), 1.9–2.0 (m, 1H), 2.05–2.2 (m, 1H) 2.7–30 (m, 4H), 3.41 (dt, 1H, J=6 Hz), 4.28 (d, 1H, J=11 Hz), 4.38 (s, 2H), 6.62 (s, 1H), 6.70 (s, 1H), 7.33 (s, 1H). Anal. calc. for C$_{19}$H$_{24}$BrNO$_2$S.0.2H$_2$O: C, 55.13; H, 5.94; N, 3.38; found: C, 54.97; H, 5.88; N, 3.20.

EXAMPLE 17 trans-2-cyclohexyl-4,5,5a,6,7,11b-hexahydro-1-thia-5-aza-cyclopent-2-ena[c]phenanthrene-9,10-diol hydrobromide Following the procedure of example 1, substituting 2-cyclohexylthiophene (prepared as described in Example 12 above) for the 2-methylthiophene of Example 1 c, the title compound was prepared. mp 195°–6° C. MS: 356. High resolution MS Anal. calc. for C$_{21}$H$_{26}$NO$_2$S: 356.1693; found: 356.1684. NMR (CD$_3$OD) δ:1.35–1.50 (m,6H), 1.7–2.1 (m, 5H), 2.26–2.4 (m, 1H), 2.91 (t, 2H, J=6 Hz), 3.4 (dt, 1H, J=4, J=11 Hz), 4.38 (d, 1 H, J=1 1 Hz), 4.46 (s, 2H), 6.61 (s, 1H), 6,71 (s, 1H), 7.34 (s, 1H).

EXAMPLE 18 trans-4,5,5a,6,7,11b-hexahydro-1-thia-5-aza-cyclopent-2-ena[c]phenanthrene-9,10-diol hydrobromide Following the procedure of Example 13, substituting 3-thiophenecarboxaldehyde for the 5-(1,1-dimethylethyl)-3-thiophenecarboxaldehyde of Example 13b, the title compound was prepared. MS:274 (M+H)$^+$. NMR (CD$_3$OD) δ:1.9–2.05 (m, 1H), 2.3–2.4 (m, 1H), 2.88–2.97 (m, 2H), 3.4–3.5 (m, 1H), 4.36 (d, 1H, J=10 Hz), 4.46 (s, 2H), 6.62 (s, 1H), 7.02 (d, 1H, J-6 Hz), 7.34 (s, 1H), 7.49 (d, 1H, J=6 Hz). Anal. calc. for C$_{15}$H$_{16}$BrNO$_2$S.0.2H$_2$O: C, 50.34; H, 4.68; N, 3.87; found: C, 50.09; H, 4.77; N, 4.13.

EXAMPLE 19 trans-2-phenyl-4,5,5a,6,7,11b-hexahydro-1-thia-5-aza-cyclopent-2-ena[c]phenanthrene-9,10-diol hydrobromide 19a. 5-Bromo-3-thiophenecarboxaldehyde To a solution of 6 g (53.45 mmol) of 3-thiophenecarboxaldehyde in 100 mL of methylene chloride cooled to 0° C. was added 11.8 g of AlCl$_3$, followed by 2.9 mL (56.2 mmol) of Br2. The solution was heated at reflux for 4 hours, the cooled to room temperature, and quenched by pouring into 150 mL of water. The mixture was made basic with satd NaHCO$_3$ solution and extracted with methylene chloride. The organic extract was washed with water, dried over MgSO$_4$ and concentrated. The residue was chromatographed on silica gel, eluting with 10:1 hexane:ethyl acetate, to afford 9.21 g of the title product as an orange oil. NMR (CDCl$_3$) δ:7.51 (d, 1H, J=1 Hz), 8.0 (d, 1H, J=1 Hz), 9.77 (s, 1H).

19b. 5-Bromo-3-thiophenecarboxaldehyde ethylene glycol acetal

To a solution of 8.5 g of 5-bromo-3-thiophenecarboxaldehyde, from step 19a above, in 150 mL of toluene was added 5 mL of ethylene glycol and 85 mg of p-toluenesulfonic acid. The solution was heated at reflux for 4 hours, and the water of reaction was captured in a Dean-Stark trap. The reaction was cooled to room temperature, diluted with water, made basic with satd NaHCO$_3$ solution, and the mixture was extracted with ether. The ether extract was washed with water and brine, and dried over MgSO$_4$. The solvent was removed to afford 10.12 g (96% yield) of the title product as an oil. NMR (CDCl$_3$) δ;3.98–4.1 (m, 4H), 5.81 (s, 1H), 7,11 (d, 1 H, J=1 Hz), 7.30 (d, 1 H, J=1 Hz).

19c. 5-Phenyl-3-thiophenecarboxaldehyde ethylene glycol acetal

To a suspension of 295 mg (0.26 mmol) of tetrakis(triphenylphosphine palladium (0) (Aldrich Chemical Co.) in ethylene glycol dimethyl ether (DME) was added a solution of 3 g of 5-bromo-3-thiophenecarboxaldehyde ethylene glycol acetal, from step 19b above, in 10 mL of DME. The reaction was stirred for 15 min, and a solution of 2.32 g (19.2 mmol) of phenylboric acid (Aldrich Chemical Co.) in ethanol/Na$_2$CO$_3$ was added. The reaction was heated at reflux for 20 hours, then diluted with ether and water and extracted with ether. The extract was washed with water and dried over MgSO$_4$. Removal of the solvent and chromatography of the residue gave 2.46 g (83% yield) of the title product. NMR (CDCl$_3$) δ:4.2–4.4 (m, 4H), 5.89 (s, 1H), 7.2–7.4 (m, 5H), 7.56–7.63 (m, 2H), 19d. trans-2-phenyl-4,5,5a,6,7,11b-hexahydro-1-thia-5-aza-cyc10pent-2ena[c]phenanthrene-9,10-diol hydrobromide Following the procedures of 13c–13e, substituting 5-phenyl-3-thiophenecarboxyaldehyde ethylene glycol acetal for the 5-(1,1-dimethylethyl)-3-thiophenecarboxyaldehyde ethylene glycol acetal of step 13c, the title compound was prepared. mp 236° C. MS (M+H)$^+$350. NMR (CD$_3$OD) δ:1.95–2.05 (m, 1H), 2.3–2.4 (m, 1H), 2.85–3.0 (m, 2H), 3.49 (dt, 1H, J=3, J=7 Hz), 4.39 (d, 1H, J=7 Hz), 4.45 (s, 2H), 6.64 (s, 1H), 7.29 (s, 1H), 7.3–7.42 (m, 4H), 7.6–7.7 (m, 2H). Anal calc for C$_{21}$H$_{20}$BrNO$_2$S+0.3HBr: C, 55.48; H, 4.50, N, 3.08; Found: C, 55.16; H, 4.28; N,3.00.

EXAMPLE 20

(–)-trans-2-propyl-4,5,5a,6,7,11b-hexahydro-3-thia-5-aza-cyclopent-1-ena[c]phenanthrene-9,10-diol hydrobromide Following the procedure of Example 4, substituting the compound from Example 5b for the starting material of Step 4a, the title compound was prepared. mp 155°–162° C. (dec).MS :316 (M+H)$^+$. NMR (CD$_3$OD) δ:1.03 (t, 3H, J=8 Hz 1.75 (sx, 2H, J=8 Hz), 1.9–2.0 (m, 1H), 2.28–2.41 (m, 1H), 2.87 (t, 2H, J=8 Hz), 2.88–3.05 (m, 2H), 3.15–3.27 (m, 1H), 4.02 (d, 1H, J=11 Hz), 4.46 (s, 2H), 6.67 (s, 1H), 6.90 (s, 1H), 7.02 (s, 1H). Anal. calc. for C$_{18}$H$_{22}$BrNO$_2$S.0.7H$_2$O: C, 52.87; H, 5.77; N, 3.43; found: C, 52.87; H, 5.45; N, 3.34. [α]$_D$=–167° (C=1.03, methanol).

EXAMPLE 21 trans-2,3-dimethyl-4,5,5a,6,7,11b-hexahydro-1-thia-5-aza-cyclopent-2-ena[c]phenanthrene-9,10-diol hydrobromide Following the procedures of Example 1, substituting 2,3-dimethyl thiophene (prepared according to *Synthesis*, 10:545, (1972)) for 2-methylthiophene of step 1c, the title compound was prepared. mp 204°–5° C. MS (M+H)$^+$. NMR (CD$_3$OD) δ:7.32 (s, 1H), 6.61 (s, 1H), 4.3–4.2 (m, 3H), 3.4 (m, H), 2.95–2.7 (m, 2H), 2.38 (s, 3H), 2.15–1.9 (m, 2H), 2.05 (s, 3H). Anal. calc. for C$_{18}$H$_{20}$BrNO$_2$S.0.25 HBr: C, 50.73; H, 5.07; N, 3.48; found: C, 50.74; H, 5.20; N, 3.38.

EXAMPLE 22 trans-2-methyl-4,5,5a,6,7,11b-hexahydro-3-thia-5-aza-cyclopent-1-ena[c]phenanthrene-9,10-diol hydrobromide Following the procedure of example 3, substituting 5-methyl-2-thiophenecarboxylic acid (Aldrich) for the 5-ethyl-2-thiophenecarboxylic acid of step 3b, the title compound was prepared. mp 223°–5 ° C. MS 288 (M+H)$^+$. NMR (CD$_3$OD) $\delta$:7.0 (s, 1H), 6.89 (s, 1H), 6.68 (s, 1H), 4.4 (s, 2H), 4.01 (d, 1H, J=11 Hz), 3.20 (m, 1H), 3.02–2.80 (m, 2H), 2.35 (s, 3H), 2.45–2.20 (m, 1H), 2.0–1.85 (m, 1H). Anal. calc. for C$_{16}$H$_{18}$BrNO$_2$S.0.2HBr: C, 49.99; H, 4.77; N, 3.64: found: C, 50.03, H, 4.81;N, 3.59.

EXAMPLE 23

(−)-trans-2-methyl-4,5.5a,6,7,11b-hexahydro-3-thia-5-aza-cyclopent-1-ena[c]phenanthrene-9,10-diol hydrobromide This chiral isomer was prepared from the mixture of compounds from Example 22 by the procedure of Example 4. [$\alpha$]$_D$=−162°, c=1.03 in methanol). mp 201°–2° C. Anal. calc. for C$_{16}$H$_{18}$BrNO$_2$S.0.2HBr: C, 49.47; H, 4.73; N, 3.61; found: C, 49.45; H, 4.72; N, 3.46.

EXAMPLE 24

(−)-trans-2-(1.1 -di methylethyl)-4,5,5a,6,7,11b-hexahydro-3-thia-5-aza-cyclopent-1-ena[c]phenanthrene-9,10-diol hydrobromide This chiral isomer was prepared from the mixture of compounds from Example 6 by the procedure of Example 4. [$\alpha$]$_D$=−193° (C=1.04 in methanol). mp 167°–8° C. Anal. calc. for C$_{19}$H$_{24}$BrNO$_2$S.0.2HBr.0.2H$_2$O: C, 53.05; H, 5.76; N, 3.26; found: C, 53.14; H, 5.67; N, 2.86.

EXAMPLE 25 trans-4,5,5a,6,7,11b-hexahydro-3-thia-5-aza-cyclopent-1-ena[c]phenanthrene-9,10-diol hydrobromide Following the procedure of example 3, substituting 2-thiophenecarboxylic acid (Aldrich) for the 5-ethyl-2-thiophenecarboxylic acid of step 3b, the title compound was prepared. mp. 185° C. MS 274 (M+H)$^+$. NMR (CD$_3$OD) $\delta$:7.59 (d, 1H, J=3 Hz), 7.32 (d, 1H, J=3 Hz), 6.88 (s, 1H), 4.58 (d, 1H, J=8 Hz), 4.52 (d, 1H, J=8 Hz), 4.10 (d, 1H, J=6 Hz), 3.25 (m, 1H), 2.98 (m, 1H), 2.84 (m, 1H), 2.37 (m, 1H), 1.96 (m, 1H). Anal. calc. for C$_{15}$H$_{16}$BrNO$_2$S.0.2HBr: C, 48.17; H, 4.47; N, 3.74; found: C, 47.92; H, 4.51; N, 3.62.

EXAMPLE 26 trans-2-trifluoromethyl-4,5,5a,6,7,11b-hexahydro-3-thia-5-aza-cyclopent-1-ena[c] phenanthrene-9,10-diol hydrobromide Following the procedure of Example 3, substituting 5-trifluoromethyl-2thiophenecarboxylic acid (prepared by the method given in *J. Fluorine Chem.*, 46:445 (1990)) for the 5-ethyl-2-thiophenecarboxylic acid in step 3b, the title compound is prepared.

EXAMPLE 27 trans-2-propyl-4,5,5a,6,7,11b-hexahydro-1-thia-3,5-diaza-cyclopent-2-ena[c]phenanthrene-9,10-diol dihydrobromide

27a. N-Butanoyl-L-cysteine, ethyl ester

A suspension of L-cysteine ethyl ester HCl (10 g, 53.9 mmol) in 120 mL of methylene chloride was treated with pyridine (9.2 mL, 113.4 mmol) and stirred at room temperature for 15 min. DMF (20 mL) was added and the mixture was heated to dissolve the solids. The solution was cooled in an ice bath and treated with butyryl chloride (5.7 mL, 53.9 mmol), stirred at 0° C. for 1 hour and then at room temperature for 1/2 hour. The reaction solution was poured into water, and the mixture was extracted with ethyl acetate. The organic extract was washed with water and brine, dried over Na$_2$SO$_4$, and concentrated to give 11.1 g of an oil. The NMR analysis indicated a 3:1 mixture of the title product and the N,S-dipropionyl analog. The mixture was used without further purification. NMR (CDCl$_3$) for the title compound $\delta$:6.4–6.3 (bs, 1H), 4.92–4.85 (m, 1H), 4.32–4.2 (m, 2H), 3.04 (dd, J=4.5, 9 Hz, 2H), 2.25 (t, J=7 Hz, 2H), 1.7 (q, J=7 Hz, 2H) 1.32 (t, J=7 Hz, 3H), 0.98 (t, J=7 Hz, 3H).

27b. 2-Propyl-4-thiazolinecarboxylic acid, ethyl ester

The crude mixture from step 27a above was dissolved in 60 mL of methylene chloride and 25 mL of POCl$_3$ (270 mmol) was added, and the reaction was stirred at reflux for 3 hours, cooled to room temperature and the solvent removed under vacuum. The residue was dissolved in 100 mL of THF, cooled to −40° C. and treated with NaiI (95%, 2.8 g, 101 mmol). The reaction mixture was stirred at 0° C. for 2 hours, quenched with aqueous satd. NH$_4$Cl, diluted with water and extracted with ether. The extract was washed with water and brine and dried over MgSO$_4$. The crude product was purified via column chromatography on silica gel, eluting with 6:1 hexane:ethyl acetate, to give 5.9 g (55% yield) of the title product after removal of the solvent. MS: 202(M+H)$^+$. NMR (CDCl$_3$) $\delta$:5.1–5.0 (m, 1H), 4.26 (dq, J=1, 8 Hz, 2H), 3.6–3.45 (m, 2H), 2.55 (td, J=1, 9 Hz, 2H), 1.68 (sx, J=9 Hz, 2H), 1.32 (t, J=8 Hz, 3H), 0.98 (t, J=9 Hz, 3H).

27c. 2-propyl-4-thiazolecarboxylic acid, ethyl ester

A mixture of the compound from step 27b (7.1 g, 35.3 mmol) and activated MnO$_2$ (31 g, 353 mmol) in 80 mL of methylene chloride was stirred at reflux for 6 hours. The suspension was filtered, and the filter cake was washed with methylene chloride and methanol. The flitrates were combined and concentrated under vacuum. The residue was dissolved in 500 mL of ether and washed with water and brine and dried over MgSO$_4$. Removal of the solvent gave 5.95 g (85% yield) of the title compound. MS: 200 (M+H)$^+$. NMR (CDCl$_3$) ,$\delta$:8.06 (s, 1H), 4.43 (q, J=8 Hz, 2H), 3.04 (t, J=8 Hz, 2H), 1.9–1.78 (m, 2H), 1.41 (t, J=8 Hz, 3H), 1.03 (t, J=8 Hz, 3H).

27d. 2-propyl-4-thiazolemethanol

A mixture of the compound from step 27c (1.2 g (6 mmol) and NaBH$_4$ (490 mg, 13 mmol) in 15 mL of ethanol was stirred at reflux for 16 hours, then cooled and quenched with water. The mixture was extracted with ether, and the ether extract was washed with water and brine and dried over MgSO$_4$. The solvent was removed under vacuum to give 0.72 g (76% yield) of the title compound. MS: 156(M+H)$^+$, 173(M+NH$_4$)$^{30}$. NMR (CDCl$_3$) ,$\delta$:7.04 (t, J=0.5 Hz, 1H), 4.74 (dd, J=0.5, 6 Hz, 2H), 2.96 (t, J=8 Hz, 2H), 2.70 (t, J=6 Hz, 1H), 1.82 (sx, J=8 Hz, 2H), 1.03 (t, J=8 Hz, 3H).

47

27e. 5-(1,2,3-4-tetrahydro-6,7-dimethoxy-2-nitro-1-naphthyl)-2-propyl-4-thiazolemethanol A solution of 0.76 g (4.8 mmol) of the compound from step 27d in 15 mL of THF was cooled to −78° C., treated with LDA (Aldrich, 6.8 mL, 1.5M in hexane, 1.01 mmol), stirred at −78° C. for 1 hour, then treated with a precooled (−78° C.) solution of 1,2-dihydro-6,7-dimethoxy-2-nitronaphthalene (from Example 1 b, 1.2 g, 4.8 mmol) in 15 mL of THF. The resulting milky suspension was diluted with 10 mL of THF, stirred at −78° C. for 20 min and at 0° C. for 1 hour. The reaction was quenched with aqueous satd. $NH_4Cl$, diluted with water, and the mixture extracted with methylene chloride. The extract was washed with water and brine, dried over $MgSO_4$ and concentrated. The residue was dissolved in acetonitrile, treated with triethylamine (0.1 mL), stirred for 16 hours at room temperature, and concentrated under vacuum. The crude product was purified by chromatography on silica gel, eluting with 6:1–4:1 hexane:ethyl acetate. to give 470 mg (25% yield) of the title compound. MS: 393(M+H)$^+$. NMR (CDCl$_3$) δ: 6.6 (s, 6.41 (s, 1H), 5.12 (d, J=9 Hz, 1H), 4.89 (dt, J=6, 9 Hz, 1H), 4.70 (d, J=6 Hz, 2H), 3.87 (s, 3H), 3.69 (s, 3H), 3.1–2.95 (m, 2H), 2.89 (t, J=8 Hz, 2H), 2.53–2.45 (m, 2H), 2.36 (t, J=6 Hz, 1H), 1.76 (sx, J=8 Hz, 2H), 0.98 (t, J=8 Hz, 3H).

27f. 5-(2-Amino-1,2,3,4-tetrahydro-6,7-dimethoxy-1-naDhthyl)-2-propyl-4-thiazolemethanol Following the procedure of Example 1d, substituting 0.47 g of the compound from step 27e above for the nitro compound in 1d, a 0.34 g sample of the title compound was obtained. MS: 363 (M+H)$^+$. NMR (CDCl$_3$) δ:6.58 (s, 1H), 6.36 (s, 1H), 4.76 (s, 2H), 4.16 (d, J=9 Hz, 1H), 3.87 (s, 3H), 3.67 (s, 3H), 3.05–2.80 (m, 5H), 2.2–2.1 (m, 1H), 1.9–1.7 (m, 3H), 0.99 (t, J=8 Hz, 3H).

27g. trans-9,10-Dimethoxy-2-propyl-4,5,5a,6,7,11b-hexahydro-1-thia-3,5-diazacyclopent-2-ena [c]phenanthrene A −78° C. solution of the compound from step 27f (0.33 g, 0.9 mmol) in 12 mL of methylene chloride was treated with PBr$_3$ (0.3 mL, 2.7 mmol). The cooling bath was removed, and the reaction was stirred at room temperature for 16 hours, then quenched with 20% aqueous NaOH. The mixture was stirred at room temperature for 20 min, poured into water and extracted with methylene chloride. The extract was concentrated, and the residue was purified by chromatography on silica gel, eluting with 5% methanol in methylene chloride. Removal of the solvent and drying afforded 75 mg (24% yield) of the title compound. MS: 345 (M+H)$^+$. NMR (CDCl$_3$) δ:7.2 (s, 1H), 6.66 (s, 1H), 4.24 (s, 2H), 4.05 (d, J=10 Hz, 1H), 3.94 (s, 3H), 3.88 (s, 3H), 3.1–2.85 (m, 5H), 2.3–2.2 (m, 1H), 2.0–1.86 (m, 1H), 1.83 (sx, J=8 Hz, 2H), 1.03 (t, J=8 Hz, 3H).

27h. trans-2-propyl-4,5,5a,6,7,11b-hexahydro-1-thia-3,5-diaza-cyclopent-2-ena[c]phenanthrene-9,10-diol dihydrobromide Following the procedure of Example 1f, a 75 mg sample of the compound from step 27 g above was converted to the title compound (85 mg, 80% yield). mp. 172°–174° C. MS: 317 (M+H)$^+$. NMR (CD$_3$OD) ,δ:7.12 (s, 1H), 6.62 (s, 1H), 4.54 (m, 1H), 4.45 (d, J=12 Hz, 1H), 3.59 (ddd, J=5, 12, 12 Hz, 1H), 3.07 (t, J=8 Hz 2H), 3.05–2.9 (m, 2H), 2.44–2.33 (m, 1H), 2.1–1.95 (m, 1H), 1.87 (sx, J=8 Hz, 2H), 1.05 (t, J=8 Hz, 3H). Anal. Calcd for $C_{17}H_{22}Br2N_2O_2S$: C, 42.69; H, 4.64; N, 5.86; Found: C, 42.56; H, 4.30; N, 5.75.

48

EXAMPLE 28 trans-2-trifluoromethyl-4,5,5a,6,7,11b-hexahydro-1-thia-3.5-diaza-cyclopent-2-ena[c]phenanthrene-9,10-diol dihydrobromide Following the procedures of Example 27, substituting trifluoroacetyl chloride for the butyryl chloride of step 27a, the title compound was prepared. mp 180°–190° C. (dec). HRMS: calcd for $C_{15}H_{13}F_3N_2O_2S$: 343.0728; found: 343.0725. NMR (CD$_3$OD) δ:7.12 (s, 1H), 6.65 (s, 1H), 4.66 (br s, 2H), 4.57 (d, J=11 Hz, 1H), 3.66 (ddd, J=4,11,11 Hz, 1H), 3.05–2.90 (m, 2H), 2.442.35 (m, 1H), 2.10–1.88 (m, 1H).

EXAMPLE 29 trans-2-Propyl-4,5,5a,6,7,11b-hexahydro-1-oxa-3,5-diaza-cyclopent-2-ena[c]phenanthrene-9,10-diol dihydrobromide 29a. 5-Bromo-2-propyl-4-oxazolecarboxylic acid methyl ester The title compound was prepared according to the procedure of Das et al., *Tetrahedron Lett.*, 33:7835, 1992. MS: 248 (M+H)$^+$, 250 (M+H)$^+$, 265 (M+NH$_4$)$^+$, 267 (M+NH$_4$)$^+$. NMR (CDCl$_3$) ,δ:3.53 (s, 3H), 2.78 (t, J=8 Hz, 2H), 1.82 (sx, J=8 Hz, 2H), 1.00 (t, J=8 Hz, 3H).

29b. 5-Bromo-2-propyl-4-oxazolemethanol

A 4.245 g (17.12 mmol) sample of the compound from step 29a above was dissolved in 80 mL of methylene chloride and cooled to 0° C. DIBAL-H (1.0M in hexane, 37.0 mmol) was added via syringe. The resulting solution was stirred for 15 min. Methanol (2 mL) was added slowly, followed by 80 mL of satd. potassium sodium tartrate, and the mixture was stirred for 1 hour. The organic layer was separated, and the aqueous layer was extracted with 2×50 mL of methylene chloride. The organics were combined, dried over MgSO$_4$ and concentrated. The residue was purified by column chromatography on silica gel, eluting with 20–60% ethyl acetate in hexane, to afford 3.490 g (93% yield) of the title product. MS:220(M+H)$^+$, 222(M+H)$^+$, 237(M+NH$_4$)$^+$, 239 (M+NH$_4$)$^+$. NMR (CDCl$_3$) δ:4.50 (s, 2H), 2.72 (t, J=8 Hz, 2H), 2.0 (br s, 1H), 1.79 (sx, J=8 Hz, 2H), 1.00 (t, J=8 Hz, 3H).

29c. 5-Bromo-2-propyl-4-(((2-tetrahydropyranyl)oxy)methyl)oxazole

To a solution of 1.96 g (8.91 mmol) of the compound from step 29b in 55 mL of methylene chloride at room temperature were sequentially added 7 mL of 3,4-dihydro-2H-pyran (76.7 mmol) and 1 g (3.98 mmol) of PPTS. The reaction was stirred at room temperature for 20 min, 30 mL of satd. NaHCO$_3$ was added, and the mixture was stirred for 5 min. The organic layer was separated, and the aqueous layer was extracted with 2×50 mL of methylene chloride. The organics were combined, dried over MgSO$_4$ and concentrated. The residue was purified by flash chromatography on silica gel, eluting with 10–30% ethyl acetate in hexane, to afford, after removal of the solvent and drying, 2.70 g (100% yield) of the title product as a colorless oil. NMR (CDCl$_3$) δ:4.75 (t, J=3 Hz, 1H), 4.57 and 4.33 (ABq, J=12 Hz, 2H), 3.93 (m, 1H), 3.56 (m, 1H), 2.72 (t, J=8 Hz, 2H), 190–1.48 (m, 8H), 1.00 (t, J=8 Hz, 3H).

29d. 5-(1,2,3,4-tetrahydro-6,7-dimethoxy-2-nitro-1-naphthyl)-2-propyl-4-(( (2-tetrahydropyranyl)oxy)methyl)oxazole n-Butyllithium (2.5M in hexane, 10 mmol) was added to a solution of the compound from step 29c (2.70 g, 8.88 mmol) in 40 mL of THF cooled to −78° C. The resulting yellow solution was stirred for 30 min at −78° C., and a solution of 1,2-dihydro-6,7-dimethoxy-3-nitronaphthalene (2.227 g, 9.48 mmol), from Example 1b, precooled to −78° C., was added via cannula. The reaction was stirred for 2 hours at −78° C., then the reaction was quenched by the addition of 10 mL of satd. $NH_4Cl$. After warming to room temperature, the organic layer was separated, and the aqueous layer was extracted with 2×50 mL of methylene chloride. The organics were combined, dried over $MgSO_4$ and concentrated. The crude product was dissolved in 45 mL of methanol and treated with 8 mL of triethylamine. This solution was stirred for 15 hours at room temperature. The solvent was removed under reduced pressure, and the residue was chromatographed on silica gel, eluting with 30–60% ethyl acetate in hexane, to afford after removal of the solvent and drying, 3.64 g (89% yield) of the title product as an oil. MS: 461 $(M+H)^+$. NMR showed a mixture of diastereomers.

29e. trans-5-(2-Amino-1,2,3,4-tetrahydro-6,7-dimethoxy-1-naphthyl)-2-propyl -4-oxazolemethanol To a solution of the compound from step 29d (1.16 g, 2.52 mmol) in 40 mL of ethanol was added 10 mL of 6 N HCl. The mixture was stirred for 30 min at room temperature, and zinc dust was added in portions until the yellow solution turned colorless. Satd. $NaHCO_3$ solution was added until the mixture was at pH 8–9. The solid was removed by filtration and washed with methylene chloride. The flitrate and washings were combined, dried over $MgSO_4$, concentrated, and purified by chromatography on silica gel, eluting with 5–40% methanol (containing 5%$NH_4OH$) in methylene chloride, to afford 742 mg (85% yield) of the title product as a 1:6.5 mixture of cis:trans isomers. Recrystallization from 1:1 hexane:ethyl acetate provided the pure trans isomer as a solid. MS: 347$(M+H)^+$. NMR $(CDCl_3)$ δ:6.62 (s, 1H), 6.29 (s, 1H), 4.62 and 4.52 (abq, J=13 Hz, 2H), 4.02 (d, J=10 Hz, 1H), 3.87 (s, 3H), 3.68 (s, 3H), 3.17 (m, 1H), 3.03–2.79 (m, 2H), 2.65 (t, J=8 Hz, 2H), 2.18 (m, 1H), 1.81 (m, 1H), 1.72 (sx, J=8 Hz, 2H), 0.92 (t, J=8 Hz, 3H).

29f. trans-9,10-Dimethoxy-2-propyl-4,5,5a,6,7.11b-hexahydro-1-oxa-3.5-diazacyclopent -2-ena[c]phenanthrene $PBr_3$ (0.9 mL) was added to a solution of the compound from step 29e above (320 mg, 0.92 mmol) in 25 mL of methylene chloride cooled to −78° C., and the mixture was stirred for 15 min. The cooling bath was removed, and the reaction was stirred for 15 hours. The solution was cooled to 0° C., then quenched by addition of satd. $NaHCO_3$ until a pH of 8–9 was reached. The aqueous layer was separated and extracted with 3×20 mL of methylene chloride. The organics were combined, treated with 10 mL of HCl (1.0M in ether), dried and concentrated to leave a solid residue. The material was dissolved in 70 mL of t-butanol, $K_2CO_3$ (1 g) was added, and the mixture was heated at reflux for 1.5 hours. NaI (1 g) was then added, and the mixture stirred a further 2.5 hours at reflux. The mixture was cooled and filtered, and the solvent was removed under vacuum. The crude product was dissolved in methylene chloride, which was filtered, washed and concentrated. The residue was purified by preparative tlc, eluting with 25:1 methylene chloride:methanol containing 5%$NH_4OH$, to give 151 mg of the title compound as a solid. MS: 329$(M+H)^+$, 346$(M+NH_4)^+$. NMR $(CDCl_3)$ δ:7.45 (s, 1H), 6.64 (s, 1H), 3.95 (m, 3H), 3.91 (s, 3H), 3.87 (s, 3H), 2.99 (m, 3H), 2.81 (t, J=8 Hz, 2H), 2.14 (m, 1H), 1.90 (m, 2H), 1.85 (sx, J=8 Hz, 2H), 1.03 (t, J=8 Hz, 3H).

29a. trans-2-propyl-4,5,5a,6,7,11b-hexahydro-1-oxa-3,5-diaza-cyclopent-2-ena[c]phenanthrene-9,10-diol dihydrobromide Following the procedures of Example 1f, a 120 mg (0.366 mmol) sample of the compound from step 29f above was treated with $BBr_3$ and methanol, and 170 mg of the title product was isolated. mp. 225° C. (dec). MS: 301 $(M+H)^+$, 318 $(M+NH_4)^+$. NMR $(CDCl_3)$ δ: 7.31 (s, 1H), 6.61 (s, 1H), 4.44–4.22 (m, 3H), 3.63 (m, 1H), 3.00 (m, 2H), 2.88 (t, J=8 Hz, 2H), 2.37 (m, 1H), 2.08 (m, 1H), 1.88 (t, J=8 Hz, 2H), 1.04 (t, J=8 Hz, 3H). Anal. Calcd for $C_{17}H_{20}N_2O_3 \cdot 2.3$ HBr$\cdot 1.0$ $H_2O$: C, 40.48; H, 4.86; N, 5.55; Found: C, 40.56; H, 5.08; N, 5.42.

EXAMPLE 30 trans-2-(3-Methylbutyl)-4,5,5a,6,7,11b-hexahydro-1-thia-5-aza-cyclopent-2-ena[c] phenanthrene-9,10-diol hydrobromide 30a. 2-(3-Methylbutyl)thiophene Isopentyl bromide (Aldrich, 8 g, 53mmol) was added to 53 mL of an ice-cooled solution of lithiothiophene (1.0M in THF, 53 mmol). The reaction was stirred at 0° C. for 2 hours, at room temperature for 16 hours, and poured into water, then the mixture was extracted with hexane. The organic layer was dried and concentrated, and the residue was purified by column chromatography on silica gel, eluting with hexane, to give 7.2 g (88% yield) of the title compound as a colorless oil. NMR $(CDCl_3)$ δ:7.10 (dd, J=1, 6 Hz, 1H), 6.90 (dd, J=4, 6 Hz, 1H), 6.78 (dd, J=1, 4 Hz, 1H), 2.84 (t, J=8 Hz, 2H), 1.7–1.5 (m, 3H), 0.94 (d, J=6 Hz, 6H).

30b. trans-2-(3-Methylbutyl)-4,5,5a,6,7,11b-hexahydro-1-thia-5-aza-cyclopent-2-ena[c]phenanthrene-9,10-diol hydrobromide Following the procedures of Example 1, substituting 2-isopentylthiophene, from step 30a above, for the 2-methylthiophene of Example 1 c, the title compound was prepared. mp. 215°–21 9° C. MS: 344 $(M+H)^+$. NMR $(CD_3OD)$ δ: 7.32 (s, 1H), 6,71 (s, 1H), 6.62 (s, 1H), 4.35 (bs, 2H), 4.29 (d, J=11 Hz, 1H), 3.35–3.38 (m, 1H), 2.95–2.80 (m, 4H), 2.4–2.28 (m, 1H), 2.05–1.90 (m, 1H), 1.7–1.55 (m, 3H), 0.95 (d, J=6 Hz, 6H). Anal. Calcd for $C_{20}H_{26}BrNO_2S \cdot 0.3$ $CH_2Cl_2$: C, 54.19; H, 5.96; N, 3.11; Found: C, 54.00; H, 5.76; N, 3.20.

EXAMPLE 31 trans-2-Hexyl-4,5,5a,6,7,11b-hexahydro-1-thia-5-aza-cyclopent-2-ena[c]phenanthrene-9,10-diol hydrobromide Following the procedures in Example 30, substituting n-hexyl iodide for isopentyl bromide in step 30a, the title compound was prepared. mp. 165°–170° C. MS: 358 $(M+H)^+$. NMR $(CD_3OD)$ ,δ:7.32 (s, 1H), 6,7 (s, 1H), 6.61 (s, 1H), 4.37 (s, 2H), 4.31 (d, J=11 Hz, 1H), 3.42 (ddd, J=6,11,11 Hz, 1H), 3.0–2.9 (m, 2H), 2.82 (t, J=7 Hz, 2H), 2.4–2.3 (m, 1H), 2.05–1.9 (m, 1H), 1.72–1.6 (m, 2H), 1.4–1.2 (m, 6H), 0.94 (m, 3H).

EXAMPLE 32 trans-2-Chloro-4,5,5a,6,7,11b-hexahydro-1-thia-5-aza-cyclopent-2-ena[c]phenanthrene-9,10-diol hydrobromide Following the procedures of Example 1c–1f, substituting 2-chlorothiophene for 2-methylthiophene and lithium diisopropylamide for n-butyl lithium in step 1c, the title compound was prepared. mp. 261°–263° C. MS: 308 (M+H)⁺. NMR (CD₃OD) δ:7.18 (s, 1H), 6.95 (s, 1H), 6.52 (s, 1H), 4.39 (s, 2H), 4.33 (d, J=11 Hz, 1H), 3.46 (ddd, J=5,11,11 Hz, 1H), 2.95–2.88 (m, 2H), 2.4–2.27 (m, 1H), 2.05–1.85 (m, 1H). Anal. Calcd for C₁₅H₁₅BrClNO₂S.0.1H₂O: C, 46.14; H, 3.92; N, 3.59; Found: C, 46.02; H, 3.91; N, 3.56.

EXAMPLE 33 trans-2-(1-Cyclopentylmethyl)-4,5,5a,6,7,11b-hexahydro-1-thia-5-aza-cyclopent-2-ena[c]phenanthrene-9,10-diol hydrobromide 33a. 2-Thienyl cyclopentyl ketone Cyclopentanecarboxylic acid chloride, prepared from 100 mmol cyclopentanecarboxylic acid and 120 mmol of thionyl chloride, was dissolved in 100 mL of methylene chloride, and the solution was cooled in an ice bath. Thiophene (13.4 mL, 100 mmol) and SnCl₄ (25 mL of a 1M solution in methylene chloride) were added. The reaction was warmed to room temperature and stirred for 72 hours. The reaction was quenched with 1 N HCl, and the mixture was extracted with three portions of methylene chloride. The organic extract was washed with satd aqueous NaHCO₃, was dried over MgSO₄, and filtered through a pad of silica gel. The solvent was removed by rotary evaporation to give 12.28 g of crude product, which was used without further purification.

33b. 2-Cyclopentylmethythiophene

The material from step 33a above (12.28 g) was dissolved in 100 mL of diethylene glycol. KOH (11.20 g, 200 mmol) was added and dissolved. Hydrazine hydrate (8.25 mL, 170 mmol) was added, and the reaction was heated to gentle reflux for 18 hours. After cooling, the reaction was diluted with water, neutralized with 66 mL of 3 N HCl and extracted with 3×100 mL of hexane. The extract was dried over MgSO₄, filtered through a pad of silica gel and evaporated on a rotary evaporator to give 6.58 g of the title product. NMR (CDCl₃) δ:1.21 (m, 2H), 1.61 (m, 4H), 1.81 (m, 2H), 2.14 (septet, 1H), 2.81 (d, 2H), 6.79 (dd, J=4 Hz, 1H), 6.91 (dd, J=4, 5 Hz, 1H), 7.11 (dd, J=1, 5 Hz, 1H).

33c. trans-2-(1-Cyclopentylmethyl)-4,5,5a,6,7,11b-hexahydro-1-thia-5-aza-cyclopent-2-ena[c]phenanthrene-9,10-diol hydrobromide Following the procedures of Example 1, replacing 2-methylthiophene of step 1c with 2-cyclopentylmethythiophene, prepared in step 33a above, the title compound was prepared. mp. 180°–185° C. MS: 356 (M+H)⁺. NMR (CD₃OD) δ: 7.34 (s, 1H), 6,71 (s, 1H), 6.64 (s, 1H), 4.38 (s, 2H), 4.29 (d, J=11 Hz, 1H), 3.42 (ddd, J=6,11,11 Hz, 1H), 3.0–2.8 (m, 2H), 2.83 (d, J=8 Hz, 2H), 2.4–2.26 (m, 1H), 2.22–2.1 (m, 1H), 2.0–1.55 (m, 7H), 1.35–1.2 (m, 2H). Anal. Calcd for C₂₂H₂₆BrClNO₂S.0.15 HBr.0.15 EtOH: C, 56.19; H, 5.95; N, 3.08; Found: C, 56.37; H, 5.84; N, 2.87.

EXAMPLE 34 trans-2-1sopropyl-4,5,5a,6,7,11b-hexahydro-1-thia-5-aza-cyclopent-2-ena[c]phenanthrene-9,10-diol trifluoroacetate salt 34a. 2-1sopropyl-4-thiophene carboxaldehyde AlCl₃ (4 g, 35.6 mmol) and 2-chloropropane (Aldrich, 1.3 g, 17 mmol) were sequentially added to an ice-cold solution of 3-thiophenecarboxaldehyde (Aldrich Chemical Co.), and the resulting mixture was stirred at room temperature for 16 hours. The reaction mixture was poured onto ice, and the resulting mixture was adjusted to pH 12 with 20% NaOH and extracted 4× with methylene chloride. The organic extract was washed with H₂O and brine, dried over MgSO₄ and concentrated. Column chromatography on silica gel, eluting with 15:1 hexane:ethyl acetate, afforded 310 mg of the title compound. NMR (CDCl₃) δ: 9.82 (s, 1H), 7.92 (s, 1H), 7.24 (s, 1H), 3.2–3.1 (m, 1H), 1.34 (d, J=8 Hz, 6H).

34b. 2-Isopropyl-4-thiophene carboxylic acid

A solution of AgNO₃ (1.01 g, 5.92 mmol) in 10 mL of H₂0 and 15 mL of a solution of KOH (1.63 g, 40.8 mmol) were sequentially added to a solution of 760 mg (4.9 mmol) of 2-isopropyl-4-thiophene carboxaldehyde, from step 34a above, in 25 mL of ethanol. The resulting black mixture was stirred at room temperature for 2 hours and filtered. The filtrate was washed with ether, then acidified with 6N HCl and extracted with ether. The extract was washed with H₂O and brine, dried over MgSO₄ and concentrated to give 680 mg (81%) of the title compound as a yellow solid. mp. 64°–67° C.

34c. trans-2-Isopropyl-4,5,5a,6,7,11b-hexahydro-1-thia-5-aza-cyclopent-2-ena[c]phenanthrene-9,10-diol trifluoroacetate salt Following the procedures in Example 2a–g, substituting 2-isopropyl-4-thiophene carboxylic acid for the 3-thiophene carboxylic acid of step 2a, the title compound was prepared. The compound was further purified on a reverse phase HPLC column, eluting with 50:50 methanol:0.1% TFA. mp. 192°–195° C. MS: 316 (M+H)⁺. NMR (CD₃OD) δ:7.34 (s, 1H), 6,72 (s, 1H), 6.62 (s, 1H), 4.34 (s, 2H), 4.26 (d, J=11 Hz, 1H), 3.45–3.35 (m, 1H), 3.25–3.10 (m, 1H), 2.95–2.85 (m, 2H), 2.4–2.28 (m, 1H), 2.0–1.88 (m, 1H), 0.85 (d, J=6 Hz, 6 H). Anal. Calcd for C₂₀H₂₂F₃NO₄S: C, 54.18; H, 4.95; N, 3.10; Found: C, 54.22; H, 5.02; N, 3.27.

EXAMPLE 35 trans-2-(3-Methylbutyl)-4,5.5a,6,7,11b-hexahydro-3-thia-5-aza-cyclopent-1-ena[c]phenanthrene-9,10-diol hydrobromide 35a. 5-(3-Methylbutyl)-2-thiophenecarboxylic acid, N-t-butyl amide Following the procedure of Example 5a, replacing the 2-propylthiophene of step 5a with 2-(3-methylbutyl)thiophene, prepared in Example 30a, the title compound was prepared. MS: 254 (M+H)⁺, 271 (M+NH₄)⁺. NMR (CDCl₃) δ: 7.24 (d, J=4 Hz, 1H), 6,72 (d, J=4 Hz, 1H), 5.7 (bs, 1H), 2.82 (t, J=8 Hz, 2H), 1.7–1.5 (m, 3H), 1.44 (s, 9H), 0.93 (d, J=6 Hz, 6H).

35b. 3-(2-Amino-6,7-dimethoxy-1,2,3,4-tetrahydronaphthyl)-5-(3-methylbutyl)-2-thiophenecarboxylic acid, N-t-butyl amide Following the procedures of Example 3c–d, the compound from step 35a was converted to the title product. MS: 459 (M+H)⁺. NMR (CDCl₃) δ:6.60 (s, 1H), 6.30 (s, 1H), 6.20 (s, 1H), 4.51 (d, J=10 Hz, 1H), 3.86 (s, 3H), 3.64 (s, 3H), 3.36–3.25 (m, 1H), 3.1–2.8 (m, 2H), 2.70 (t, J=9 Hz, 2H), 2.3–2.2 (m, 1H), 2.0–1.85 (m, 1H), 1.7–1.5 (m, 3H), 1.42 (s, 9H), 0.89 (d, J=6 Hz, 3H), 0.88 (d, J=6 Hz, 3H), 35c. trans-2-(3-Methylbutyl)-4,5,5a,6,7,11b-hexahydro-3-thia-4-oxo-5-aza -9,10-dimethoxy-cyclopent-1-ena[c]phenanthrene To a solution of 1.87 g (4.1 mmol) of the compound from step 35b above in 100 mL of toluene was added toluenesulfonic acid monohydrate (1.55 g, 8.2 mmol), and the reaction was stirred at reflux for 48 hours. The reaction was cooled to room temperature, diluted with ethyl acetate, and washed with aqueous NaHCO$_3$, H$_2$O and brine, then dried over Na$_2$SO$_4$ and concentrated under vacuum. The crude product was crystallized from ethanol to give 0.91 g (60% yield) of the title compound as a white solid. MS: 386 (M+H)$^+$, 403(M+NH$_4$)$^+$. NMR (CDCl$_3$) δ:7.14 (s, 1H), 7.13 (s, 1H), 6.67 (s, 1H), 5.95 (s, 1H), 4.14 (d, J=12 Hz, 1H), 3.94 (s, 3H), 3.88 (s, 3H), 3.75 (ddd, J=3, 12, 12 Hz, 1H), 3.0–2.76 (m, 4H), 2.1–1.9 (m, 2H), 1.7–1.55 (m, 3H), 0.95 (d, J=6 Hz, 6H).

35d. trans-2-(3-Methylbutyl)-4,5,5a,6,7,11b-hexahydro-3-thia-5-aza-9,10-dimethoxy -cyclopent-1-ena[c]phenanthrene Following the procedure of Example 3g, substituting the compound from step 35c for the starting material thereof, the compound of step 35c was converted to the title compound. mp. 110°–112° C. MS: 372 (M+H)$^+$. NMR (CDCl$_3$) δ:7.0 (s, 1H), 6.89 (s, 1H), 6,72 (s, 1H), 4.05 (s, 2H), 3.88 (s, 3H), 3.82 (s, 3H), 3.56 (d, J=11 Hz, 1H), 3.0–2.6 (m, 5 H), 2.3–2.15 (m, 1H), 1.8–1.5 (m, 4H), 0.95 (d, J=6 Hz, 6H). Anal. Calcd for C$_{22}$H$_{29}$NO$_2$S: C, 71.12; H, 7.87; N, 3.77; Found: C, 70.72; H, 7.76; N, 3.75.

35e. trans-2-(3-Methylbutyl)-4,5,5a,6,7,11b-hexahydro-3-thia-5-aza-cyclopent-1-ena[c]phenanthrene-9,10-diol hydrobromide Following the procedures of Example 3h, substituting the compound from step 35d for the starting material thereof, the title compound was prepared. mp. 73°–75° C. MS: 344 (M+H)$^+$. NMR (CDCl$_3$) δ:7.01 (s, 1H), 6.98 (s, 1H), 6.67 (s, 1H), 4.45 (s, 2H), 4.0 (d, J=11 Hz, 1H), 3.28–3.15 (m; 1H), 3.0–2.8 (m, 4H), 2.4–2.25 (m, 1H), 2.0–1.8 (m, 2H), 1.7–1.58 (n, 2H), 0.98 (d, J=6 Hz, 6H). Anal. Calcd for C$_{20}$H$_{26}$BrNO$_2$S.0.5 H$_2$O: C, 55.43; H, 6.28; N, 3.23; Found: C, 55.43; H, 6.29; N, 3.27.

EXAMPLE 36 trans-2-Pentyl-4,5,5a,6,7,11b-hexahydro-3-thia-5-aza-cyclopent-1-ena[c]phenanthrene-9,10-diol hydrobromide Following the procedures of Example 35, substituting 2-pentylthiophene (prepared as in Example 30a starting with pentyl iodide in place of isopentyl bromide) for 2-(3-methylbutyl)thiophene, the title compound was prepared. mp. 78°–80° C. MS: 344 (M+H)$^+$. NMR (CD$_3$OD) ,δ:7.01 (s, 1H), 6.98 (s, 1H), 6.66 (s, 1H), 4.46 (bs, 2H), 4.02 (d, J=11 Hz, 1H),3.3–3.15 (m, 1H),3.05–2.8 (m, 4H), 2.4–2.3 (m, 1H), 2.0–1.9 (m, 1H), 1.8–1.65 (m, 2H), 1.5–1.3 (m, 4H), 0.94 (t, J=6 Hz, 3H), Anal. Calcd for C$_{20}$H$_{26}$BrNO$_2$S.0.8H$_2$O.0.1HBr: C, 53.75; H, 6.25; N, 3.13; Found: C, 53.69; H, 6.12; N, 3.06

EXAMPLE 37 trans-2-(2-Thiophenyl)-4,5,5a,6,7,11b-hexahydro-3-thia-5-aza-cyclopent-1-ena[c] phenanthrene-9,10-diol hydrobromide Following the procedures of Example 35, substituting 2,2'-bithiophene (Aldrich) for 2-(3-methylbutyl)thiophene, the title compound was prepared. mp. 227°–229° C. MS: 356 (M+H)$^+$. NMR (CD$_3$OD) δ:7.42 (dd, J=1, 6 Hz, 1H), 7.32 (dd, J=1, 4 Hz, 1H), 7.08 (dd, J=4,6 Hz, 1H), 6.93 (s, 1H), 6.68 (s, 1H), 4.58 (d, J=15 Hz, 1H), 4.48 (d, J=15 Hz, 1H), 4.1 (d, J=11 Hz, 1H), 3.3–3.2 (m, 1H), 3.05–2.9 (m, 1H), 2.9–2.8 (m, 1H), 2.42–2.3 (m, 1H), 2.05–1.9 (m, 1H). Anal. Calcd for C$_{19}$H$_{18}$BrNO$_2$S$_2$.0.7 H$_2$O: C, 50.83; H, 4.35; N, 3.12; Found: C, 50.80; H, 4.40; N 3.13.

EXAMPLE 38 trans-2-Hexyl-4,5,5a,6,7,11b-hexahydro-3-thia-5-aza-cyclopent-1-ena[c]phenanthrene-9,10-diol TFA salt Following the procedures of Example 35, substituting 2-hexylthiophene for 2-(3-methylbutyl)thiophene, the title compound was prepared. The compound was further purified by reverse-phase HPLC on a semipreparative column, eluting with a 1:1 mixture of methanol:0.1% aqueous TFA. mp. 90°–97° C. (dec). MS: 358 (M+H)$^+$. NMR (CD$_3$OD) δ:7.01 (s, 1H), 6.88 (s, 1H), 6.66 (s, 1H), 4.45 (s, 2H), 4.0 (d, J=11 Hz, 1H), 3.28–3.18 (m, 1H), 2.95–2.85 (m, 4H), 2.4–2.3 (m, 1H), 2.0–1.85 (m, 1H), 1.8–1.65 (m, 2H), 1.5–1.3 (m, 6H), 0.95–0.88 (m, 3H).

EXAMPLE 39 trans-2-(Cyclopentylmethyl)-4,5,5a,6,7,11b-hexahydro-3-thia-5-aza-cyclopent-1-ena[c]phenanthrene-9,10-diol hydrobromide Following the procedures of Example 35, substituting 2-(cyclopentylmethyl)thiophene, from Example 33b, for 2-(3-methylbutyl)thiophene, the title compound was prepared. mp. 198°–205° C. (dec). MS: 356 (M+H)$^+$. NMR (CD$_3$OD) δ:7.02 (s, 1H), 6.89 (s, 1H), 6.68 (s, 1H), 4.45 (s, 2H), 4.02 (d, J=11 Hz, 1H), 3.3–3.15 (m, 1H), 3.05–2.8 (m, 2H), 2.88 (d, J=7 Hz, 2H), 2.4–2.28 (m, 1H), 2.24–2.15 (m, 1H), 2.0–1.4 (m, 7H), 1.35–1.2 (m, 2H). Anal. Calcd for C$_{21}$H$_{26}$BrNO$_2$S.0.2 HBr.0.2EtOH: C, 55.66; H, 5.98; N, 3.03; Found: C, 55.80; H, 5.92; N, 2.92.

EXAMPLE 40 trans-2-Ethyl-4,5,5a,6,7,11b-hexahydro-3-oxa-5-aza-cyclopent-1-ena[c]phenanthrene-9,10-diol hydrochloride 40a. 1,2-Dihydro-6,7-methylenedioxy-3-nitronaphthalene Following the procedures of Example 1a–b, replacing 6,7-dimethoxy-1-tetralone of step 1a with 6,7-methylenedioxy-1-tetralone (prepared as described by Zjawiony and Peterson, *Organic Preparations and Procedures Int.*, 23:163–172, 1991) the title compound was prepared. MS: 220(M+H)$^+$, 237(M+NH$_4$)$^+$. NMR (CDCl$_3$) δ:7.78 (s, 1H), 6.80 (s, 1H), 6,72 (s, 1H), 6.01 (s, 2H), 2.46 (bs, 4H).

40b. trans-2-Ethyl-4,5,5a,6,7,11b-hexahydro-3-oxa-4-oxo-5-aza-9,10-methylenedioxy-cyclopent -1-ena[c] phenanthrene Following the procedures in Example 35a–c, substituting 2-ethylfuran (Aldrich) for the 2-(3-methylbutyl)thiophene of step 35a, and substituting the compound from step 40a above for the 1,2-dihydro-6,7-dimethoxy-3-nitronaphthalene starting material of step 35b, the title compound was prepared. MS: 312(M+H)$^+$, 329 (M+NH$_4$)$^+$. NMR (CDCl$_3$) ,δ:7.09 (s, 1H), 6.64 (s, 1H), 6.47 (s, 1H), 5.97 (m, 2H), 5.44 (bs, 1H), 4.03 (d, J=12 Hz, 1H), 3.77–3.66 (m, 1H), 3.0–2.84 (m, 2H), 2.77 (q, J=8 Hz, 2H), 2.08–1.88 (m, 2H), 1.31 (t, J=8 Hz, 3H).

40c. trans-2-Ethyl-4,5,5a,6,7,11b-hexahydro-3-oxa-5-aza-9,10-methylenedioxycyclopent -1-ena[c]phenanthrene A solution of 40b (218 mg, 0.7 mmol) in 20 mL of THF was added to a suspension of LAH (34 mg, 0.9 mmol) in 20 mL of THF, and the reaction mixture was stirred at reflux for 16 hours. An additional 34 mg of LAH was added, and the reaction was stirred at reflux for 2 hours. The mixture was cooled to room temperature, quenched with solid $Na_2SO_4.10H_2O$, filtered and concentrated. The residue was purified by column chromatography on silica gel, eluting with 70:30 ethyl acetate:hexane to give 80 mg (38% yield) of the title compound after removal of the solvent and drying. NMR (CDCl$_3$) δ: 7.02 (s, 1H), 6.66 (s, 1H), 6.23 (s, 1H), 5.9(m, 2H), 3.92(m, 2H), 3.51 (d, J=11Hz, 1H), 2.86(q, J=7Hz, 2H), 2.7–2.6 (m, 3H), 2.2–2.1 (m, 1H), 1.7–1.5 (m, 1H), 1.20 (t, J=7 Hz, 3H).

40d. trans-2-Ethyl-4,5,5a,6,7,11b-hexahydro-3-oxa-5-aza-cyclopent-1-ena[c]-phenanthrene-9,10-diol hydrochloride The compound from step 40c (80 mg, 0.26 mmol) was dissolved in 5 mL of methylene chloride, and the solution was cooled in an ice bath. BCl$_3$ (2.6 mL of a 1M solution in methylene chloride) was added. The reaction was stirred 2 hours at 0° C., then quenched with 5 mL of methanol. The quenched reaction mixture was allowed to warm to room temperature, then stirred for 16 hours. The solvent was removed by rotary evaporation, and the residue was dried under high vacuum. The dried residue was triturated with diethyl ether, and the product was collected by filtration. A 74 mg sample of the title product was obtained after drying under high vacuum. mp. 252°–255° C. MS: 286 (M+H)$^+$. NMR (CD$_3$OD) δ:7.03 (s, 1H), 6.64 (s, 1H), 6.49 (s, 1 H), 4.38–4.30 (m, 2H), 3.96 (d, J=11 Hz, 1H), 3.3–3.2 (m, 1H), 3.0–2.9 (m, 2H), 2.72 (q, J=8 Hz, 2H), 2.4–2.25 (m, 1H), 2.05–1.88(m, 1H), 1.3 (t, J=8 Hz, 3H). Anal. Calcd for $C_{17}H_2ClNO_3.0.4$ HCl: C, 60.70; H, 6.11; N, 4.16; Found: C, 60.61; H, 5.97; N, 4.06.

EXAMPLE 41 trans-2-ProPyl-4,5,5a,6,7,11b-hexahydro-3-oxa-5-aza-cycLopent-1-ena[c]phenanthrene-9,10-diol hydrochloride Following the procedures of Example 40, substituting 2-propylfuran (K&K) for the 2-ethylfuran of step 40b, the title compound was prepared. mp. 176°–181° C. MS: 300(M+H)$^+$. NMR (CD$_3$OD) δ:7.03 (s, 1H), 6.83 (s, 1H), 6.50 (s, 1H), 4.38–4.32 (m, 2H), 3.97 (d, J=11 Hz, 1H), 3.3–3.2 (m, 1H), 3.0–2.88 (m, 2H), 2.68 (t, J=7 Hz, 2H), 2.4–2.35 (m, 1H), 2.05–1.9 (m, 1H), 1.72 (sx, J=7 Hz, 2H), 1.0 (t, J=7 Hz, 3H). Anal. Calcd for $C_{18}H_{22}ClNO_3.0.7 H_2O$: C, 62.05; H, 6,77; N, 4.02; Found: C, 62.04; H, 6.65; N, 3.95.

EXAMPLE 42 trans-2-Phenyl-4,5,5a,6,7,11b-hexahydro-3-oxa-5-aza-cyclopent-1-ena[c]phenanthrene-9,10-diol hydrochloride Following the procedures of Example 40, substituting 2-phenylfuran (prepared according to Pelter et al., *Synthesis*, 1987:51) for the 2-ethylfuran of step 40b, the title compound was prepared. mp. 210°–215° C. (dec). MS: 334 (M+H)$^+$. NMR (CD$_3$OD) δ:7.76 (dd, 1,6 Hz, 2H), 7.5–5.4 (m, 3H), 7.22 (s, 1H), 7.12 (s, 1H), 6.66 (s, 1H), 4.5 (bs, 2H), 4.05 (d, J=11 Hz, 1H), 3.4–3.3 (m, 1H), 3.0–2.9 (m, 2H), 2.42–2.3 (m, 1H), 2.1–1.95 (m, 1H). Anal. Calcd for $C_{21}H_{20}ClNO_3.0.3$ HCl.0.5 $H_2O$: C, 64.71; H, 5.51; N, 3.59; Found: C, 64.69; H, 5.51; N, 3.59.

EXAMPLE 43 trans-3-Propyl-4,5,5a,6,7,11b-hexahydro-2-thia-5-aza-cyclopent-3-ena[c]phenanthrene-9,10-diol TFA salt 43a. 4-Bromo-2-propyl-3-thiophenecarboxaldehyde To a solution of diisopropylamine (2.7 mL, 19.4 mmol) in 50 mL of THF cooled to −78° C. was added 7.8 mL (2.5M in hexane, 19.4 mmol) of nbutyllithium, and the reaction was stirred for 0.5 hours. To the first solution was added 4.7 g (19.4 mmol) of 3,4-dibromothiophene (Aldrich), then the reaction mixture was stirred for 1 hour at −78° C. Iodopropane (2.8 mL, 29.1 mmol) was then added, the reaction stirred for 10 min at −78° C., then removed for the cooling bath and stirred for 2 hours at room temperature. The reaction was quenched with aqueous satd. NH$_4$Cl, extracted with ether, washed with H$_2$O and brine, and concentrated to give 5.27 g of crude 3,4-dibromo-2-propylthiophene. This compound (5.25 g, 18.5 mmol) was dissolved in 80 mL of ether and cooled to −78° C. n-Butyllithium (7.4 mL, 18.5 mmol) was added dropwise via syringe, and the resulting mixture was stirred at −78° C. for 20 min. DMF was added (1.86 mL, 24.03 mmol), and the reaction was stirred at −78° C. for 1 hour, then poured into water and extracted with ether. The extract was washed with water, dried over MgSO$_4$, and concentrated in vacuo. Silica gel column chromatography afforded 0.63 g of the title compound. NMR (CDCl$_3$) δ:10.07 (s, 1H), 7.09 (s, 1H), 3.20 (t, J=7 Hz, 2H), 1.74 (m, 2H), 1.02 (t, J=7 Hz, 3H).

43b. 4-Bromo-2-propyl-3-thiophenemethanol

A 850 mg (3.6 mmol) sample of the compound from step 43a was dissolved in 20 mL of ethanol and treated with 206 mg (5.4 mmol) of sodium borohydride. The mixture was stirred at room temperature for 1 hour, then quenched with water and extracted with ether. The extract was washed with water, dried over MgSO$_4$, and concentrated in vacuo to give 950 mg of an oil that was taken to the next step without further purification. NMR (CDCl$_3$) δ:7.09 (s, 1H), 4.60 (s, 2H), 2.85 (t, J=7 Hz, 2H), 1.68 (m, 2H), 0.99 (t, J=7 Hz, 3H).

43c. 4-Bromo-3-(methoxy)methoxymethyl)-2-propylthiophene

To a solution of the compound from step 43b above (3.6 mmol) in 20 mL of methylene chloride was added 1.4 mL (8.1 mmol) and 0.46 mL, 6 mmol) of chloromethyl methyl ether. The reaction mixture was stirred at room temperature for 16 hours, diluted with ether, washed with water and brine, then dried over MgSO$_4$ concentrated. The residue was purified by chromatography on silica gel, eluting with 20:1 hexane:ethyl acetate, to afford 754 of the title compound. NMR (CDCl$_3$) δ:7.09 (s, 1H), 4.69 (s, 2H), 4.52 (s, 2H), 3.44 (s, 3H), 2.88–2.82 (m, 2H), 1.75–1.62 (m, 2H), 0.99 (t, J=7 Hz, 3H).

43d. 4-(6,7-Dimethoxy-2-nitro-1,2,3,4-tetrahydronaphthyl)-3-((methoxy) methoxymethyl)-2-propylthiophene Following the procedure of Example 29d, replacing the starting material of Example 29d with the compound from step 43c above, the title compound was prepared. MS: 453 (M+H)$^+$. NMR (CDCl$_3$) δ:6.59 (s, 1H), 6.56 (s, 1H), 6.39 (s, 1H), 5.2–5.15 (m, 1H), 4.91 (d, J=6 Hz, 1H), 4.63 (d, J=6 Hz, 1H), 4.58 (d, J=6 Hz, 1H), 4.48 (d, J=11 Hz, 1H), 4.35 (d, J=11 Hz, 1H), 3.86 (s, 3H), 3.68 (s, 3H), 3.37 (s, 3H), 2.95–2.85 (m, 2H), 2.81 (t, J=7 Hz, 2H), 2.5–2.3 (m, 2H), 1.68 (sx, J=7 Hz, 2H), 0.97 (t, J=7 Hz, 3H).

43e. 4-(2-Amino-6,7-dimethoxy-1,2,3,4-tetrahydronaphthyl)-3-((methoxy) methoxymethyl)-2-propylthiophene Following the procedures of Example 3d, replacing the starting material therein with the compound (380 mg, 0.9 mmol) from step 43d above, the title compound was prepared. MS: 406 (M+H)+. NMR (CDCl3) δ:6.67 (s, 1H), 6.59 (s, 1H), 6.28(s, 1H), 4.58(s, 2H), 4.41 (d, J=11 Hz, 1H), 4.31 (d, J=11 Hz, 1H), 3.9–3.8 (m, 4H), 3.63 (s, 3H), 3.38 (s, 3H), 3.34–3.25 (m, 1H), 2.92–2.8 (m, 4H), 2.15–2.0 (m, 1H), 1.8–1.6 (m, 3H), 0.99 (t, J-7 Hz, 3H).

43f. 9,10-Dimethoxy-3-propyl-4,5,5a,6,7,11b-hexahydro-2-thia-5-aza-cyclopent-3-ena[c]phenanthrene A solution of the compound (0.9 mmol) from step 436 above was dissolved in 10 mL of THF, 0.5 mL of 12 HCl was added, and the mixture was stirred at reflux for 1.5 hours. Removal of the solvent, gave the intermediate chloro compound, which was immediately dissolved in t-butanol, treated with Na2CO3 (1.0 g, 7.1 mmol) and stirred at reflux for 30 min. The mixture was cooled to room temperature, poured into water, and extracted with methylene chloride. The solvent was dried and removed by evaporation. The residue was purified by silica gel chromatography, eluting with methylene chloride:methanol 97:3, to afford 184 mg of the title compound. MS: 344 (M+H)+. NMR (CDCl3) δ:7.23 (s, 1H), 7.10 (d, J=1 Hz, 1H), 6.80 (s, 1H), 4.13 (d, J=15 Hz, 1H), 3.95 (d, J=15 Hz, 1H), 3.88 (s, 3H), 3.87 (s, 3H), 3.71 (d, J=11 Hz, 1H), 3.60–3.52 (m, 1H), 2.88 (t, J=7 Hz, 2H), 2.75–2.65 (m, 2H), 2.22–2.10 (m, 1H), 1.9–1.6 (m, 3H), 1.0 (t, J=7 Hz, 3H).

43g. 3-Propyl-4,5,5a,6,7,11b-hexahydro-2-thia-5-aza-cyclopent-3-ena[c]phenanthrene-9,10-diol trifluoroacetate salt Following the procedures of Example 1 f, substituting the compound of step 43f above for the starting material therein, the title compound was obtained as a mixture of the cis and trans isomers. The mixture was purified by reverse phase HPLC, eluting with 1:1 methanol:0.1%TFA to give the trans isomer. mp. 114°–116° C. MS: 316 (M+H)+. NMR (CD3OD) δ:7.27 (d, J=1 Hz, 1H), 7.11 (s, 1H),6.64(s, 1H),4.43(d,J=14Hz, 1H),4.34(d,J=14Hz, 1H),4.10(d,J=11Hz, 1H), 3.14 (td, J=11,6 Hz, 1H), 2.9–2.75 (m, 4H), 2.35–2.24 (), 1H), 2.0–1.85 (m, 1H), 1.71 (sx, J=7 Hz, 2H), 1.02 (t, J=7 Hz, 3H).

COMPARATIVE EXAMPLE 44

2-propyl-4,5,5a,6,7,11b-hexahydro-1-thia-5-aza-cyc!opent-2-ena[c]phenanthrene-10-ol hydrobromide Following the procedures as described in Example 1 above, substituting 7-methoxy-1-tetralone for the 6,7-dimethoxy-1-tetralone of step 1 a thereof and substituting 2-ethylthiophene for 2-methylthiophene of step 1 c thereof, the title compound was prepared. mp 234°–236° C. MS: 286 (M+H)+. NMR (CD3OD) δ:7.33 (d, 1H, J=3 Hz), 7.04 (d, 1H, J=9 Hz), 6,73 (s, 1H), 6.68 (dd, 1H, J=3, 9 Hz), 4.4–4.3 (m, 3H), 3.5–3.35 (m, 1H), 2.96 (t, 2H, J=7 Hz), 2.88 (q, 2H, J=8 Hz), 2.4–2.3 (m, 1H), 2.05–1.9 (m, 1H), 1.33 (t, 3 H, J=8 Hz). Anal. Calc'd for C17H20BrNO2S.0.3 H2O: C, 54.93; H, 5.58; N, 3.77; Found: C, 54.66; H, 5.22; N, 3.85;

COMPARATIVE EXAMPLE 45

2-(3,Methyl.phenyl)-4,5,5a,6,7,11b-hexahydro-3-thia-5-aza-cyclopent-1-ena[c]phenanthrene-9,10-diol hydrobromide n-Butyllithium (15 mL, 2.5M in hexane, 37.4 mmol) was added dropwise to a solution of 3-bromotoluene (5.8 g, 34.0 mmol) in 50 mL of THF cooled to −78° C. The resulting suspension was stirred at −78° C. for 30 min, treated with trimethyl borate (10.6 g, 102.2 mmol), stirred −78° C. for 10 min, and allowed to warm to room temperature. The reaction mixture was stirred at room temperature for 16 hours, then cooled in an ice bath and acidified to pH 6 with 2N HCl. The mixture was extracted with methylene chloride, and the organic extract was washed with bdne, dried over Na2SO4, and concentrated to yield 4.24 g of 3-methylphenyl boronic acid.

5-Bromo-2-thiophenecarboxaldehyde (5.09 g, 26.2 mmol) was added to a suspension of 907 mg (0.78 mmol) of tetrakis(triphenylphosphine) palladium (0) in 50 mL of DME, and the resulting mixture was stirred at room temperature for 15 min. To this mixture was added a solution of the 3-methylphenyl boronic acid (prepared above) in 10 mL of ethanol and 26 mL of 2M aqueous Na2CO3. The reaction was stirred at reflux for 24 hours, then cooled to room temperature, diluted, and extracted with ether. The organic extract was washed with water and brine, dried over MgSO4, and concentrated. The residue was purified by flash chromatography on silica gel, eluting with 5% ethyl acetate in hexane, to give 4.75 g (90% yield) of 5-(3-methylphenyl)-2-thiophenecarboxaldehyde. MS: 203 (M+H)+ 220 (M+NH4)+. NMR (CDCl3) d: 9.89 (s, 1H), 7.74 (d, 1H, J=5 Hz), 7.55–7.20 (m, 5H), 2.42 (s, 3H).

A solution of 5-(3-methylphenyl)-2-thiophenecarboxaldehyde (prepared immediately above, 4.7 g, 23.3 mmol) was dissolved in 100 mL of ethanol and sequentially treated with a solution of silver nitrate (7.9 g, 116.5 mmol) in 15 mL of water. The suspension was stirred at room temperature for 1 hour, then filtered, and the filter cake was washed with water and ether. The flitrate was separated, and the aqueous layer was acidified with conc. HCl to pH 4. This solution was twice extracted with ether. The extract was dried over MgSO4 and concentrated to give 4.6 g (96% yield) of 5-(3-methylphenyl)-2-thiophenecarboxylic acid. MS: 236 (M+NH4)+. NMR (CDCl3) d: 7.86 (d, 1H, J=5 Hz), 7.5–7.4 (m, 2H), 7.35–7.10 (m, 3H), 2.4 (s, 3H).

Following the procedures of Example 3, steps b–f and h, above, substituting the 5-(3-methylphenyl)-2-thiophenecarboxylic acid (prepared immediately above) for the 5-ethyl-2-thiophenecarboxylic acid of step 3b, the title compound was prepared. mp. 214°–215° C. MS: 364 (M+H)+. NMR (CD3OD) δ:7.6–7.4 (m, 2H), 7.32 (t, 1 H, Hz), 7.16 (d, 1H, J=7 Hz), 6.97 (s, 1H), 6.68 (s, 1H), 4.56 (m, 2H), 4.10 (d, 1H, J=11 Hz), 3.3–3.2 (m, 1H), 3.1–2.8 (m, 2H), 2.40 (s, 3H), 2.4–2.2 (m, 1H), 2.05–1.9 (m, 1H). Anal. Calc'd for C22H22BrNO2S.0.2 HBr: C, 57.37; H, 4.86; N, 3.04; Found: C, 57.16; H, 4.89; N, 3.05;

COMPARATIVE EXAMPLE 46

2-(4-Methylphenyl)-4,5,5a,6,7,11b-hexahydro-3-thia-5-aza-cyclopent-1-ena[c]phenanthrene-9,10-diol hydrobromide Following the procedures as described in Example 45 above, substituting 4-bromotoluene for the 3-bromotoluene thereof, the title compound was prepared. mp 225°–226° C. MS: 364(M+H)+. NMR (CD3OD) δ:7.58 (d, 2H, J=8 Hz), 7.52 (s, 1H), 7.25 (d, 2H, J=8 Hz), 6.97 (s, 1H), 6.68 (s, 4.5S (m, 2H), 4.10 (d, 1H, J=11 Hz), 3.25–3.20 (m, 1H), 3.1–2.8 (m, 2H), 2.38 (s, 3H), 2.4–2.2 (m, 1H), 2.03–1.9 (m, 1H). Anal. Calc'd for C22H22BrNO2S.0.3 HBr: C, 56.38; H, 4.80; N, 2.99; Found: C, 56.60; H, 4.77; N, 2.98;

COMPARATIVE EXAMPLE 47

2-(Adamantyl)-4,5,5a,6,7,11b-hexahydro-3-thia-5-aza-cyclopent-1-ena[c]phenanthrene-9,10-diol hydrobromide Following the procedures as described in Example 6 above, substituting 1-chloroadamantane for the t-butyl bromide of step 68 thereof, the title compound was prepared. mp 237°–238° C. MS: 408 (M+H)$^+$. NMR (CD$_3$OD) ,δ:6.99 (s, 1H), 6.88 (s, 1H), 6.68 (s, 1H), 4.46 (s, 2H), 4.05 (d, 1 H, J=11 Hz), 3.28–3.15 (m, 1H), 3.05–2.8 (m, 2H), 2.42–2.30 (m, 1H), 2.2–1.75 (m, 16H). Anal. Calc'd for C$_{25}$H$_3$.BrNO$_2$S.0.3 HBr: C, 58.88; H, 5.94; N, 2.69; Found: C, 58.56; H, 5.95; N, 2.73;

EXAMPLE 48

(−)-trans-9,10-Diacetyloxy-2-propyl-4,5,5a,6,7,11b-hexahydro-3-thia-5-aza-cyclopent-1-ena[c]phenanthrene hydrochloride A suspension of (−)-trans-2-propyl-4,5,5a,6,7,11b-hexahydro-3-thia-5-aza-cyclopent-1-ena[c]phenanthrene-9,10-diol hydrobromide (the compound of Example 20) (50.6 mmol) in TFA (170 mL) was treated with acetyl chloride (16.2 mL, 228 mmol) resulting in a clear solution. The reaction was stirred at room temperature for 3 hours, then concentrated in vacuo. The crude product was partitioned between chloroform (700 mL) and sat. aq NaHCO$_3$ (300 mL). The organic layer was washed with aq. NaHCO$_3$ (250 mL), brine (250 mL), dried over sodium sulfate and concentrated to give 28.1 g of a tan foamy solid (theor. yield 20.2g). The compound was then treated with ethereal HCl, resulting in a white precipitate which was collected via vacuum filtration. mp. 234°–237° C. MS: 400 (M+H)$^+$. NMR (DMSO-D6) δ:7.19 (s, 2H), 6.99 (s, 1H), 4.47 (d, J =15Hz. 1H), 4.35 (d, J=15 Hz, 1H), 4.16 (d, J=11Hz, 1H), 3.30–3.20 (m, 1H), 3.0–2.90 (m, 2H), 2.86–2.75 (m,2H), 2.28 (s, 3H), 2.26 (s, 3H), 2.40–2.25 (m, 1H), 2.05–1.90 (m, 1H), 1.65 (sextet, J=8Hz, 2H), 0.95 (t, J=8 Hz, 3H). Anal. calc. for C$_{22}$H$_{26}$ClNO$_4$S: C, 60.61; H, 6.01; N, 3.21; Found: C, 60.55; H, 6.04; N, 3.18. [α]$_D$=−228° (c=1.25, methanol).

EXAMPLE 49 trans-2-chloro-4,5,5a,6,7,11b-hexahydro-3-thia-5-aza-cyclopent-2-ena[c]phenanthrene-9,10-diol hydrobromide Following the procedures of Example 35, substituting 2-chlorothiophene for the 2-(3-methylbutyl)thiophene in step 35a, the title compound was prepared. mp 255°–257° C. MS: 308 (M+H)$^+$. NMR (CD$_3$OD) δ:7.24 (s, 1H), 6.81 (s, 1H), 6.67 (s, 1H), 4.52–4.40 (m, 2H), 4.04 (d, J=11 Hz, 1H), 3.30–3.18 (m, 1H), 3.02–2.77 (, 2H), 2.40–2.28 (m, 1H), 2.00–1.85 (m, 1H). Anal. calc. for C$_{15}$H$_{15}$BrClNO$_2$S: C, 46.35; H, 3.89; N, 3.60; Found: C, 46.14; H, 3.81; N, 3.40.

EXAMPLE 50 trans-2-isopropyl-4,5,5a,6,7,11b-hexahydro-1-oxa-3,5-diaza-cyclopent-2-ena[c]phenanthrene-9,10-diol dihydrobromide Following the procedures of Example 29 steps b–g, substituting 5-bromo-2isopropylcarboxylic acid methyl ester for the 5-bromo-2-propylcarboxylic acid methyl ester in step 29b, the title compound was prepared. mp 220°–222° C. MS: 301 (M+H)$^+$. NMR (CD$_3$OD) δ:7.31 (s, 1H), 6.62 (s, 1H), 4.45–4.20 (m, 3H), 3.68–3.55 (s, 1H), 3.24 (septet, J=6 Hz, 1H), 3.05–2.95 (m, 2H), 2.42–2.30 (m, 1H), 2.15–1.98 (m, 1H), 1.44 (d, J=6 Hz, 6H). Anal. calc. for C$_{19}$H$_{20}$Br$_2$N$_2$O$_3$.H$_2$O: C, 42.52; H, 5.04; N, 5.83; Found: C, 42.72; H, 5.21; N, 5.84.

EXAMPLE 51 trans-2-methyl-4,5,5a,6,7,11b-hexahydro- !-oxa-3.5-diaza-cyclopent-2-ena[c]phenanthrene-9,10-diol dihydrobromide Following the procedures of Example 29 steps b–g, substituting 5-bromo-2-methylcarboxylic acid methyl ester for the 5-bromo-2-propylcarboxylic acid methyl ester in step 29b, the title compound was prepared. mp 224°–230° C. MS: 273 (M+H)$^+$. NMR (CD$_3$OD) δ:7.31 (s, 1H), 6.61 (s, 1H), 4.42–4.20 (m, 3H), 3.72–3.56 (m, 1H), 3.04–2.95 (m, 2H), 2.58 (s, 3H), 2.4–2.3 (m, 1H), 2.15–1.98 (m, 1H). Anal. calc. for C$_{15}$H$_{17}$Br$_2$N$_2$O$_3$.0.8H$_2$O: C, 40.17; H, 4.40; N, 6.25; Found: C, 40.19; H, 4.40; N, 6.11.

EXAMPLE 52 trans-3-propyl-4,5,5a,6,7,11b-hexahydro-1-thia-5-aza-cyclopent-2-ena[c]phenanthrene-9,10-diol hydrochloride 52a. 3-bromo-4-(1-oxopropyl)thiophene A solution of 3,4-dibromothiophene (6.0 g, 24.8 mmol) in 10 mL of ether was cooled to −78° C. and trated with n-butyllithium (9.92 mL, 2.5M solution in hexanes, 24.8 mmol). While holding the temperature at −78° C., the reaction was stirred for 15 minutes, then 2.9 g (24.8 mmol) of N-methyl-N-methoxypropionamide was added and the reaction was stirred for 1 hour. The reaction was quenched with satd NH$_4$Cl, and the mixture was diluted with ether. The ether layer was separated, washed with water and brine, dried over MgSO$_4$ and concentrated. The residue was triturated with hexanes, and the mixture was filtered. The solvent was removed to give 2.08 g of a tan solid. MS 236, 238 (M+NH$_4$)$^+$. NMR (CDCl$_3$) δ:7.99 (d, J=3 Hz, 1H), 7.32 (d, J=3 Hz, 1H), 2.98 (q, J=7 Hz, 2H), 1.21 (t, J=7 Hz, 3H).

52b. 3-bromo-4-propylthiophene

Following the procedure of Example 10a, substituting 3-bromo-4-(1-oxopropyl)thiophene, from step 52a above, for the 2,2-dimethyl-1-thiophenyl-1-propanone in step 10a, the title compound was prepared in 66% yield. NMR (CDCl$_3$) δ:7.22 (d, J=3 Hz, 1H), 6.95 (d, J=3 Hz, 1H), 2.56 (t, 7.5 Hz, 2H), 1.65 (sextet, J=7.5 Hz, 2H), 0.98 (t, J=7.5 Hz, 3H).

52c. 1-(3-bromo-4-propyl-2-thiophenyl)-1,2,3,4-tetrahydro-6,7-methylenedioxy-2-naphthylamine Following the procedure of Example 1, steps c and d, substituting lithium diisopropylamine for n-butyllithium and 1,2-dihydro-6,7-methylenedioxy-3nitronaphthalene, from Example 40a, for 1,2-dihydro-6,7-dimethoxy-3-nitronaphthalene in step 1 c, the title compound was prepared. MS 394, 396 (M+H)$^+$. NMR (CDCl$_3$) δ:6.92 (s, 1H), 6.57 (s, 1H), 6.28 (s, 1H), 5.87 (s, 2H), 4.22 (d, J=9 Hz, 1H), 3.33–3.23 (m, 1H), 3.0–2.8 (m, 2H), 2.62–2.55 (m, 2H), 2.15–2.05 (m, 1H), 1.82–1.6 (m, 3H), 1.02 (t, J=7 Hz, 3H).

52d. 1-(4-propyl-2-thiophenyl)-1,2,3,4-tetrahydro-6,7-methylenedioxy-2-naphthylamine A solution (0.78 g, 1.96 mmol) of 1-(3-bromo-4-propyl-2-thiophenyl)-1,2,3,4-tetrahydro-6,7-methylenedioxy-2-naphthylamine in ethanol was hydrogenated at 4 Atm $H_2$ with 0.3 g of 10% Pd/C catalyst. The catalyst was removed by filtration, and the flitrate was concentrated to give 0.65 g of the title compound. NMR ($CDCl_3$) δ:6.81 (s, 1H), 6,77 (s, 1H), 6.56 (s, 1H), 6.41 (s, 1H), 5.87 (s, 2H), 3.90 (d, J=8 Hz, 1H), 3.25–3.15 (m, 1H), 2.92–2.78 (m, 2H), 2.54 (t, J=7 Hz, 2H), 2.13–2.05 (m, 1H), 1.8–1.6 (m, 3H), 0.96 (t, J=7 Hz, 3H).

52e. trans-3-propyl-4,5,5a,6,7,11b-hexahydro-1-thia-5-aza-cyclopent-2-ena[c]phenanthrene-9,10-diol hydrochloride Following the procedures in Examples 1e and 40d, 1-(4-propyl-2-thiophenyl) -1,2,3,4-tetrahydro-6,7-methylenedioxy-2-naphthylamine, from step 52d above, was converted to the title compound. mp >170° C. (dec). HRMS calcd. for $C_{18}H_{22}NO_2S$: 316.1371;found: 316.1365. NMR ($CD_3OD$) δ:7.35 (s, 1H), 7.13 (s, 1H), 6.63 (s, 1H), 4.36 (s, 2H), 4.33 (d, J=11 Hz, 1H), 3.50–3.35 (m, 1H), 3.0–2.85 (m, 2H), 2.52 (t, J=7 Hz, 2H), 2.40–2.28 (m, 1H), 2.04–1.90 (m, 1H), 1.67 (sextet, J=7 Hz, 2H), 0.99 (t, J=7 Hz, 3H).

EXAMPLE 53 trans-2-propyl-4,5,5a,6,7,11b-hexahydro-1,5-diaza-3-oxa-cyclopent-1-ena[c]phenanthrene-9,10-diol dihydrobromide 53a. 2-propyl-4-(((2-tetrahydropyranyl)oxy)methyl)oxazole-5-carboxylic acid, methyl ester To a solution of 5-bromo-2-propyl-4-(((2-tetrahydropyranyl)oxy)methyl)oxazole (2.376 g, 7.82 mmol), prepared as in Example 29c, in 60 mL of THF and cooled to −78° C. was added n-buthylithium (8.75 mmol). The resulting solution was stirred for 30 minutes at −78° C., and 1.0 mL (12.9 mmol) of methyl chloroformate was added. The reaction mixture was stirred at −78° C. for 5 minutes and at 0° for 30 minutes. The reaction was quenched by the addition of satd $NaHCO_3$, the layers were separated, and the aqueous layer extracted with methylene chloride. The organic extracts were combined, dried, and concentrated. The residue was chromatographed on silica gel, eluting with 10 to 25% ethyl acetate in hexane, to afford 1.660 g of the title compound as an oil. MS m/z: 284 $(M+H)^+$. NMR ($CDCl_3$) δ:4.95 (d, J=12 Hz, 1H), 4.82 (t, J=3 Hz, 1H), 4.67 (d, J=12 Hz, 1H), 3.94 (m, 1H), 3.92 (s, 3H), 3.57 (m, 1H), 2.80 (t, J=7.5 Hz, 2H), 1.84 (sextet, J=7.5 Hz, 2H), 1.80–1.50 (m, 6H), 1.05 (t, J=7.5 Hz, 3H).

53b. 2-propyl-4-(((2-tetrahydropyranyl)oxy)methyl)oxazole-5-methanol

To a solution of 2-propyl-4-(((2-tetrahydropyranyl)oxy)methyl)oxazole-5-carboxylic acid, methyl ester (1.68 g, 5.94 mmol), from step 53a above, in 60 mL of methylene chloride cooled to −78° C. was added DIBAL (1.0M in hexane, 15 mmol). The reaction mixture was then stirred for 15 minutes at 0° C., and methanol (1.5 mL) was added carefully to quench the reaction. Saturated potassium sodium tartrate (50 mL) was added, and the mixtrue was stirred for 1 hour at room temperature. The layers were separated, and the aqueous layer was extracted with methylene chloride. The organic solutions were combined, dried over $MgSO_4$ and concentrated. The residue was chromatographed on silica gel, eluting with 20% ethyl acetate in hexane to 3% methanol in ethyl acetate, to afford 1.27 g of the title compound as an oil. MS m/z: 256 $(M+H)^+$. NMR ($CDCl_3$) δ:4.72–4.51 (m, 5H), 3.85 (m, 1H), 3.55 (m, 1H), 2.97 (t, J=6 Hz, 1H), 2.71 (t, J=7.5 Hz, 2H), 1.90–1.50 (m, 8H), 0.99 (t, J=7.5 Hz, 3H).

53c. 2-propyl-4-(((2-tetrahydropyranyl)oxy)methyl)oxazo! e-5-methanol, pivaloyl ester A 1.645 g (6.45 mmol) sample of 2-propyl-4-(((2-tetrahydropyranyl)oxy)methyl)oxazole-5-methanol, from step 53b above, was dissolved in 15 mL of pyddine and cooled to 0° C. Pivaloyl chloride (1.2 mL, 9.74 mmol) was added, and the mixture was stirred at 0° C. for 10 minutes and at room temperature for 16 hours. The mixture was diluted with ethyl acetate and filtered. The flitrate was concentrated to a small volume, heptane was added, and the solvents again removed. The residue was taken directly to the next step. MS m/z: 340 $(M+H)^+$. NMR ($CDCl_3$) δ:5.13 (s, 2H), 4.74 (t, J=3 Hz, 1H), 4.71 (d, J=12 Hz, 1H), 4.44 (d, J=12 Hz, 1H), 3.89 (m, 1H), 3.55 (m, 1H), 2.72 (t, J=7.5 Hz, 2H), 1.88–1.48 (m, 8H), 1.19 (s, 9H), 0.98 (t, J=7.5 Hz, 3H).

53d. 5-Divaloyloxymethyl-2-propyloxazole-4-methanol

The crude product from step 53c above was dissolved in 20 mL of methanol. A solution of HCl in dioxane (4.0M, 8 mL, 32 mmol) was added, and the mixture was stirred for 15 minutes at room temperature. The solvent was removed, and the residue was dissolved in 30 mL of methylene chloride and extracted with satd $NaHCO_3$. The organic layers were dried over $MgSO_4$ and concentrated. The residue was chromatographed on silica gel, eluting with ethyl acetae, to afford 1.43 g of the title compound. MS m/z: 256 $(M+H)^+$. NMR ($CDCl_3$) δ:5.13 (s, 2H), 4.64 (d, J=6 Hz, 2H), 2.87 (t, J=6 Hz, 1H), 2.71 (t, J=7.5 Hz, 2H), 1.79 (sextet, J=7.5 Hz, 2H), 1.18 (s, 9H), 0.98 (t, J=7.5 Hz, 3H).

53e. 5-pivaloyloxymethyl-2-propyloxazole-4-carboxaldehyde

Swern oxidation (*J. Org. Chem.*, 43:2480 (1978)) of the compound from step 53d above (1.421 g, 5.57 mmol) provided 1.458 g of the title product, which was taken to the next step without further purification. NMR ($CDCl_3$) δ:10.00 (s, 1H), 5.37 (s, 2H), 2.78 (t, J=7.5 Hz, 2H), 1.83 (sextet, J=7.5 Hz, 2H), 1.22 (s, 9H), 1.01 (t, J=7.5 Hz, 3H).

53f. 4-(2-nitroethenyl)-5-pivaloyloxymethyl-2-propyloxazole

The aldehyde from step 53e above was dissoved in 20 mL of THF and 30 mL of t-butanol, and the solution was cooled to 0° C. Nitromethane (15 mL) and potassium t-butoxide (0.5 g) were added, and the reaction mixture was stirred at 0° C. for 10 minutes and at room temperature for 10 minutes. Saturated $NH_4Cl$ solution and hexane were added, and the layers were separated. The aqueous layer was extracted with hexane, and the organic extracts were combined. The extract was dried over $MgSO_4$ and concentrated. The residual oil was dissolved in 40 mL of methylene chloride and added via cannula to a freshly prepared solution of methanesulfonyl chloride (16.8 mmol) and triethylamine (17.2 mmol) in 50 mL of methylene chloride cooled to −78° C. The reaction mixture was stirred for 1 hour at 0° C. and at room temperature for 30 minutes, then filtered through silica gel. The solvent was removed, and the residue was chromatographed on silica gel, eluting with 20% ethyl acetate in hexane, to provide 1.435 g of the the title compound. MS m/z: 297 (M+H)+, 314 $(M+NH_4)^+$. NMR ($CDCl_3$) δ:7.92 (d, J=13 Hz, 1H), 7.73 (d, J=13 Hz, 1H), 5.18 (s, 2H), 2.76 (t, J=7.5 Hz, 2H), 1.81 (sextet, J=7.5 Hz, 2H), 1.23 (s, 9H), 1.01 (t, J=7.5 Hz, 3H).

53g. 1-iodo-4,5-dimethoxy-2-(2-(2-tetrahydropyranyloxy)ethyl)benzene

The title compound was prepared in two steps from 3,4-dimethoxyphenethyl alcohol by standard procedures (Janssen and Wilson, *Org. Synth. Coll.*, Vol. IV, p547 (1963), and Gdeco et al., *J. Org. Chem.*, 42:3772 (1977)). NMR (CDCl$_3$) δ:7.21 (s, 1H), 6.84 (s, 1H), 4.61 (t, J=4 Hz, 1H), 3.90 (m, 1H), 3.87 (s, 3H), 3.86 (s, 3H), 3.79 (m, 1H), 3.59 (m, 1H), 3.48 (m, 1H), 2.98 (t, J=7.5 Hz, 2H), 1.90–1.45 (m, 6H).

53h. 4,5-dimethoxy-2-(2-nitro-1-(5-pivaloyloxymethyl-2-propyl-4-oxazolyl) ethyl)benzeneethanol To a solution of 2.926 g (7.46 mmol) of 1-iodo-4,5-dimethoxy-2-(2-(2-tetrahydropyranyloxy)ethyl)benzene from step 53g above, dissolved in 50 mL of THF and cooled to −78° C. was added dropwise 14.5 mmol of t-butyllithium. The resulting mixture was stirred for 30 minutes at −78° C., then cooled further to −100° C. (ether/liq. N$_2$). To this solution was added via a cannula a −78° C. solution of 4-(2-nitroethenyl)-5-pivaloyloxymethyl-2-propyloxazole (4.1 mmol in 50 mL of THF), from step 53f above, and the reaction was stirred at −78° C. for 30 minutes. The reaction was quenched by addition of satd NH$_4$Cl solution, and the mixture was allowed to warm to room temperature. The layers were separated, the aqueous layer was extracted with methylene chloride, and the organic extracts were combined. The extract was dried over MgSO$_4$ and concentrated. The residual oil was dissolved in 50 mL of methylene chloride and 3 mL of methanol and treated with 3 mL of HCl in dioxane (4.0M, 16 mmol). The mixture was stirred for 30 minutes at room temperature, and 50 mL of satd NaHCO$_3$ was added carefully. The layers were separated, the aqueous layer was extracted with methylene chloride, and the organic extracts were combined. The extract was dried over MgSO$_4$ and concentrated. The residue was chromatographed on silica gel, eluting with 1:1 ethyl acetate:hexane to afford 0.98 g of the title compound. MS m/z: 479 (M+H)$^+$. NMR (CDCl$_3$) δ:7.12 (s, 1H), 6,70 (s, 1H), 5.24–5.07 (m, 3H), 4.92 (d, J=13 Hz, 1H), 4.69 (dd, J=12, 4.5 Hz, 1H), 3.92 (m, 2H), 3.86 (s, 3H), 3.81 (s, 3H), 3.0 (m, 2H), 2.72 (t, J=7.5 Hz, 2H), 2.15 (t, J=6 Hz, 1H), 1.78 (sextet, J=7.5 Hz, 2H), 1.14 (s, 9H), 0.97 (t, J=7.5 Hz, 3H).

53i. trans-1,2,3,4-tetrahydro-6,7-dimethoxy-2-nitro-1-(5-pivaloyloxymethyl-2-propyl -4-oxazolyl)-naphthalene To a solution of 4,5-dimethoxy-2-(2-nitro-1-(5-pivaloyloxymethyl-2-propyl-4-oxazolyl)ethyl) benzeneethanol, from step 53h above, (0.875 g, 1.83 mmol) in 35 mL of methylene chloride cooled to 0° C. were added sequentially 1.94 mmol of CBr$_4$ and 2.0 mmol of 1,2-bis(diphenylphosphino)ethane. The reaction mixture was stirred for 30 minutes at 0° C., and 0.6 mmoles additional of each reagent were added, then stirring was continued at 0° C. for 1.5 hours. The mixture was filtered through silica gel, and the flitrate was concentrated. The residue was dissolved in 100 mL of methylene chloride and stirred with 1.25 mL (8.35 mmol) of DBU for 2 hours at room temperature. The mixture was concentrated, and the residue was chromatographed on silica gel, eluting with 20–50% ethyl acetate in hexane to afford 444 mg of the crude product, which was taken directly to the next step. MS m/z: 461 (M+H)$^+$. NMR (CDCl$_3$) δ:6.59 (s, 1H), 6.32 (s, 1H), 5.10 (m, 2H), 4.91 (d, J=13 Hz, 1H), 4.79 (d, J=9 Hz, 1H), 3.84 (s, 3H), 3.68 (s, 3H), 3.15–2.85 (m, 3H), 2.70 (t, J=7.5 Hz, 2H), 2.50 (m, 1H), 1.73 (sextet, J=7.5 Hz, 2H), 1.20 (s, 9H), 0.90 (t, J=7.5 Hz, 3H).

53j. trans- 1,2,3,4-tetrahydro-6,7-dimethoxy-1-(5-hydroxymethyl-2-propyl-4-oxazolyl) -2-naphthaleneamine DIBAL (3.0 mmol) was added to a cooled solution of the compound from step 53i above (0.957 mmol) in 20 mL of methylene chloride at −78° C. The reaction was stirred for 30 minutes, then 0.5 mL of methanol was added carefully.

The mixture was warmed to room temperature, 20 mL of a satd potassium sodium tartrate solution was added, and the mixture stirred for 1 hour at room temperature. The organic layer was separated, dried over MgSO$_4$ and concentrated. The residue was dissolved in 20 mL of methanol, to which was added triethyl amine, and the mixture was then stirred at room temperature for 16 hours. The solvent was removed, and the residue was reduced with Zn/HCl, by the procedure described in Example 1 d above to produce 300 mg of the title compound. MS m/z: 347 (M+H)$^+$. NMR (CDCl$_3$) ,δ:6.59 (s, 1H), 6.22 (s, 1H), 4.74 (d, J=13 Hz, 1H), 4.55 (d, J=13 Hz, 1H), 4.09 (d, J=10 Hz, 1H), 3.84 (s, 3H), 3.66 (s, 3H), 3.49 (m, 1H), 3.10–2.82 (m, 2H), 2.72 (m, 2H), 2.35 (m, 1H), 2.03 (m, 1H), 1.76 (sextet, J=7.5 Hz, 2H), 0.93 (t, J=7.5 Hz, 3H).

53k. trans-2-propyl-4,5,5a,6,7,11b-hexahydro-9,10-dimethoxy-1,5-diaza-3-oxa-cyclopent -1-ena[c]phenanthrene The compound from step 53j above was converted to the tetracyclic title compound by means of the procedure described in Example 29f. MS m/z: 329 (M+H)$^+$. NMR (CDCl$_3$) δ:8.18 (s, 1H), 6.62 (s, 1H), 4.10–3.90 (m, 2H), 3.93 (s, 3H), 3.85 (s, 3H), 3.66 (d, J=1 0 Hz, 1H), 3.00 (m, 2H), 2.87 (m, 1H), 2.76 (t, J=7.5 Hz, 2H), 2.13 (m, 1H), 1.90 (m, 1H), 1.83 (sextet, J=7.5 Hz, 2H), 1.03 (t, J=7.5 Hz, 3H).

53l. trans-2-propyl-4,5,5a,6,7,11b-hexahydro- 1,5-diaza-3-oxa-cyclopent-1-ena[c]phenanthrene-9,10-diol dihydrobromide Following the procedure of Example 1f, the compound of step 53k was converted to the title compound. MS m/z: 301 (M+H)$^+$, 318 (M+NH$_4$)$^+$. NMR (OD$_3$OD) δ:7.80 (s, 1H), 6.58 (s, 1H), 4.49 (m, 2H), 4.05 (d, J=12 Hz, 1H), 3.51 (m, 1H), 2.98 (m, 2H), 2.84 (t, J=7.5 Hz, 2H), 2.35 (m, 1H), 2.05 (m, 1H), 1.85 (sextet, J=7.5 Hz, 2H), 1,04 (t, J=7.5 Hz, 3H). Anal. Calcd. for C$_{17}$H$_{20}$N$_2$O$_3$.2HBr.0.6 H$_2$O: C, 43.17; H, 4.94; N, 5.92; Found: C, 43.13, H, 4.99; N, 5.72.

EXAMPLE 54 trans-2-propyl-4,5.5a,6,7,11b-hexahydro-1,5-diaza-3-thia-cyclopent-1-ena[c]phenanthrene-9,10-diol dihydrobromide 54a.

2-propyl-4-((2-tetrahydropyranyloxy)methyl)thiazole

Following the procedure of Example 29c, substituting 2-propyl-4-thiazolemethanol, from Example 27d above, for the 5-bromo-2-propyl-4-oxazolemethanol of step 29c, the title compound was prepared. NMR (CDCl$_3$) δ: 7.09 (s, 1H), 4.85 (d, J=12 Hz, 1H), 4.78 (t, J=3 Hz, 1H), 4.62 (d, J=12 Hz, 1H), 3.96–3.83 (m, 1H), 3.60–3.48 (m, 1H), 2.97 (t, J=7 Hz, 2H), 2.0–1.5 (m, 8H), 1.02 (t, J=7 Hz, 3H).

54b. 2-propyl-4-((2-tetrahydropyranyloxy)methyl)thiazole-5-carboxaldehyde

A solution of 2-propyl-4-((2-tetrahydropyranyloxy)methyl)thiazole (12.0 g, 49.8 mmol), from step 548 above, in 120 mL of THF was cooled to −78° C. and treated with n-butyllithium (20.0 mL, 2.5M solution in hexanes). The reaction mixture was stirred at −78° C. for 30 minutes, and 5.46 g (74.7 mmol) of DMF was added. The reaction mixture was stirred at −78° C. for 1.5 hours, then warmed to room temperature and quenched with satd NH$_4$Cl solution. The mixture was partitioned between water and ethyl acetate. The organic extract was washed with water and brine, dried over MgSO$_4$, and concentrated to afford 13.6 g of the title product as a viscous oil, which was taken to the next step without further purification. NMR (CDCl$_3$) δ:10.32 (s, 1H), 5.15 (d, J=12 Hz, 1H), 4.88 (d, J=12 Hz, 1H), 4.81 (t, J=3 Hz, 1H), 3.92–3.82 (m, 1H), 3.61–3.47 (m, 1H), 2.99 (t, J=7 Hz, 2H), 1.9–1.5 (m, 8H), 1.03 (t, J=7 Hz, 3H).

54c. 2-propyl-4-((2-tetrahydropyranyloxy)methyl)thiazole-5-methanol

To a solution of the aldehyde from step 54b above (13.6 g, 49 mmol) in 130 mL of ethanol was added 3.8 g (98 mmol) of sodium borohydride, and the reaction mixture was stirred for 2 hours at room temperature. The reaction was quenched with water, and the mixture was stirred for 0.5 hour then concentrated under vacuum. The residue was partitioned between water and methylene chloride. The organic extract was washed with water and brine, dried over $MgSO_4$, and concentrated to afford 13.3 g of the title compound as an oil. NMR ($CDCl_3$) δ:4.86 (d, J=12 Hz, 1H), 4.84–4.71 (m, 3H), 4.69 (t, J=3 Hz, 1H), 3.9–3.8 (m, 1H), 3.6–3.47 (m, 1H), 3.30 (t, J=7 Hz, 1H), 2.93 (t, J=7 Hz, 2H), 1.9–1.5 (m, 8H), 1.02 (t, J=7 Hz, 3H).

54d. trans-2-propyl-4,5,5a,6,7,11b-hexahydro-1,5-diaza-3-thia-cyclopent-1-ena[c]phenanthrene-9,10-diol dihydrobromide Following the procedures of Example 53, steps c through l, substituting the compound of step 54c above for the 2-propyl-4-((2-tetrahydropyranyloxy)methyl)-oxazole-5-methanol thereof, the title compound was prepared. mp 181°–184° C. MS m/z: 317 (M+H)⁺. NMR ($CD_3OD$) δ:7.64 (s, 1H), 6.51 (s, 1H), 4.64 (dd, J=2, 15 Hz, 1H), 4.55 (dd, J=2, 15 Hz, 1H), 4.20(d,J=11 Hz, 1H),3.56–3.46 (m, 1H), 3.01 (t, J=7 Hz, 2H), 3.02–2.94 (m, 2H), 2.45–2.32 (m, 1H), 2.02–1.96 (m, 1H), 1.90 (sextet, J=7 Hz, 2H), 1.07 (t, J=7 Hz, 3H). Anal. Calcd. for $C_{17}H_{22}Br_2N_2O_2S.0.6$ HBr: C, 38.76; H, 4.32; N, 5.32; Found: C, 38.69, H, 4.44; N, 5.02.

EXAMPLE 55 trans-2-ethyl-4,5,5a,6,7,11b-hexahydro-1-oxa-5-aza-cyclopent-2-ena[c]phenanthrene-9,10-diol hydrochloride 55a.
3,4-methylenedioxybenzenebutanoic acid, methyl ester The title compound was prepared from piperonal by reaction with (2-carboxyethyl)triphenylphosphonium bromide (per the method of Zjawiony and Peterson (*Org. Prep. Proc. Int.*, 23:163 (1991)), and esterification and hydrogenation of the intermediate with standard methods. NMR ($CDCl_3$) δ: 6.75–6.60 (m, 3H), 5.92 (s, 2H), 3.67 (s, 3H), 2.57 (t, J=7.5 Hz, 2H), 2.32 (t, J=7.5. Hz, 2H), 1.91 (quintet, J=7.5 Hz, 2H).

55b. 5-ethylfuran-2-carboxaldehyde

A sample of DMF (9.3 mL, 120 mmol) was cooled to 0° C. and $POCl_3$ (3.37 g, 22 mmol) was added, the mixture was stirred for 1 hour at 0° C., then 2-ethyl furan (1.92 g, 20 mmol) was added. The reaction was quenched by pouring onto ice, and the mixture was stirred for 18 hours. The mixture was extracted with hexane, which was dried over $MgSO_4$ and concentrated to give 1.71 g of the title compound (used without further purification).

55c, trans-1-(5-ethyl-2-furanyl)-1,2,3,4-tetrahydro-6,7-methylenedioxy-naphthalene -2-carboxylic acid To a freshly prepared solution of LDA (15 mmol) in 30 mL of THF cooled to −78° C. was added a solution of 3,4-methylenedioxybenzenebutanoic acid, methyl ester (14 mmol), from step 558 above, in 10 mL of THF. The solution was stirred for 5 minutes, and a solution of 5-ethylfuran-2-carboxaldehyde (13.8 mmol), from step 55b above, in 30 mL of THF was added. The reaction mixture was warmed to 0° C., and the reaction was quenched with 10 mL of satd NH4Cl. The organic layer was separated, and the aqueous layer was extracted with ether. The organic layers were combined, dried and concentrated. The residue was dissolved in 50 mL of methylene chloride, and the solution was cooled to 0° C. To this solution was added a solution of $SnCl_4$ (1M, 13 mmol) in methylene chloride, and the reaction mixtrue was stirred for 5 minutes. The reaction was quenched with 1 N HCl (10 mL). The organic layer was separated, and the aqueous layer was extracted with methylene chloride. The organic layers were combined, dried, filtered and concentrated. The crude methyl ester intermediate was hydrolyzed with KOH in methanol by standard procedures, and the title product was isolated (3.04 g). NMR ($CDCl_3$) δ:6.56 (s, 1H), 6.54 (s, 1H), 5.91–5.81 (m, 4H), 4.39 (d, J=7 Hz, 1H), 3.13 (m, 1H), 2.80 (t, J=7 Hz, 2H), 2.59 (q, J=8 Hz, 2H), 2.18–1.96 (m, 2H), 1.20 (t, J=8 Hz, 3H).

55c. trans-1-(5-ethyl-2-furanyl)-1,2,3,4-tetrahydro-6,7-methylenedioxy-2-naphthaleneamine The title compound was prepared from the compound of step 55b by a Curtius rearrangement procedure (Kim and Weinreb, *J. Org. Chem.*, 43:125 (1978)). NMR ($CDCl_3$) δ:6.57 (s, 1H), 6.40 (s, 1H), 6.02 (d, J=3 Hz, 1H), 5.90 (m 1H), 5.86 (s, 2H), 3.68 (d, J=9 Hz, 1H), 3.33 (m, 1H), 2.90–2.80 (m, 2H), 2.60 (m, 2H), 2.10–2.00 (m, 1H), 1.67 (m, 1H), 1.20 (t, J=8 Hz, 3H).

55d. trans-2-ethyl-4,5,5a,6,7,11b-hexahydro-9,10-methylenedioxy-1-oxa-5-aza-cyclopent -2-ena[c]phenanthrene The title compound was prepared from the compound of step 55c by the procedure described in Example 1e. NMR ($CDCl_3$) δ:7.55 (s, 1H), 6.61 (s, 1H), 5.90 (m, 2H), 5.84 (s, 1H), 3.93–3.72 (m, 2H), 3.70 (d, J=l 0 Hz, 1H), 2.96–2.82 (m, 3H), 2.70 (q, J=8 Hz, 2H), 2.16–2.06 (m, 1H), 1.88–1.75 (m, 1H), 1.27 (t, J=8 Hz, 3H).

55e. trans-2-ethyl-4,5,5a,6,7,11b-hexahydro-1-oxa-5-aza-cyclooent-2-ena[c]phenanthrene-9,10-diol hydrochloride The title compound was prepared from the compound of step 55d in quantitative yield using the procedure described in Example 40d. MS m/z: 286 (M+H)⁺. NMR ($CD_3OD$) δ:7.48 (s, 1H), 6.59 (s, 1H), 6.10 (s, 1H), 4.32–4.15 (m, 3H), 3.50 (m, 1H), 2.98 (m, 2H), 2.75 (q, J=8 Hz, 2H), 2.38–2.28 (m, 1H), 2.09–1.94 (m, 1H), 1.20 (t, J=8 Hz, 3H). Anal. Calcd. for $C_{17}H_{19}NO_3.1.5$ HCl.0.5 $H_2O$: C, 58.50; H, 6.21; N, 4.01;Found: C, 58.70, H, 6.37; N, 3.87.

COMPETITIVE BINDING

D-1 and D-2 Receptor Binding Assays

Homogenized rat caudate was incubated in the presence of [$^{125}I$]SCH-23982 (a selective antagonist of the dopamine D-1 receptor) and the compounds of this invention, according to procedures described by A. Sidhu, et al. in *European J Pharmacology*, 113:437 (1985) and in *European J Pharmacology*, 128:213 (1986). The compounds compete with the radiolabeled ligand for occupancy of the receptors and the molar potency of each compound was quantified. The affinity of the compound for the receptor (Ki) was calculated as described by Y. C. Cheng and W. H. Prusoff in *Biochemical Pharmacology*, 22: 3099 (1973) from the relationship $Ki=IC_{50}(1+[L]/K_D)$ where $IC_{50}$ is the concentration of test compound which produces a 50% inhibition in the specific binding of the radioligand, L; [L] is the concentration of radioligand; and $K_D$ is the affinity of the radioligand for the receptor.

The procedure for the dopamine D-2 receptor binding assay was similar to that used for the D-1 receptor assay. Homogenized rat caudate was the source of the D-2 receptors. The tissue homogenate was incubated in the presence of [$^3$H]-spiroperidol (a selective antagonist of the dopamine D-2 receptor) and the compounds being evaluated, according to the protocol described by T. Agui, N. Amlaiky, M. G. Caron and J. W. Kebabian in *Molecular Pharmacology*, 33:163 (1988). The molar affinity of the compound for the receptor binding site was calculated by the same method used for the D-1 receptor assay, assuming a competitive interaction between the compound and the radiolabeled ligand.

The competitive binding data (Ki values) from the D-1 and D-2 receptor binding assays are shown in Table 1. The Ki values are inversely proportional to the affinity of the compound for the receptor.

TABLE 1

| Competitive Binding for D-1 and D-2 Receptors | | |
|---|---|---|
| Example Number | D-1 Ki (μM) | D-2 Ki (μM) |
| dopamine | 8.0 | 6.3 |
| 1 | 0.018 | 0.16 |
| 2 | 0.045 | 0.83 |
| 3 | 0.006 | 0.64 |
| 4 | 0.002 | 0.34 |
| 5 | 0.018 | 1.4 |
| 6 | 0.051 | 3.3 |
| 7 | 0.02 | 1.7 |
| 8 | 0.094 | 3.0 |
| 9 | 0.051 | 2.3 |
| 10 | 0.56 | 4.6 |
| 11 | 0.15 | 3.1 |
| 12 | 1.0 | 10 |
| 13 | 0.077 | 0.91 |
| 14 | 0.008 | 0.14 |
| 15 | 0.013 | 0.15 |
| 16 | 0.022 | 0.45 |
| 17 | 0.16 | 1.5 |
| 18 | 0.060 | 0.52 |
| 19 | 0.36 | 0.75 |
| 20 | 0.008 | 0.29 |
| 21 | 0.015 | 0.066 |
| 22 | 0.012 | 0.66 |
| 23 | 0.006 | 0.29 |
| 24 | 0.006 | 1.27 |
| 25 | 0.073 | 1.31 |
| 27 | 0.011 | 0.21 |
| 28 | 0.052 | >5.0 |
| 29 | 0.006 | 0.29 |
| 30 | 0.062 | 0.56 |
| 31 | 0.687 | 0.54 |
| 32 | 0.004 | 0.13 |
| 33 | 0.282 | 0.56 |
| 34 | 0.004 | 0.42 |
| 35 | 0.440 | 1.76 |
| 36 | 0.517 | 2.08 |
| 37 | 0.710 | 3.19 |
| 38 | 1.43 | 2.58 |
| 39 | 0.45 | 1.62 |
| 40 | 0.015 | 0.48 |
| 41 | 0.021 | 0.60 |
| 42 | 0.453 | 0.64 |
| 43 | 0.028 | 0.12 |
| 44 | 0.025 | 0.38 |
| 45 | >2.5 | >5.0 |
| 46 | >5.0 | >5.0 |
| 47 | >10.0 | >5.0 |
| 49 | 0.010 | 0.490 |
| 50 | 0.012 | 0.365 |
| 51 | 0.011 | 0.382 |
| 52 | 0.058 | 0.051 |

TABLE 1-continued

| Competitive Binding for D-1 and D-2 Receptors | | |
|---|---|---|
| Example Number | D-1 Ki (μM) | D-2 Ki (μM) |
| 53 | 0.154 | 0.230 |
| 54 | 0.220 | >5.0 |
| 55 | 0.010 | 0.368 |

INTRINSIC ACTIVITY

The interaction of dopamine or a dopamine D-1 receptor agonist with the D-1 receptor causes a dose-dependent increase in the adenylate cyclase-catalyzed conversion of adenosine triphosphate (ATP) to cyclic adenosine monophosphate (cAMP). The functional activity of the compounds of the invention was determined by assaying, in vitro, their ability to either stimulate the enzyme adenylate cyclase to produce more cAMP (agonist activity) or to antagonize a dopamine-induced increase in cAMP levels. The protocol for the adenylate cyclase assays was described by K. J. Watling and J. E. Dowling in *J Neurochemistry*, 36:559 (1981) and by J. W. Kebabian, et al. in *Proc Natl Acad Sci. USA*, 69:2145 (1972). In order to determine agonist activity, cell-free tissue homogenates are incubated in an ionic buffer solution containing ATP and the compound being evaluated. The tissue was obtained from either goldfish retina or rat striatum.

Table 2, below, shows the intrinsic activity in an adenylate cyclase assay indicating that the compounds of the present invention are dopamine agonists at the D1 receptor.

ROTATION BEHAVIOR

The behavioral assay used was based on the rat rotational model. Striatal dopamine was depleted by the intracranial injection of 6-hydroxydopamine, a neurotoxin which specifically destroys catecholaminergic neurons. The intracranial injection was conducted on anesthetized animals using standard stereotaxic techniques (U. Ungerstedt and G. W. Arbuthnott, *Brain Research*, 24: 485, 1970, and U. Ungerstedt, *Acta Physiol. Scand. Suppl.* 367, 69: 1973). This unilateral lesioning of dopamine-containing neurons causes the post synaptic dopamine receptors to become supersensitive to dopaminergic stimulation in behavioral assays. When these striatal dopamine receptors are stimulated by the test compounds, the rats rotate or physically turn, in a direction that is away from the side of their body that receives the greater dopaminergic activation due to the receptor supersensitivity. Agonist activity was measured by the ability of the test compound to induce rotation.

Table 3, below, shows the rotation behavior of selected compounds of the present invention.

TABLE 2

| Agonist Activity in Adenylate Cyclase Assay | | |
|---|---|---|
| Example Number | EC50 (μM) | Intrinsic Activity (%) |
| dopamine | 2.5 | 100 |
| 1 | 0.047 | 85 |
| 2 | 0.26 | 81 |
| 3 | 0.027 | 100 |
| 4 | 0.021 | 104 |
| 5 | 0.057 | 104 |
| 6 | 0.074 | 99 |
| 7 | 0.028 | 87 |

TABLE 2-continued

Agonist Activity in Adenylate Cyclase Assay

| Example Number | EC50 (μM) | Intrinsic Activity (%) |
|---|---|---|
| 8 | 0.077 | 78 |
| 9 | 0.088 | 84 |
| 10 | 0.216 | 50 |
| 11 | 0.094 | 71 |
| 12 | 0.074 | 91 |
| 13 | 0.028 | 75 |
| 14 | 0.050 | 103 |
| 15 | 0.032 | 107 |
| 16 | 0.043 | 79 |
| 17 | 0.078 | 87 |
| 18 | 0.039 | 117 |
| 19 | 0.025 | 79 |
| 20 | 0.013 | 86 |
| 21 | 0.182 | 95 |
| 22 | 0.106 | 79 |
| 23 | 0.027 | 97 |
| 24 | 0.027 | 93 |
| 25 | 0.047 | 98 |
| 27 | 0.120 | 93 |
| 28 | 0.202 | 77 |
| 29 | 0.028 | 81 |
| 30 | 0.105 | 70 |
| 31 | 0.141 | 76 |
| 32 | 0.043 | 96 |
| 33 | 0.132 | 63 |
| 34 | 0.016 | 80 |
| 35 | 0.473 | 67 |
| 36 | 0.170 | 80 |
| 37 | 0.332 | 65 |
| 38 | 0.285 | 58 |
| 39 | 0.110 | 93 |
| 40 | 0.037 | 70 |
| 41 | 0.046 | 87 |
| 42 | 0.078 | 59 |
| 43 | 0.035 | 72 |
| 49 | 0.168 | 91 |
| 50 | 0.081 | 108 |
| 51 | 0.065 | 100 |
| 52 | 0.168 | 99 |
| 53 | 1.0 | 83 |
| 54 | 0.58 | 67 |
| 55 | 0.064 | 92 |

TABLE 3

Rotation Behavior

| Example Number | EC$_{50}$ (μmol/kg)sc |
|---|---|
| dopamine | |
| 3 | 0.077 |
| 4 | 0.04 |
| 5 | 0.15 |
| 6 | 0.12 |
| 7 | 0.17 |
| 8 | 0.55 |
| 12 | >3.0 |
| 13 | 0.07 |
| 14 | 0.22 |
| 15 | 0.18 |
| 16 | 1.01 |
| 18 | 1.5 |
| 20 | 0.11 |
| 22 | 0.2 |
| 23 | 0.05 |
| 24 | 0.04 |
| 25 | 0.06 |
| 27 | >1.0 |
| 28 | 0.4 |
| 29 | 0.41 |
| 30 | >1.0 |
| 32 | 0.06 |
| 34 | 0.04 |

TABLE 3-continued

Rotation Behavior

| Example Number | EC$_{50}$ (μmol/kg)sc |
|---|---|
| 40 | 0.12 |
| 41 | 0.07 |
| 43 | 0.25 |
| 48 | 0.04 |
| 49 | 0.03 |
| 50 | >1.0 |
| 51 | 0.33 |
| 52 | 0.32 |
| 54 | 0.21 |
| 55 | 0.17 |

What is claimed is:

1. A compound of the formula:

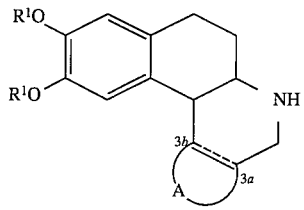

or a pharmaceutically-acceptable salt, ester or carbamate thereof, wherein:

R$^1$ is hydrogen or a prodrug moiety;

A and the atoms to which it is attached are selected from the group consisting of:

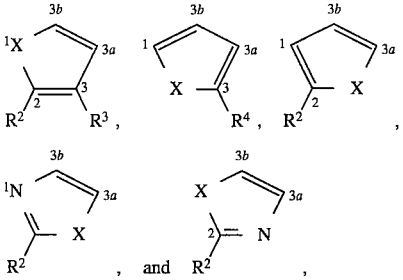

wherein:

X is sulfur or oxygen,

R$^2$ is hydrogen, C$_1$, CF$_3$, C$_1$–C$_6$-alkyl, C$_3$–C$_7$-cycloalkyl, —CH$_2$—C$_3$—C$_5$-cycloalkyl, phenyl or thienyl;

R$^3$ is hydrogen, or when R$^2$ is hydrogen, Cl, C$_1$–C$_6$-alkyl or CF$_3$, then R$^3$ is additionally Cl, C$_1$–C$_5$-alkyl or CF$_3$; and R$^4$ is hydrogen, Cl, C$_1$–C$_6$-alkyl, or C$_3$–C$_7$-cycloalkyl.

2. A compound according to claim 1, wherein A and the atoms to which it is attached are selected from the ring systems:

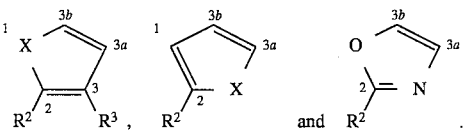

3. A compound according to claim 3, wherein A and the atoms to which it is attached are:

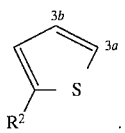

4. A compound according to claim 1, which is:
trans- 2-Methyl-4,5,5a,6,7,11b-hexahydro-1-thia-5-aza-cyclopent-2-ena[c]phenanthrene-9,10-diol;
trans-4,5,5a,6,7,11b-Hexahydro-2-thia-5-aza-cyclopent-3-ena[c]-phenanthrene-9,10-diol;
trans-2-Ethyl-4,5,5a,6,7,11b-hexahydro-3-thia-5-aza-cyclopent-1-ena[c]phenanthrene-9,10-diol;
(−)-trans-2-Ethyl-4,5,5a,6,7,11b-hexahydro-3-thia-5-aza-cyclopent-1-e na[c]phenanthrene-9,10-diol;
trans-2-Propyl-4,5,5a,6,7,11b-hexahydro-3-thia-5-aza-cyclopent-1-ena[c]phenanthrene-9,10-diol;
trans-2-(1,1 -Dimethylethyl)-4,5,5a,6,7,11b-hexahydro-3-thia-5-aza-cyclopent-1-ena[c]-phenanthrene-9,10-diol;
trans-2-(2-Propyl)-4,5,5a,6,7,11b-hexahydro-3-thia-5-aza-cyclopent-1-ena[c]phenanthrene-9,10-diol;
trans-2-Butyl-4,5,5a,6,7,11b-hexahydro-3-thia-5-aza-cyclopent-1-ena[c]phenanthrene-9,10-diol;
trans-2-(2-Methylpropyl)-4,5,5a,6,7,11b-hexahydro-3-thia-5-aza-cyclopent-1-ena[c]-phenanthrene-9,10-diol;
trans-2-(2,2-Di methylpropyl)-4,5,5a,6,7,11b-hexahydro-3-thia-5-aza-cyclopent-1-ena[c]-phenanthrene-9,10-diol;
trans-2-Cyclohexyl-4,5,5a,6,7,11b-hexahydro-3-thia-5-aza-cyclopent-1-ena[c]phenanthrene-9,10-diol;
trans-2-Phenyl-4,5,5a,6,7,11b-hexahydro-3-thia-5-aza-cyclopent-1-ena[c]phenanthrene-9,10-diol;
trans-2-(1,1-Dimethylethyl)-4,5,5a,6,7,11b-hexahydro-1-thia-5-aza-cyclopent-2-ena[c]-phenanthrene-9,10-diol;
trans-2-Ethyl-4,5,5a,6,7,11b-hexahydro-1-thia-5-aza-cyclopent-2-ena[c]phenanthrene-9,10-diol;
trans-2-Propyl-4,5,5a,6,7,11b-hexahydro-1-thia-5-aza-cyclopent-2-ena[c]phenanthrene-9,10-diol;
trans-2-Butyl-4,5,5a,6,7,11b-hexahydro-1-thia-5-aza-cyclopent-2-ena[c]phenanthrene-9,10-diol;
trans-2-Cyclohexyl-4,5,5a,6,7,11b-hexahydro-1-thia-5-aza-cyclopent-2-ena[c]phenanthrene-9,10-diol;
trans-4,5,5a,6,7,11b-Hexahydro-1-thia-5-aza-cyclopent-2-ena[c]-phenanthrene-9,10-diol;
trans-2-Phenyl-4,5,5a,6,7,11b-hexahydro-1-thia-5-aza-cyclopent-2-ena[c]phenanthrene-9,10-diol;
(−)-trans-2-Propyl-4,5,5a,6,7,11b-hexahydro-3-thia-5-aza-cyclopent-1-ena[c]phenanthrene-9,10-diol;
trans-2,3-Dimethyl-4,5,5a,6,7,11b-hexahydro-1-thia-5-aza-cyclopent-2-ena[c]phenanthrene-9,10-diol;
trans-2-Methyl-4,5,5a,6,7,11b-hexahydro-3-thia-5-aza-cyclopent-1-ena[c]phenanthrene-9,10-diol;
(−)-trans-2-Methyl-4,5,5a,6,7,11b-hexahydro-3-thia-5-aza-cyclopent-1-ena[c]phenanthrene-9,10-diol;
(−)-trans-2-(1,1 -Dimethylethyl)-4,5,5a,6,7,11b-hexahydro-3-thia-5-aza-cyclopent-1-ena[c]-phenanthrene-9,10-diol;
trans-4,5,5a,6,7,11b-Hexahydro-3-thia-5-aza-cyclopent-1-ena[c]-phenanthrene-9,10-diol;
trans-2-Trifluoromethyl-4,5,5a,6,7,11b-hexahydro-3-thia-5-aza-cyclopent-1-ena[c]phenanthrene-9,10-diol;
trans-2-Propyl-4,5,5a,6,7,11b-hexahydro-1-thia-3,5-diaza-cyclopent-2-ena[c]phenanthrene-9,10-diol;
trans-2-Propyl-4,5,5a,6,7,11b-hexahydro-3-thia-1,5-diaza-cyclopent-1-ena[c]phenanthrene-9,10-diol;
trans-2-Propyl-4,5,5a,6,7,11b-hexahydro-1-oxa-3,5-diaza-cyclopent-2-ena[c]phenanthrene-9,10-diol;
trans-2-(3-Methylbutyl)-4,5,5a,6,7,11b-hexahydro-1-thia-5-aza-cyclopent-2ena[c]phenanthrene-9,10-diol;
trans-2-Hexyl-4,5,5a,6,7,11b-hexahydro-1-thia-5-aza-cyclopent-2-ena[c]phenanthrene-9,10-diol;
trans-2-Chloro-4,5,5a,6,7,11b-hexahydro-1-thia-5-aza-cyclopent-2-ena[c]phenanthrene-9,10-diol;
trans-2-(1-Cyclopentylmethyl)-4,5,5a,6,7,11b-hexahydro-1-thia-5-aza-cyclopent-2-ena[c]-phenanthrene-9,10-diol;
trans-2-1sopropyl-4,5,5a,6,7,11b-hexahydro-1-thia-5-aza-cyclopent-2-ena[c]phenanthrene-9,10-diol;
trans-2-(3-Methylbutyl)-4,5,5a,6,7,11b-hexahydro-3-thia-5-aza-cyclopent-1-ena[c]phenanthrene-9,10-diol;
trans-2-Pentyl-4,5,5a,6,7,11b-hexahydro-3-thia-5-aza-cyclopent-1-ena[c]phenanthrene-9,10-diol;
trans-2-(2-Thiophenyl)-4,5,5a,6,7,11b-hexahydro-3-thia-5-aza-cyclopent-1-ena[c]-phenanthrene-9,10-diol;
trans-2-Hexyl-4,5,5a,6,7,11b-hexahydro-3-thia-5-aza-cyclopent-1-ena[c]phenanthrene-9,10-diol;
trans-2-(Cyclopentylmethyl)-4,5,5a,6,7,11b-hexahydro-3-thia-5-aza-cyclopent-1-ena[c]-phenanthrene-9,10-diol;
trans-2-Ethyl-4,5,5a,6,7,11b-hexahydro-3-oxa-5-aza-cyclopent-1-ena[c]phenanthrene-9,10-diol;
trans-2-Propyl-4,5,5a,6,7,11b-hexahydro-3-oxa-5-aza-cyclopent-1-ena[c]phenanthrene-9,10-diol;
trans-2-Phenyl-4,5,5a,6,7,11b-hexahydro-3-oxa-5-aza-cyclopent-1-ena[c]phenanthrene-9,10-diol;
trans-3-Propyl-4,5,5a,6,7,11b-hexahydro-2-thia-5-aza-cyclopent-3-ena[c]phenanthrene-9,10-diol; and
(−)-trans-9,10-Diacetyloxy-2-propyl-4,5,5a,6,7,11b-hexahydro-3-thia-5-aza-cyclopent -1-ena[c]phenanthrene;
trans-2-Chloro-4,5,5a,6,7,11b-hexahydro-3-thia-5-aza-cyclopent-1-ena[c]phenanthrene-9,10-diol;
trans-2-1sopropyl-4,5,5a,6,7,11b-hexahydro-1-oxa-3,5-diaza-cyclopent-2-ena[c]phenanthrene-9,10-diol;
trans-2-Methyl-4,5,5a,6,7,11b-hexahydro-1-oxa-3,5-diaza-cyclopent-2-ena[c]phenanthrene-9,10-diol;
trans-3-Propyl-4,5,5a,6,7,11b-hexahydro-1-thia-5-aza-cyclopent-2-ena[c]phenanthrene-9,10-diol;
trans-2-Propyl-4,5,5a,6,7,11b-hexahydro-1,5-diaza-3-oxa-cyclopent-1-ena[c]phenanthrene-9,10-diol;
trans-2-propyl-4,5,5a,6,7,11b-hexahydro-1,5-diaza-3-thia-cyclopent-1-ena[c]phenanthrene-9,10-diol;
trans-2-Ethyl-4,5,5a,6,7,11b-hexahydro-1-oxa-5-aza-cyclopent-2-ena[c]phenanthrene-9,10-diol; or
trans-2-Trifluoromethyl-4,5,5a,6,7,11b-hexahydro-1-thia-3,5-diaza-cyclopent-2-ena[c]phenanthrene-9,10-diol.
5. A compound according to claim 1, which is:
trans-2-Ethyl-4,5,5a,6,7,11b-hexahydro-3-thia-5-aza-cyclopent-1-ena[c]phenanthrene-9,10-diol;
(−)-trans-2-Ethyl-4,5,5a,6,7,11b-hexahydro-3-thia-5-aza-cyClopent-1-ena[c]phenanthrene-9,10-diol;
trans-2-Propyl-4,5,5a,6,7,11b-hexahydro-3-thia-5-aza-cyclopent-1-ena[c]phenanthrenc-9,10-diol;

trans-2-(1,1-Dimethylethyl)-4,5,5a,6,7,11b-hexahydro-3-thia-5-aza-cyclopent-1-ena[c]-phenanthrene-9,10-diol;

trans-2-Butyl-4,5,5a,6,7,11b-hexahydro-3-thia-5-aza-cyclopent-1-ena[c]phenanthrene-9,10-diol;

(–)-trans-2-Propyl-4,5,5a,6,7,11b-hexahydro-3-thia-5-aza-cyclopent-1-ena[c]phenanthrene-9,10-diol;

trans-2-Methyl-4,5,5a,6,7,11b-hexahydro-3-thia-5-aza-cyclopent-1-ena[c]phenanthrene-9,10-diol;

(–)-trans-2-Methyl-4,5,5a,6,7,11b-hexahydro-3-thia-5-aza-cyclopent-1-ena[c]phenanthrene-9,10-diol;

(–)-trans-2-(1,1-Dimethylethyl)-4,5,5a,6,7,11b-hexahydro-3-thia-5-aza-cyclopent-1-ena[c]-phenanthrene-9,10-diol;

trans-2-Propyl-4,5,5a,6,7,11b-hexahydro-1-oxa-3,5-diaza-cyclopent-2-ena[c]phenanthrene-9,10-diol;

trans-2-Ethyl-4,5,5a,6,7,11b-hexahydro-3-oxa-5-aza-cyclopent-1-ena[c]phenanthrene-9,10-diol;

trans-2-Propyl-4,5,5a,6,7,11b-hexahydro-3-oxa-5-aza-cyclopent-1-ena[c]phenanthrene-9,10-diol;

(–)-trans-9,10-Diacetyloxy-2-propyl-4,5,5a,6,7,11b-hexahydro-3-thia-5-aza-cyclopent-1-ena[c]phenanthrene;

trans-2-Chloro-4,5,5a,6,7,11b-hexahydro-3-thia-5-aza-cyclopent-1-ena[c]phenanthrene-9,10-diol; or trans-2-Methyl-4,5,5a,6,7,11b-hexahydro-1-oxa-3,5-diaza-cyclopent-2-ena[c]phenanthrene-9,10-diol.

6. A compound according to claim 1, which is:

trans-2-Ethyl-4,5,5a,6,7,11b-hexahydro-3-thia-5-aza-cyclopent-1-ena[c]phenanthrene-9,10-diol;

(–)-trans-2-Ethyl-4,5,5a,6,7,11b-hexahydro-3-thia-5-aza-cyclopent-1-ena[c]phenanthrene-9,10-diol;

trans-2-Propyl-4,5,5a,6,7,11b-hexahydro-3-thia-5-aza-cyclopent-1-ena[c]phenanthrene-9,10-diol;

trans-2-(1,1-Dimethylethyl)-4,5,5a,6,7,11b-hexahydro-3-thia-5-aza-cyclopent-1-ena[c]-phenanthrene-9,10-diol;

trans-2-Butyl-4,5,5a,6,7,11b-hexahydro-3-thia-5-aza-cyclopent-1-ena[c]phenanthrene-9,10-diol;

(–)-trans-2-Propyl-4,5,5a,6,7,11b-hexahydro-3-thia-5-aza-cyclopent-1-ena[c]phenanthrene-9,10-diol;

trans-2-Methyl-4,5,5a,6,7,11b-hexahydro-3-thia-5-aza-cyclopent-1-ena[c]phenanthrene-9,10-diol;

(–)-trans-2-Methyl-4,5,5a,6,7,11b-hexahydro-3-thia-5-aza-cyclopent-1-ena[c]phenanthrene-9,10-diol;

(–)-trans-2-(1,1-Dimethylethyl)-4,5,5a,6,7,11b-hexahydro-3-thia-5-aza-cyclopent-1-ena[c]-phenanthrene-9,10-diol; or (–)-trans-9,10-Diacetyloxy-2-propyl-4,5,5a,6,7,11b-hexahydro-3-thia-5-aza-cyclopent-1-ena[c]phenanthrene.

7. A pharmaceutical composition for selectively binding and activating dopaminergic receptors comprising a pharmaceutically-acceptable carrier and a therapeutically-effective amount of a compound according to claim 1.

8. A pharmaceutical composition for treating dopamine-related neurological, psychological, cardiovascular, cognitive or attention disorders or substance abuse or addictive behavior, or a combination of these indications, comprising a pharmaceutically-acceptable carrier and a therapeutically-effective amount of a compound of claim 5.

9. A method for treating dopamine-related neurological, psychological, cardiovascular, cognitive or attention disorders, substance abuse or addictive behavior, or a combination of these indications, characterized by abnormal dopaminergic activity comprising administering to a patient in need of such treatment a therapeutically-acceptable amount of a compound according to claim 1.

10. The compound (–)-trans-2-Propyl-4,5,5a,6,7,11b-hexahydro-3-thia-5-aza-cyclopent-1-ena[c]-phenanthrene-9,10-diol.

11. The compound (–)-trans-9,10-Diacetyloxy-2-propyl-4,5,5a,6,7,11b-hexahydro-3-thia-5-aza-cyclopent-1-ena[c]phenanthrene.

* * * * *

UNITED STATES PATENT AND TRADEMARK OFFICE
CERTIFICATE OF CORRECTION

PATENT NO. : 5,597,832
DATED : January 28, 1997
INVENTOR(S) : Michaelides, et. Al.

It is certified that error appears in the above-indentified patent and that said Letters Patent is hereby corrected as shown below:

In the abstract, line 7, change " 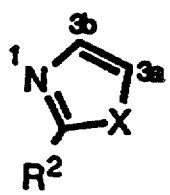 " to -- 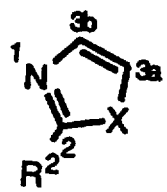 --.

Column 70, lines 40-44, change " 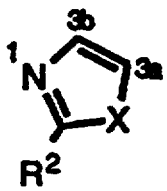 " to -- 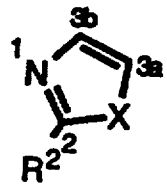 --.

Column 70, line 48, change "$C_1$" to --Cl--.

Column 70, line 65, change "claim 3" to --claim 1--.

Column 71, line 16, change "e na" to --ena--.

Column 71, line 29, change "Di methylpropyl" to --Dimethylpropyl--.

Column 71, line 55, change "ena[c]phenanthrene" to --ena[c]-phenanthrene--.

UNITED STATES PATENT AND TRADEMARK OFFICE
CERTIFICATE OF CORRECTION

PATENT NO. : 5,597,832  
DATED : January 28, 1997  
INVENTOR(S) : Michaelides, et. Al.

It is certified that error appears in the above-indentified patent and that said Letters Patent is hereby corrected as shown below:

Column 71, line 67, change "ena[c]phenanthrene" to --ena[c]-phenanthrene--.

Column 72, line 8, change "2ena[c]phenanthrene" to --2-ena[c]-phenanthrene--.

Column 72, line 16, change "1sopropyl" to --Isopropyl--.

Column 72, line 65, change "cyClopent" to --cyclopent--.

Column 73, line 38, change "Di methylethyl" to --Dimethylethyl--.

Signed and Sealed this

Seventeenth Day of June, 1997

*Attest:*

BRUCE LEHMAN

*Attesting Officer*   Commissioner of Patents and Trademarks